US007678813B2

(12) United States Patent
Clark et al.

(10) Patent No.: US 7,678,813 B2
(45) Date of Patent: Mar. 16, 2010

(54) AZADECALIN GLUCOCORTICOID RECEPTOR MODULATORS

(75) Inventors: Robin D. Clark, Lawai, HI (US); Nicholas C. Ray, Harlow (GB); Paul Blaney, Harlow (GB); Christopher Hurley, Harlow (GB); Hazel Hunt, Harlow (GB); David Clark, Harlow (GB); Karen Williams, Harlow (GB)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 10/596,998

(22) PCT Filed: Jan. 10, 2005

(86) PCT No.: PCT/US2005/000607

§ 371 (c)(1),
(2), (4) Date: Mar. 8, 2007

(87) PCT Pub. No.: WO2005/070893

PCT Pub. Date: Aug. 4, 2005

(65) Prior Publication Data

US 2007/0203179 A1    Aug. 30, 2007

Related U.S. Application Data

(60) Provisional application No. 60/535,460, filed on Jan. 9, 2004.

(51) Int. Cl.
*A61K 31/47* (2006.01)
*C07D 217/02* (2006.01)
*C07D 417/12* (2006.01)

(52) U.S. Cl. .............. 514/309; 514/307; 546/139; 546/141; 546/148

(58) Field of Classification Search .................. None
See application file for complete search history.

(56) References Cited

FOREIGN PATENT DOCUMENTS

| JP | 32-002220 B | 4/1957 |
| JP | 04-368384 A | 12/1992 |
| WO | WO 94/10150 A1 | 5/1994 |
| WO | WO 2004/065351 A1 | 8/2004 |

OTHER PUBLICATIONS

Uchida et al, Tetrhedron Letters, 1999, vol. 40, No. 1, pp. 113-116.*
Database Crossfile Beilstein; Beilstein Institut Zur Foerderung der Chemischen Wissenschaft; Accession No. 101172-52-5 (BRN); Jun. 27, 1988.

Barth, Martine M. et al.; "Structural and Stereoelectronic Requirements for the Inhibition of Mammalian 2,3-Oxidosqualene Cyclase by Substituted Isoquinoline Derivatives"; *J. Med. Chem.*; 1996; pp. 2302-2312; vol. 39, No. 12; American Chemical Society.
Christoffers, Jens, et al.; "Copper-Catalyzed Asymmetric Michael Reactions with α-Amino Acid Amides: Synthesis of an Optically Active Piperidine Derivative"; *Eur. J. Org. Chem.*; 2002; pp. 1505-1508; Wiley-VCH Verlag; Weinheim, Germany.
Christoffers, Jens, et al.; "Transformation of an Optically Active Decahydro-6-isoquinolone Scaffold: Perfect Felkin-Anh Diasteresoselectivity"; *Organic Letters*; Feb. 3, 2004; pp. 1171-1173; vol. 6, No. 7; American Chemical Society.
Christoffers, Jens, et al.; "Synthesis of an Optically Active Decahydro-6-isoquinolone Scaffold with a Quaternary Stereocenter"; *Eur. J. Org. Chem.*; Jun. 2004; pp. 2701-2706; Wiley-VCH Verlag; Weinheim, Germany.
Christoffers, Jens, et al.; "Absolute Configuration of Methyl (+)-1,2,3,4,6,7,8,8a-Octahydro-6-isoquinolone-8a-carboxylate and Stereochemistry of a Copper-Catalyzed Asymmetric Michael Reaction"; *Zeitschrift Fuer Naturforschung B Chemical Sciences*; 2004; vol. 59, No. 4; pp. 375-379; Verlag der Zeitschrift fuer Naturforschung; Tuebingen, Germany.
Elmore, Steven W., et al.; "Nonsteroidal Selective Glucocorticoid Modulatores: the Effect of C-5 Alkyl Substitution on the Transcriptional Activation/Repression Profile of 2,5-Dihydro-10-methoxy-2,2,4-trimethyl-1H-[1]benzopyrano[3,4-f]quinolines"; *J. Med. Chem*; 2001; pp. 4481-4491; vol. 44, No. 25; American Chemical Society; Washington, D.C.
Gupta, Arun K.D. et al.; "Studies on Carboxylation in Heterocyclic Systems"; *J. Sci. Industr. Res.*; Aug. 1961; pp. 394-397; vol. 20B.
Hsin, Ling-Wei, et al.; "Stereoselective synthesis of morphine fragments trans- and cis-octahydro-1H-benzo[4,5]furo[3,2-e]isoquinolines"; *Tetrahedron*; Jan. 10, 2005; pp. 513-520; vol. 61, No. 2; Elsevier Ltd.
Kugita, Hiroshi; "Studies on the Syntheses of Hydrogenated Quinolines and Isoquinolines as Analgesics"; *Pharmaceutical Bulletin*; 1956; pp. 29-34; vol. 4.
Magee, David I., et al.; "Construction of cis- and trans-Decahydroisoquinolines via Heterogeneous Catalytic Hydrogenation"; *J. Org. Chem.*; 1999; pp. 2549-2554; vol. 64, No. 7; American Chemical Society.
Schultz, Arthur G., et al.; "Heteroatom Directed Photoarylation. Synthetic Potential of the Heteroatom Oxygen."; *Journal of the American Chemical Society*; Mar. 29, 1978; pp. 2150-2162; vol. 100, No. 7; American Chemical Society.
Schultz, Arthur G., et al.; "Studies Directed at a Synthesis of the Morphine Alkaloids. A Photochemical Approach."; *J. Org. Chem.*; 1985; pp. 217-231; vol. 50, No. 2; American Chemical Society.
Spitz, Irving M., et al.; "Mifepristone (RU 486)—A Modulator of Progestin and Glucocorticoid Action"; *The New England Journal of Medicine*; Aug. 5, 1993; pp. 404-412; Massachusetts Medical Society; Waltham, Massachusetts.

* cited by examiner

*Primary Examiner*—Zinna N Davis
(74) *Attorney, Agent, or Firm*—Townsend and Townsend and Crew LLP

(57) ABSTRACT

The present invention provides a novel class of azadecalin compounds and methods of using the compounds as glucocorticoid receptor modulators.

21 Claims, No Drawings

AZADECALIN GLUCOCORTICOID RECEPTOR MODULATORS

CROSS-REFERENCES TO RELATED APPLICATIONS

This application is a 371 of PCT/US05/00607 filed Jan. 10, 2005 which claims the benefit of U.S. Provisional Patent Application No. 60/535,460, filed Jan. 9, 2004, which is incorporated herein by reference in its entirety for all purposes.

BACKGROUND OF THE INVENTION

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which differs in only the last fifteen amino acids. The two types of GR have high affinity for their specific ligands, and are considered to function through the same transduction pathways.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Patients with some forms of psychiatric illnesses have been found to have increased levels of cortisol (Krishnan (1992) *Prog. Neuro-Psychophannacol. & Biol. Psychiat.* 16:913-920). For example, some depressed individuals can be responsive to treatments which block the effect of cortisol, as by administering GR antagonists (Van Look (1995) *Human Reproduction Update* 1:19-34). In one study, a patient with depression secondary to Cushing's Syndrome (hyperadrenocorticism) was responsive to a high dose, up to 1400 mg per day, of GR antagonist mifepristone (Nieman (1985) *J. Clin Endocrinol. Metab.* 61:536). Another study which used mifepristone to treat Cushing's syndrome found that it improved the patients' conditions, including their psychiatric status (Chrousos, pp 273-284, In: Baulieu, ed. *The Antiprogestin Steroid RU 486 and Human Fertility Control.* Plenum Press, New York (1989), Sartor (1996) *Clin. Obstetrics and Gynecol.* 39:506-510).

Psychosis has also been associated with Cushing's syndrome (Gerson (1985) *Can. J. Psychiatry* 30:223-224; Saad (1984) *Am. J. Med.* 76:759-766). Mifepristone has been used to treat acute psychiatric disturbances secondary to Cushing's syndrome. One study showed that a relatively high dose of mifepristone (400 to 800 mg per day) was useful in rapidly reversing acute psychosis in patients with severe Cushing Syndrome due to adrenal cancers and ectopic secretion of ACTH from lung cancer (Van der Lely (1991) *Ann. Intern. Med.* 114:143; Van der Lely (1993) *Pharmacy World & Science* 15:89-90; Sartor (1996) supra).

A treatment for psychosis or the psychotic component of illnesses, such as psychotic major depression, has recently been discovered (Schatzberg et al., U.S. Pat. No. 6,150,349). The treatment includes administration of an amount of a glucocorticoid receptor antagonist effective to ameliorate the psychosis. The psychosis may also be associated with psychotic major depression, schizoaffective disorder, Alzheimer's Disease and cocaine addiction.

Thus, there exists a great need for a more effective and safer treatment for illnesses and conditions associated with the glucocorticoid receptors, including psychotic major depression. The present invention fulfills these and other needs.

SUMMARY OF THE INVENTION

In a first aspect, the present invention provides a compound having the formula:

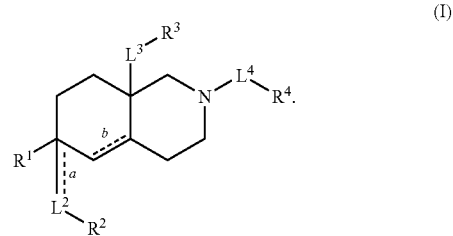

(I)

In Formula (I), $L^2$ and $L^4$ are independently selected from a bond, substituted or unsubstituted alkylene, and substituted or unsubstituted heteroalkylene. $L^3$ is a member selected from a bond, substituted or unsubstituted alkylene, substituted or unsubstituted heteroalkylene, —C(O)—, —C(O)NH—, and —S(O)$_u$—. The symbol u represents 0, 1, or 2. The dashed lines a and b are optionally a bond.

$R^1$ is absent or selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^2$ is selected from =O, =N—OR$^{2A}$, =CR$^{2B}$R$^{2C}$, hydrogen, —OR$^{2D}$, —C(O)R$^{2D}$, —C(O)NR$^{2E}$R$^{2F}$, —NR$^{2E}$R$^{2F}$, substituted or unsubstituted alkyl substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{2A}$, $R^{2B}$, $R^{2C}$ and $R^{2D}$ are members independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{2E}$ and $R^{2F}$ are independently selected from hydrogen, substituted or unsubstituted alkyl, substituted or unsubstituted heteroalkyl, substituted or unsubstituted aryl, substituted or unsubstituted heterocycloalkyl, —S(O)$_m$R$^{2E1}$ and —S(O)$_m$NR$^{2E2}$R$^{2E3}$. The symbol m represents the integers 0, 1, or 2. $R^{2E}$ and $R^{2F}$ may be joined to form a substituted or unsubstituted ring with the nitrogen to which they are attached. $R^{2E1}$, $R^{2E2}$, and $R^{2E3}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{2E2}$ and $R^{2E3}$ may be joined to form a substituted or unsubstituted ring with the nitrogen to which they are attached. In some embodiments, the substituted or unsubstituted ring formed by $R^{2E2}$ and $R^{2E3}$, and $R^{2E}$ and $R^{2F}$, may contain additional heteroatoms such as a nitrogen or oxygen (see "optionally joined together to form a ring," in the definitions section above). In addition, $R^2$ and $R^1$ may be optionally joined to form a substituted or unsubstituted ring $R^3$ is selected from substituted or unsubstituted higher alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^{3A}$, and $NR^{3B}R^{3C}$. $R^{3A}$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{3B}$ and $R^{3C}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{3B}$ and $R^{3C}$ may optionally join to form a substituted or unsubstituted ring with the nitrogen to which they are attached However, $R^3$ is not lower alkyl.

$R^4$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $—S(O)_tR^{4A}$, $—S(O)_tNR^{4B}R^{4C}$, $—C(O)R^{4A}$, $—C(O)OR^{4A}$, $—C(O)NR^{4B}R^{4C}$. The symbol t represents the integers 0, 1, or 2. $R^{4A}$, $R^{4B}$, $R^{4C}$, $R^{4D}$, $R^{4E}$, and $R^{4F}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{4B}$ and $R^{4C}$ may be joined to form a substituted or unsubstituted ring with the nitrogen to which they are attached.

In another aspect, the present invention provides methods of modulating glucocorticoid receptor activity using the techniques described above. In an exemplary embodiment, the method includes contacting a GR with a compound of the present invention, such as the compound of Formula (I), and detecting a change in GR activity.

In another aspect, the present invention provides pharmaceutical compositions comprising a pharmaceutically acceptable excipient and a compound of the present invention, such as the compound of Formula (I) provided above.

In still another aspect, the present invention provides a method for the treatment of a disorder or condition through modulation of a glucocorticoid receptor. In this method, a subject in need of such treatment is administered an effective amount of a compound having one of the formulae provided above.

DETAILED DESCRIPTION OF THE INVENTION

Abbreviations and Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkane, as exemplified, but not limited, by $—CH_2CH_2CH_2CH_2—$. Typically, an alkyl (or alkylene) group will have from 1 to 24 carbon atoms, with those groups having 10 or fewer carbon atoms being preferred in the present invention.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)—CH_3$, $—O—CH_3$, $—O—CH_2—CH_3$, and $—CN$. Up to two heteroatoms may be consecutive, such as, for example, $—CH_2—NH—OCH_3$ and $—CH_2—O—Si(CH_3)_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as $—C(O)R'$, $—C(O)NR'$, $—NR'R''$, $—OR'$, $—SR'$, and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NRS(O)$_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NRS(O)$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" is meant to include oxygen (O), nitrogen (N), sulfur (S), phosphorus (P), and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

Where two substituents are "optionally joined together to form a ring," the two substituents are covalently bonded together with the atom or atoms to which the two substituents are joined to form a substituted or unsubstituted aryl, a substituted or unsubstituted heteroaryl, a substituted or unsubstituted cycloalkyl, or a substituted or unsubstituted heterocycloalkyl ring.

Where group is described as substituted with a substituent, such as an R substituent ("R-substituted), the group may contain more than one substituent, where each substituent is optionally different. For example, where a $(C_1-C_{10})$alkyl is $R^{3D7}$-substituted, the $(C_1-C_{10})$alkyl may be substituted with one or more $R^{3D7}$ substituents, wherein each $R^{3D7}$ substituent is optionally different. Thus, the terms "a," "an," or "a(n)", when used in reference to a group of substituents herein, mean one or more.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

It will be apparent to one skilled in the art that certain compounds of this invention may exist in tautomeric forms, all such tautomeric forms of the compounds being within the scope of the invention.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs (e.g. dexamethasone). The term includes isoforms of GR, recombinant GR and mutated GR.

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than the mineralocorticoid receptor (MR).

A patient "not otherwise in need of treatment with a glucocorticoid receptor modulator" is a patient who is not suffering from a condition which is known in the art to be effectively treatable with glucocorticoid receptor modulators. Conditions known in the art to be effectively treatable with glucocorticoid receptor modulators include diabetes, Cushing's disease, drug withdrawal, psychosis, dementia, stress disorders, psychotic major depression, as well as those described below.

"Azadecalin," as used herein, means a compound having the general structure of Formula (I) as described below.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention successfully treat a patient's delirium by decreasing the incidence of disturbances in consciousness or cognition.

An "additional ring heteroatom" refers to a heteroatom that forms part of a substituted or unsubstituted ring (e.g., a heterocycloalkyl or heteroaryl) that is not the point of attachment of the ring toward the azadecalin core. The azadecalin core is the fused ring portion of the compound of Formula (I).

The term "higher alkyl" refers to those alkyl groups having at least six carbon atoms. The term "lower alkyl" refers to those alkyl groups having from one to five carbon atoms.

Description of the Embodiments

I. Glucocorticoid Receptor Modulators

It has now been discovered that azadecalin compounds are potent modulators of glucocorticoid receptors ("GR"). GR modulators typically act as agonists, partial agonists or antagonists of GR thereby affecting a wide array of cellular functions, physiological functions and disease states.

Cortisol acts by binding to an intracellular glucocorticoid receptor. In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

GR modulators are typically efficacious agents for influencing important cellular and physiological functions such as carbohydrate, protein and lipid metabolism; electrolyte and water balance; and functions of the cardiovascular system, kidney, central nervous system, immune system, skeletal muscle system and other organ and tissue systems. GR modulators may also affect a wide variety of disease states, such as obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoperosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multi-drug resistance, addiction, psychosis, anorexia, cathexia, post-traumatic stress syndrome, post-surgical bone fracture, medical catabolism, and muscle frailty.

In a first aspect, the present invention provides an azadecalin GR modulator having the formula:

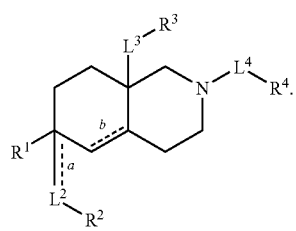

(I)

In Formula (I), $L^2$ and $L^4$ are independently selected from a bond, substituted or unsubstituted alkylene, and substituted or unsubstituted heteroalkylene. $L^3$ is a member selected from a bond, substituted or unsubstituted alkylene, substituted or unsubstituted heteroalkylene, —C(O)—, —C(O)NH—, and —S(O)$_u$—. The symbol u represents 0, 1, or 2.

The dashed lines a and b are optionally a bond. One skilled in the art will immediately recognize that the normal rules of valency apply for the atoms of Formula (I). Thus, where a is a bond, $R^1$ is absent and where $L^2$ is a bond, $R^2$ is directly attached to the azadecalin core. For example, where $L^2$ is a bond and $R^2$ is =O, it is understood that $R^1$ is absent and the dashed line a is a bond connecting $R^2$ to the azadecalin core, as shown in the formula below:

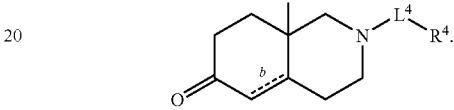

(II)

In Formula (I), $R^1$ is absent or selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^2$ is selected from =O, =N—OR$^{2A}$, =CR$^{2B}$R$^{2C}$, hydrogen, —OR$^{2D}$, —C(O)R$^{2D}$, —C(O)NR$^{2E}$R$^{2F}$, —NR$^{2E}$R$^{2F}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. R$^{2A}$, R$^{2B}$, R$^{2C}$ and R$^{2D}$ are members independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. R$^{2E}$ and R$^{2F}$ are independently selected from hydrogen, substituted or unsubstituted alkyl, substituted or unsubstituted heteroalkyl, substituted or unsubstituted aryl, substituted or unsubstituted heterocycloalkyl, —S(O)$_m$R$^{2E1}$ and —S(O)$_m$NR$^{2E2}$R$^{2E3}$. The symbol m represents the integers 0, 1, or 2. R$^{2E}$ and R$^{2F}$ may be joined to form a substituted or unsubstituted ring with the nitrogen to which they are attached. R$^{2E1}$, R$^{2E2}$, and R$^{2E3}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, R$^{2E2}$ and R$^{2E3}$ may be joined to form a substituted or unsubstituted ring with the nitrogen to which they are attached. In some embodiments, the substituted or unsubstituted ring formed by R$^{2E2}$ and R$^{2E3}$, and R$^{2E}$ and R$^{2F}$, may contain additional heteroatoms such as a nitrogen or oxygen (see "optionally joined together to form a ring," in the definitions section above). In addition, $R^2$ and $R^1$ may be optionally joined to form a substituted or unsubstituted ring $R^3$ is selected from substituted or unsubstituted higher alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$^{3A}$, and NR$^{3B}$R$^{3C}$. R$^{3A}$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{3B}$ and $R^{3C}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{3B}$ and $R^{3C}$ may optionally join to form a substituted or unsubstituted ring with the nitrogen to which they are attached However, $R^3$ is not lower alkyl.

$R^4$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $—S(O)_tR^{4A}$, $—S(O)_tNR^{4B}R^{4C}$, $—C(O)R^{4A}$, $—C(O)OR^{4A}$, $—C(O)NR^{4B}R^{4C}$. The symbol t represents the integers 0, 1, or 2. $R^{4A}$, $R^{4B}$, $R^{4C}$, $R^{4D}$, $R^{4E}$, and $R^{4F}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{4B}$ and $R^{4C}$ may be joined to form a substituted or unsubstituted ring with the nitrogen to which they are attached.

In some embodiments, $R^{4A}$, $R^{4B}$, $R^{4C}$, $R^{4D}$, $R^{4E}$, and $R^{4F}$ are selected from substituted or unsubstituted $(C_1-C_{10})$alkyl, substituted or unsubstituted 2-10 membered heteroalkyl, substituted or unsubstituted $(C_3-C_7)$cycloalkyl, substituted or unsubstituted 3-7 membered heterocycloalkyl, substituted or unsubstituted aryl, and substituted or unsubstituted heteroaryl.

In other embodiments, $L^2$, $L^3$ and $L^4$ are members independently selected from a bond, substituted or unsubstituted $(C_1-C_5)$alkylene, and substituted or unsubstituted 2 to 5 membered heteroalkylene. In a related embodiment, $L^2$, $L^3$ and $L^4$ are members independently selected from a bond and $—C(O)—$. In another related embodiment, $L^2$, $L^3$ and $L^4$ are members independently selected from a bond and unsubstituted $(C_1-C_5)$alkylene.

$R^1$ may be absent or is selected from hydrogen and substituted or unsubstituted alkyl. In another exemplary embodiment, $R^1$ is absent or is a member selected from hydrogen, methyl, and $—C≡C—CH_3$. In a related embodiment, $R^1$ is absent.

In an alternative group of embodiments, $R^2$ is selected from $=O$, $=N—OR^{2A}$, $—OR^{2D}$, $—NR^{2E}R^{2F}$, substituted or unsubstituted $(C_1-C_{10})$alkyl, substituted or unsubstituted 2-10 membered heteroalkyl, substituted or unsubstituted $(C_3-C_7)$cycloalkyl, substituted or unsubstituted 3-7 membered heterocycloalkyl, substituted or unsubstituted aryl, and substituted or unsubstituted heteroaryl. $R^{2A}$ and $R^{2D}$ are independently selected from hydrogen and substituted or unsubstituted $(C_1-C_{10})$alkyl. $R^{2E}$ and $R^{2F}$ are members independently selected from hydrogen and substituted or unsubstituted $(C_1-C_{10})$alkyl.

$R^2$ may also be selected from $=O$, $=N—OR^{2A}$. $R^{2A}$ and $R^{2D}$ are members selected from hydrogen and unsubstituted $(C_1-C_5)$alkyl. In a related embodiment, $R^2$ is $=O$. In another related embodiment, $R^2$ is $=O$ and the dashed line b is a bond In an exemplary embodiment, $R^3$ is selected from substituted or unsubstituted $(C_1-C_{10})$alkyl, substituted or unsubstituted 2-10 membered heteroalkyl, substituted or unsubstituted $(C_3-C_7)$cycloalkyl, substituted or unsubstituted 3-7 membered heterocycloalkyl, substituted or unsubstituted aryl, and substituted or unsubstituted heteroaryl. In a related embodiment, $R^3$ is substituted or unsubstituted benzyl.

In another group of embodiments, $R^3$ may have the formula:

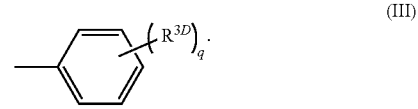

In Formula (III), q is an integer selected from 1 to 5. $R^{3D}$ is independently selected from hydrogen, halogen, $—OH$, $—COOH$, $—CF_3$, $—NH_2$, $—SH$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $—NR^{3D1}R^{3D2}$, $—OR^{3D3}$, $—C(O)NR^{3D4}R^{3D5}$, and $—C(O)R^{3D6}$.

$R^{3D1}$, $R^{3D2}$, $R^{3D3}$, $R^{3D4}$, $R^{3D5}$, and $R^{3D6}$ are members independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{3D1}$ and $R^{3D2}$ are optionally joined to form a substituted or unsubstituted ring with the nitrogen to which they are attached. $R^{3D4}$ and $R^{3D5}$ may also be optionally joined to form a substituted or unsubstituted ring with the nitrogen to which they are attached.

In a related embodiment q is an integer selected from 1 to 3, and $R^{3D}$ is independently selected from hydrogen, substituted alkyl, substituted or unsubstituted heteroalkyl, substituted cycloalkyl, substituted or unsubstituted heterocycloalkyl, substituted aryl, and substituted or unsubstituted heteroaryl.

In certain embodiments, $R^{3D}$ is independently selected from hydrogen, $R^{3D7}$-substituted $(C_1-C_{10})$alkyl, $R^{3D7}$-substituted or unsubstituted 2-10 membered heteroalkyl, $R^{3D7}$-substituted or unsubstituted $(C_3-C_8)$cycloalkyl, $R^{3D7}$-substituted or unsubstituted 3-8 membered heterocycloalkyl, $R^{3D8}$-substituted or unsubstituted aryl, $R^{3D8}$-substituted or unsubstituted heteroaryl, $—NR^{3D1}R^{3D2}$, $—OR^{3D3}$, $—C(O)NR^{3D4}R^{3D5}$, and $—C(O)R^{3D6}$.

$R^{3D1}$, $R^{3D2}$, $R^{3D3}$, $R^{3D4}$, $R^{3D5}$, and $R^{3D6}$ are independently selected from hydrogen $R^{3D7}$-substituted or unsubstituted alkyl, $R^{3D7}$-substituted or unsubstituted heteroalkyl, $R^{3D7}$-substituted or unsubstituted cycloalkyl, $R^{3D7}$-substituted or unsubstituted heterocycloalkyl, $R^{3D8}$-substituted or unsubstituted aryl, and $R^{3D8}$-substituted or unsubstituted heteroaryl. $R^{3D1}$ and $R^{3D2}$ are optionally joined with the nitrogen to which they are attached to form a $R^{3D7}$-substituted or unsubstituted heterocycloalkyl, or $R^{3D8}$-substituted or unsubstituted heteroaryl. $R^{3D4}$ and $R^{3D5}$ are optionally joined with the nitrogen to which they are attached to form a $R^{3D7}$-substituted or unsubstituted heterocycloalkyl, or $R^{3D8}$-substituted or unsubstituted heteroaryl.

$R^{3D7}$ is selected from halogen, oxo, $—OH$, $—COOH$, $—CF_3$, $—NH_2$, $—SH$, $R^{3D9}$-substituted or unsubstituted $(C_1-C_{10})$alkyl, $R^{3D9}$-substituted or unsubstituted 2-10 membered heteroalkyl, $R^{3D9}$-substituted or unsubstituted $(C_3-C_8)$cycloalkyl, $R^{3D9}$-substituted or unsubstituted 3-8 membered heterocycloalkyl, $R^{3D10}$-substituted or unsubstituted aryl, and $R^{3D10}$-substituted or unsubstituted heteroaryl. $R^{3D8}$ is selected from halogen, $—OH$, $—COOH$, $—CF_3$, $—NH_2$, $—SH$, $R^{3D9}$-substituted or unsubstituted $(C_1-C_{10})$alkyl, $R^{3D9}$-substituted or unsubstituted 2-10 membered heteroalkyl, $R^{3D9}$-substituted or unsubstituted $(C_3-C_8)$cycloalkyl, $R^{3D9}$-substituted or unsubstituted 3-8 membered heterocycloalkyl, $R^{3D10}$-substituted or unsubstituted aryl, and $R^{3D10}$-substituted or unsubstituted heteroaryl.

$R^{3D9}$ is selected from halogen, oxo, —OH, —COOH, —CF$_3$, —NH$_2$, —SH, unsubstituted $(C_1-C_{10})$alkyl, unsubstituted 2-10 membered heteroalkyl, unsubstituted $(C_3-C_8)$cycloalkyl, unsubstituted 3-8 membered heterocycloalkyl, unsubstituted aryl, and unsubstituted heteroaryl. $R^{3D10}$ is selected from halogen, —OH, —COOH, —CF$_3$, —NH$_2$, —SH, unsubstituted $(C_1-C_{10})$alkyl, unsubstituted 2-10 membered heteroalkyl, unsubstituted $(C_3-C_8)$cycloalkyl, unsubstituted 3-8 membered heterocycloalkyl, unsubstituted aryl, and unsubstituted heteroaryl.

In some embodiments, $R^{3D}$ is selected from —NR$^{3D1}$R$^{3D2}$, —OR$^{3D3}$, —C(O)NR$^{3D4}$R$^{3D5}$, and $R^{3D7}$-substituted or unsubstituted heteroaryl comprising a ring nitrogen. $R^{3D1}$ and $R^{3D2}$ may be members independently selected from hydrogen, $R^{3D7}$-substituted alkyl, $R^{3D7}$-substituted or unsubstituted heteroalkyl, $R^{3D7}$-substituted or unsubstituted heterocycloalkyl, and $R^{3D8}$-substituted or unsubstituted heteroaryl. $R^{3D1}$ and $R^{3D2}$ may be optionally joined with the nitrogen to which they are attached to form a $R^{3D7}$-substituted or unsubstituted heterocycloalkyl, or $R^{3D8}$-substituted or unsubstituted heteroaryl. In some embodiments, the ring optionally includes an additional ring heteroatom.

In certain embodiments, $R^{3D3}$, $R^{3D4}$ and $R^{3D5}$ are independently selected from hydrogen; $R^{3D7}$-substituted or unsubstituted heteroalkyl comprising a nitrogen heteroatom; $R^{3D7}$-substituted or unsubstituted heterocycloalkyl comprising a ring nitrogen; $R^{3D8}$-substituted or unsubstituted heteroaryl comprising a ring nitrogen; and alkyl substituted with a $R^{3D9}$-substituted or unsubstituted heteroalkyl comprising a nitrogen heteroatom, $R^{3D9}$-substituted or unsubstituted heterocycloalkyl comprising a ring nitrogen, or $R^{3D10}$-substituted or unsubstituted heteroaryl comprising a ring nitrogen. $R^{3D4}$ and $R^{3D5}$ may be optionally joined with the nitrogen to which they are attached to form a $R^{3D7}$-substituted or unsubstituted heterocycloalkyl, or $R^{3D8}$-substituted or unsubstituted heteroaryl. In some embodiments, the ring optionally includes a heteroatom.

In other embodiments, $R^{3D1}$ and $R^{3D2}$, and $R^{3D4}$ and $R^{3D5}$ are optionally join with the nitrogen to which they are attached to form a $R^{3D7}$-substituted or unsubstituted heterocycloalkyl comprising an additional heteroatom, or $R^{3D8}$-substituted or unsubstituted heteroaryl comprising an additional heteroatom. $R^{3D1}$ and $R^{3D2}$, and $R^{3D4}$ and $R^{3D5}$ may also be optionally joined with the nitrogen to which they are attached to form a $R^{3D8}$-substituted or unsubstituted oxazolyl, imidazolyl, thiazolyl, isooxazolyl, pyrazolyl, isothiazolyl, purinyl, pyradizinyl, pyrimidinyl, pyrazinyl, or quinoxalinyl.

$R^3$ may also have the formula:

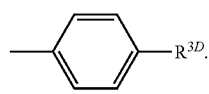

(IV)

In Formula (IV), $R^{3D}$ is selected from hydrogen, $R^{3D7}$-substituted $(C_1-C_5)$alkyl, $R^{3D7}$-substituted or unsubstituted 2-5 membered heteroalkyl, $R^{3D7}$-substituted $(C_5-C_7)$cycloalkyl, $R^{3D7}$-substituted or unsubstituted 5-7 membered heterocycloalkyl, $R^{3D8}$-substituted aryl, $R^{3D8}$-substituted or unsubstituted heteroaryl, —NR$^{3D1}$R$^{3D2}$, —OR$^{3D3}$, —C(O)NR$^{3D4}$R$^{3D5}$, and —C(O)R$^{3D6}$. $R^{3D1}$, $R^{3D2}$, $R^{3D3}$, $R^{3D4}$, $R^{3D5}$, $R^{3D6}$, $R^{3D7}$ and $R^{3D8}$ are as defined above for Formula (III). In a related embodiment, $R^{3D}$ is selected from —NR$^{3D1}$R$^{3D2}$, —OR$^{3D3}$, —C(O)NR$^{3D4}$R$^{3D5}$, and substituted or unsubstituted heteroaryl comprising a ring nitrogen. In another related embodiment, $R^{3D1}$ and $R^{3D2}$ are independently selected from hydrogen, substituted alkyl, substituted or unsubstituted heteroalkyl, substituted or unsubstituted heterocycloalkyl, and substituted or unsubstituted heteroaryl.

In one group of embodiments, $R^4$ is a member selected from substituted or unsubstituted $(C_1-C_{10})$alkyl, substituted or unsubstituted 2-10 membered heteroalkyl, substituted or unsubstituted $(C_3-C_7)$cycloalkyl, substituted or unsubstituted 3-7 membered heterocycloalkyl, substituted or unsubstituted aryl, and substituted or unsubstituted heteroaryl.

$R^4$ may also have the formula:

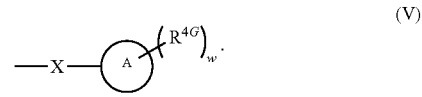

(V)

In Formula (V), $R^{4G}$ is a member independently selected from hydrogen, halogen, —OH, —COOH, —CF$_3$, —NH$_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. A is a substituted or unsubstituted ring selected from substituted or unsubstituted $(C_3-C_7)$cycloalkyl, substituted or unsubstituted 3-7 membered heterocycloalkyl, substituted or unsubstituted aryl, and substituted or unsubstituted heteroaryl. X is selected from a bond, —S(O)$_v$—, and —S(O)$_v$NR$^{4I}$—. $R^{4I}$ is a selected from hydrogen, substituted or unsubstituted alkyl, and substituted or unsubstituted heteroalkyl. The symbol v represents the integers 0, 1, or 2. The symbol w is an integer from 1 to 5. In one exemplary embodiment, X is —SO$_2$—.

In a related group of embodiments, $R^{4G}$ is selected from hydrogen, substituted $(C_1-C_5)$alkyl, substituted or unsubstituted 2-5 membered heteroalkyl, substituted $(C_5-C_7)$cycloalkyl, substituted or unsubstituted heterocycloalkyl, substituted aryl, and substituted or unsubstituted heteroaryl. A is a substituted or unsubstituted ring selected from substituted or unsubstituted 3-7 membered heterocycloalkyl, substituted or unsubstituted aryl, and substituted or unsubstituted heteroaryl. $R^{4I}$ is hydrogen. Alternatively, in a related embodiment, $R^{4G}$ may also be a branched or unbranched $(C_1-C_{10})$ alkyl.

In some embodiments, $R^{4G}$ is independently selected from hydrogen, halogen, —OH, —COOH, —CF$_3$, —NH$_2$, —SH, $R^{4G1}$-substituted or unsubstituted alkyl, $R^{4G1}$-substituted or unsubstituted heteroalkyl, $R^{4G1}$-substituted or unsubstituted cycloalkyl, $R^{4G1}$-substituted or unsubstituted heterocycloalkyl, $R^{4G2}$-substituted or unsubstituted aryl, and $R^{4G2}$-substituted or unsubstituted heteroaryl. $R^{4G1}$ is selected from halogen, oxo, —OH, —COOH, —CF$_3$, —NH$_2$, —SH, $R^{4G3}$-substituted or unsubstituted $(C_1-C_{10})$alkyl, $R^{4G3}$-substituted or unsubstituted 2-10 membered heteroalkyl, $R^{4G3}$-substituted or unsubstituted $(C_3-C_8)$cycloalkyl, $R^{4G3}$-substituted or unsubstituted 3-8 membered heterocycloalkyl, $R^{4G4}$-substituted or unsubstituted aryl, and $R^{4G4}$-substituted or unsubstituted heteroaryl. $R^{4G2}$ is selected from halogen, —OH, —COOH, —CF$_3$, —NH$_2$, —SH, $R^{4G3}$-substituted or unsubstituted $(C_1-C_{10})$alkyl, $R^{4G3}$-substituted or unsubstituted 2-10 membered heteroalkyl, $R^{4G3}$-substituted or unsubstituted $(C_3-C_8)$cycloalkyl, $R^{4G3}$-substituted or unsubstituted 3-8 membered heterocycloalkyl, $R^{4G4}$-substituted or unsubstituted aryl, and $R^{4G4}$-substituted or unsubstituted heteroaryl.

$R^{4G3}$ is selected from halogen, oxo, —OH, —COOH, —$CF_3$, —$NH_2$, —SH, unsubstituted $(C_1-C_{10})$alkyl, unsubstituted 2-10 membered heteroalkyl, unsubstituted $(C_3-C_8)$cycloalkyl, unsubstituted 3-8 membered heterocycloalkyl, unsubstituted aryl, and unsubstituted heteroaryl. $R^{4G4}$ is selected from halogen, —OH, —COOH, —$CF_3$, —$NH_2$, —SH, unsubstituted $(C_1-C_{10})$alkyl, unsubstituted 2-10 membered heteroalkyl, unsubstituted $(C_3-C_8)$cycloalkyl, unsubstituted 3-8 membered heterocycloalkyl, unsubstituted aryl, and unsubstituted heteroaryl.

In certain embodiments, A is selected from phenyl, pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, thienyl, triazinyl, thiadiazolyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, and piperazinyl.

Any combination of the embodiments described above are also within the scope of the invention. For example, in some embodiments, the dashed line b is a bond, $R^2$ is =O, $R^3$ is substituted or unsubstituted benzyl, and $R^4$ has the formula:

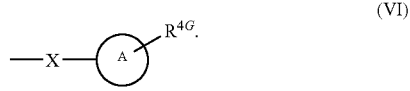

(VI)

In Formula (VI), $R^{4G}$, A and X are as described above in Formula (V). In a related embodiment, X is —$SO_2$—, $L^3$ is a bond, and $L^4$ is a bond.

In another example, the compound has the formula

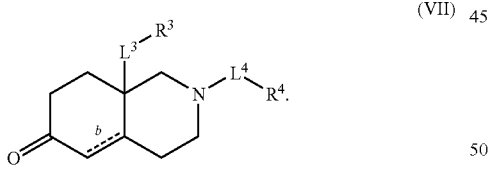

(VII)

In Formula (VII), the dashed line b, $L^3$, $R^3$, $L^4$, and $R^4$ are as described above in the description of the various embodiments of Formula (I).

Further examples of specific combinations of the embodiments described above include:

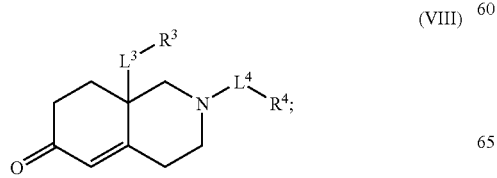

(VIII)

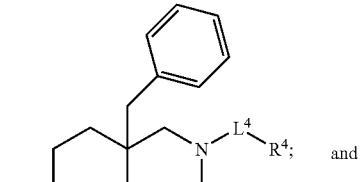

(IX)

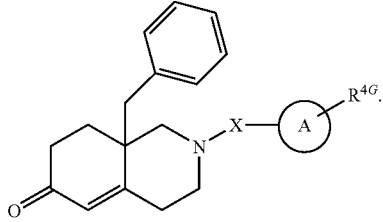

(X)

In Formula (VIII), $L^3$, $R^3$, $L^4$, and $R^4$ are as described above in the description of the various embodiments of Formula (I). In Formula (IX), $L^4$ and $R^4$ are as described above in the description of the various embodiments of Formula (I). In Formula (X), X, A, and $R^{4G}$ are as described above in the description of Formula (V).

One skilled in the art will immediately recognize that the compounds of the present invention may be in any appropriate stereochemical configuration. In an exemplary embodiment, the compound of Formula (I) has the stereochemical configuration shown below:

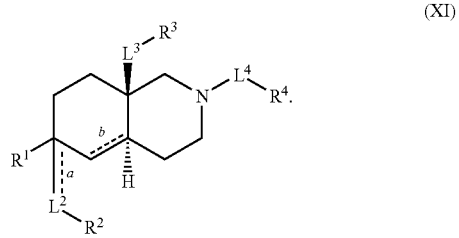

(XI)

In an alternative embodiment, the compound of Formula (I) has the stereochemical configuration shown below:

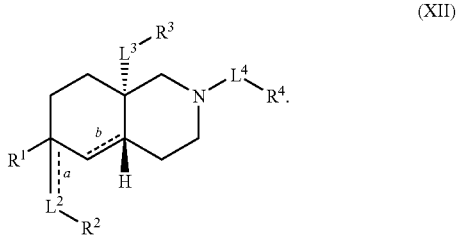

(XII)

$R^1$, $R^2$, $R^3$, $R^4$, $L^2$, $L^3$, $L^4$, a, and b in Formulae (XI) and (XII) are as defined above in the discussion of the various embodiments of Formula (I). In addition, the compounds of Formulae (VII), (VIII), (IX), and (X) may have the stereochemical configurations illustrated by Formulae (XI) and (XII).

II. Exemplary Synthesis

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. Although some compounds in Schemes I-XIII may indicate relative stereochemistry, the compounds may exist as a racemic mixture or as either enantiomer. Compounds containing the double bond in the azadecalin core are designated Series A. Ring-saturated compounds are designated Series B.

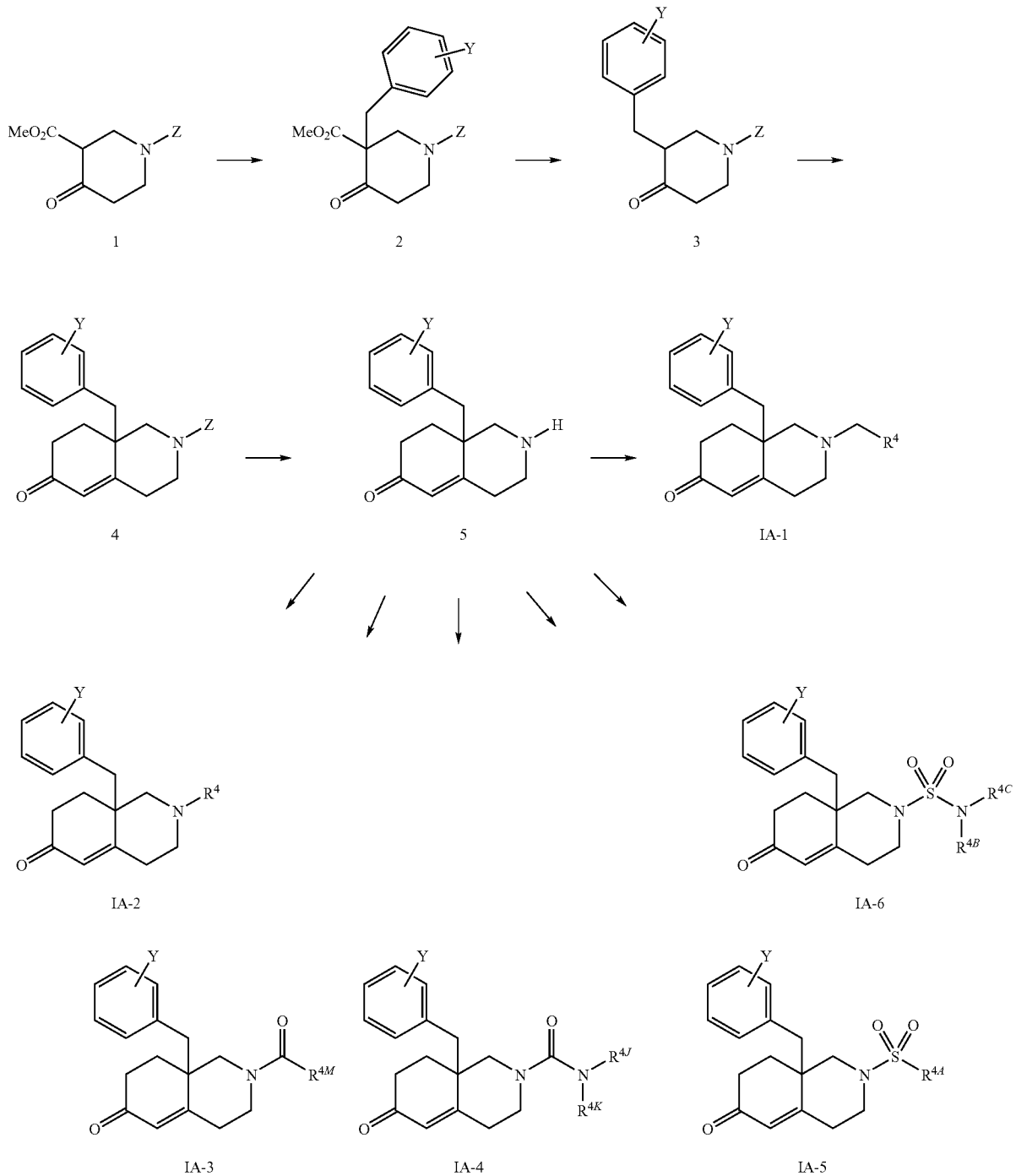

In Scheme I, $R^4$, $R^{4A}$, $R^{4B}$, and $R^{4C}$ are as defined above in the discussion of Formula (I). Y is $R^{3D}$, as defined above. $R^{4M}$, $R^{4J}$, and $R^{4K}$ are $R^{4A}$, $R^{4C}$, and $R^{4B}$, respectively, as defined above.

Compounds IA-(1-6) are prepared as illustrated in Scheme I. A suitably N-protected piperidone-2-carboxylic acid ester 1 is treated with a base such as sodium hydride, sodium ethoxide or potassium tert-butoxide in a polar solvent (e.g. N,N-dimethylformamide, ethanol, tert-butanol, dimethylsulfoxide, N-methyl-2-pyrrolidone and the like) followed by an alkylating agent to afford the alkylated keto ester 2. Suitable N-protecting groups (Z) include benzyl and carbamate groups such as tert-butoxycarbonyl (Boc) and the like. Typical alkylating agents are primary, secondary or arylalkyl halides and are preferably benzyl halides in which the aromatic ring can be substituted with a Y group (also referred to herein as $R^{3D}$, defined above).

Keto ester 2 is hydrolyzed and decarboxylated by heating in a suitable solvent such as aqueous methanol or ethanol in the presence of a strong acid (e.g. hydrochloric acid or sulfuric acid) to afford ketone 3. The reaction is typically carried out at the reflux temperature of the solvent mixture.

Ketone 3 is converted to enone 4 by a Robinson annelation reaction involving treatment of 3 with a base (e.g. potassium or sodium alkoxides) in an alcohol solvent (e.g. methanol, ethanol, or tert-butanol) followed by addition of methylvinyl ketone (MVK). The reaction is typically carried out at 0-25° C. This reaction can also be carried out with a nitrogen-containing base such as pyrrolidine, piperidine or morpholine in an aprotic solvent (e.g. benzene, toluene or dioxane) at reflux temperature followed by cooling and addition of MVK.

Enone 4 is prepared in optically active form when the nitrogen-containing base is an optical isomer of α-methylbenzylamine as described in *J. Med. Chem.* 39: 2302 (1996). Alternatively, the Robinson annelation can be carried out in an asymmetric manner with catalysis by an amino acid such as l-proline.

Removal of the N-protecting group Z from compound 4 is accomplished under standard conditions, such as treatment with a chloroformate and subsequent hydrolysis when Z is benzyl. Suitable chloroformates include methyl chloroformate, ethyl chloroformate and α-chloroethyl chloroformate. When Z is a group such as Boc, deprotection is accomplished by treatment with a strong acid such as HCl in a protic solvent (e.g., ethanol), trifluoroacetic acid, and the like.

Compound IA-1 may be prepared by alkylation of 5 with a primary or secondary alkyl, cycloalkyl, heterocycloalkyl, arylalkyl, or heteroarylalkyl halide. Alternatively, IA-1 may be prepared by reductive alkylation of 5 with the requisite aldehyde in the presence of a reducing agent such as sodium borohydride or sodium cyanoborohydride in an inert solvent (e.g. 1,2-dichloroethane).

Compound IA-2 where $R^4$ is aryl or heteroaryl may be prepared by treatment of 5 with an aryl, heteroaryl halide, or boronic acid in the presence of a copper or palladium catalyst (e.g., copper (II) acetate, palladium (II) chloride) and a base such as triethylamine.

Compound IA-3 may be prepared by acylation of 5 with a primary, secondary or tertiary alkyl, cycloalkyl, heterocycloalkyl, arylalkyl, or heteroarylalkyl carbonyl halide in a suitable protic or aprotic solvent in the presence of a base such as sodium hydroxide, triethylamine and the like. Alternatively, IA-3 may be prepared by coupling of amine 5 with the requisite carboxylic acid in the presence of a suitable coupling agent such as N,N-dicyclohexylcarbodiimide.

Compound IA-4 where $R^{4K}$ is hydrogen may be prepared by treatment of 5 with a primary, secondary or tertiary alkyl, cycloalkyl, heterocycloalkyl, arylalkyl, or heteroarylalkyl isocyanate in an inert solvent (e.g. toluene, dichloromethane, 1,2-dichloroethane or dioxane). When $R^{4K}$ is a group other than hydrogen, compound IA-4 may be prepared by treatment of 5 with the carbamoyl halide $R^{4J}R^{4K}NC(O)X$ (where X is Cl, Br, F) in an inert solvent (e.g. toluene, dichloromethane, 1,2-dichloroethane or dioxane) in the presence of a base such as triethylamine.

Compound IA-5 is prepared by treatment of 5 with a primary, secondary or tertiary alkyl, cycloalkyl, heterocycloalkyl, arylalkyl, or heteroarylalkyl sulfonyl halide in an inert solvent (e.g. toluene, dichloromethane, 1,2-dichloroethane or dioxane) in the presence of a base such as triethylamine.

Compound IA-6 is prepared by treatment of 5 with the sulfamoyl halide $R^{4B}R^{4C}NSO_2X$ (where X is Cl, Br, or F) in an inert solvent (e.g. toluene, dichloromethane, 1,2-dichloroethane or dioxane) in the presence of a base such as triethylamine.

Scheme II

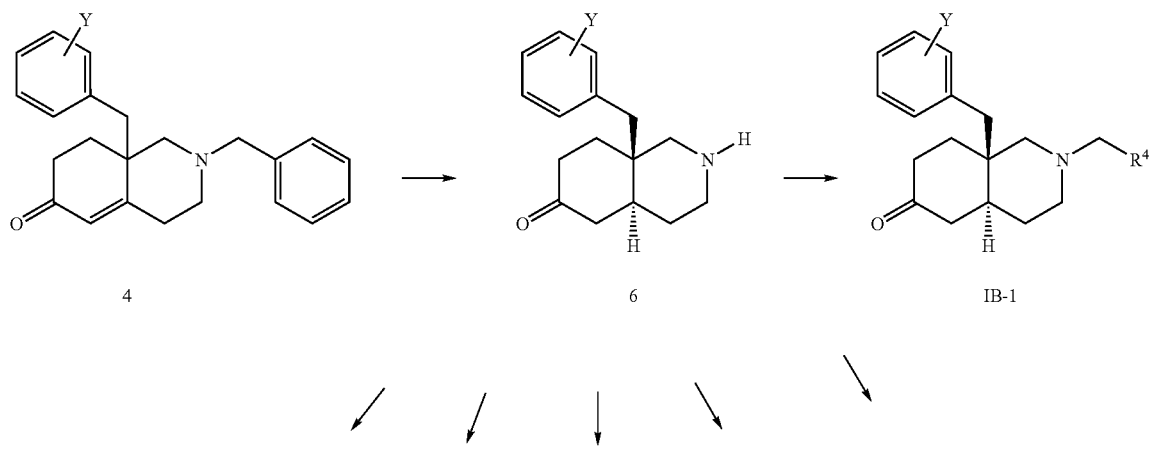

-continued

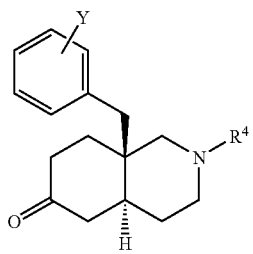

IB-2

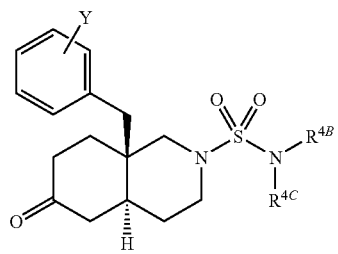

IB-6

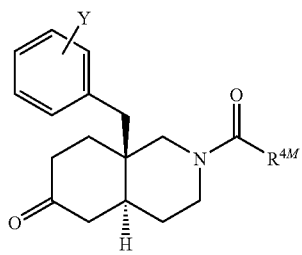

IB-3

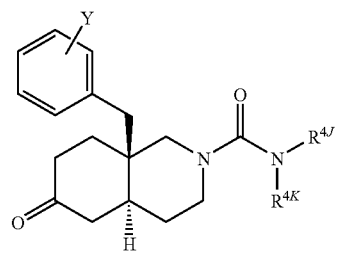

IB-4

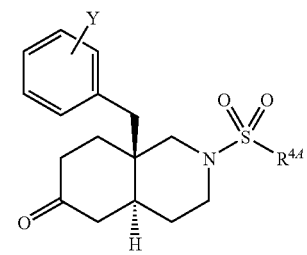

IB-5

In Scheme II, $R^4$, $R^{4A}$, $R^{4B}$, $R^{4C}$, Y, $R^{4M}$, $R^{4J}$, and $R^{4K}$ are as defined above in Scheme I.

Compounds IB-(1-6) are similarly prepared from saturated ketone 6 (Scheme II) according to the reactions previously described in Scheme I. One of skilled in the art will immediately recognize that compound 6 can exist as the cis or trans isomer. Scheme II exemplifies the preparation of the trans isomers of compound IB. However, the reaction scheme is equally applicable to the preparation of the corresponding cis isomers.

Compounds IA-7,8 are prepared by treatment of IA with a reducing agent (e.g. sodium borohydride) in an alcohol solvent (e.g. ethanol); or with lithium aluminum hydride, diisobutylaluminum hydride, and the like, in an inert solvent (e.g. tetrahydrofuran or toluene). Depending on the specific reducing agent, various ratios of the diastereomeric alcohols IA-7 and IA-8 are obtained (Scheme III).

Scheme III

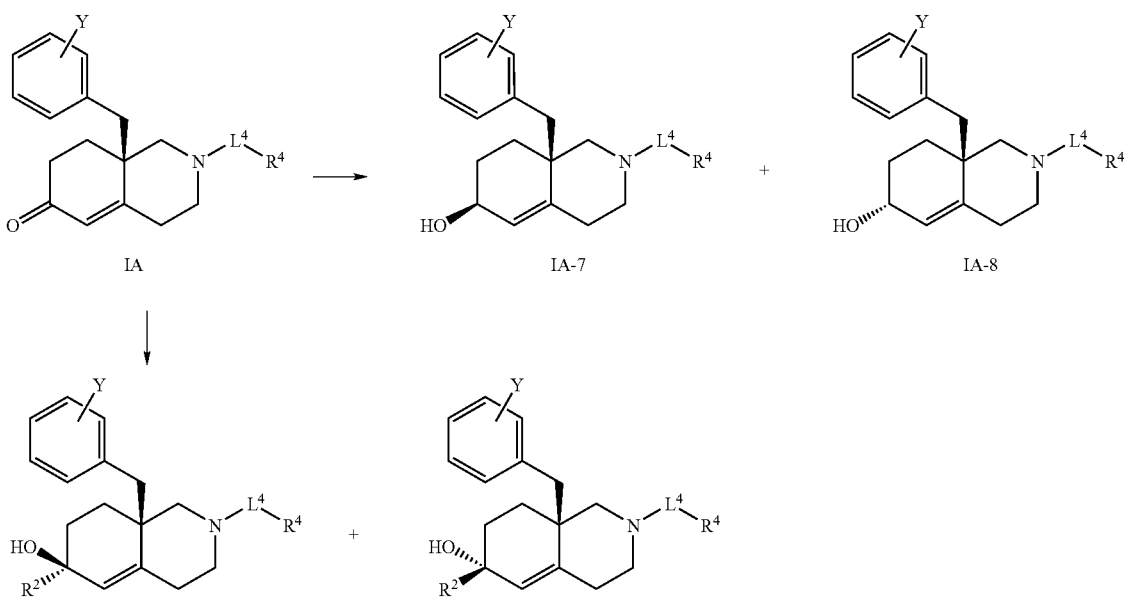

In Scheme III, $L^4$, $R^4$, and $R^2$ are as defined in the discussion of Formula (I) above. Y is as defined in Scheme I.

Proceeding in the same manner, alcohols IB-7 and IB-8 may also be obtained from IB (Scheme IV).

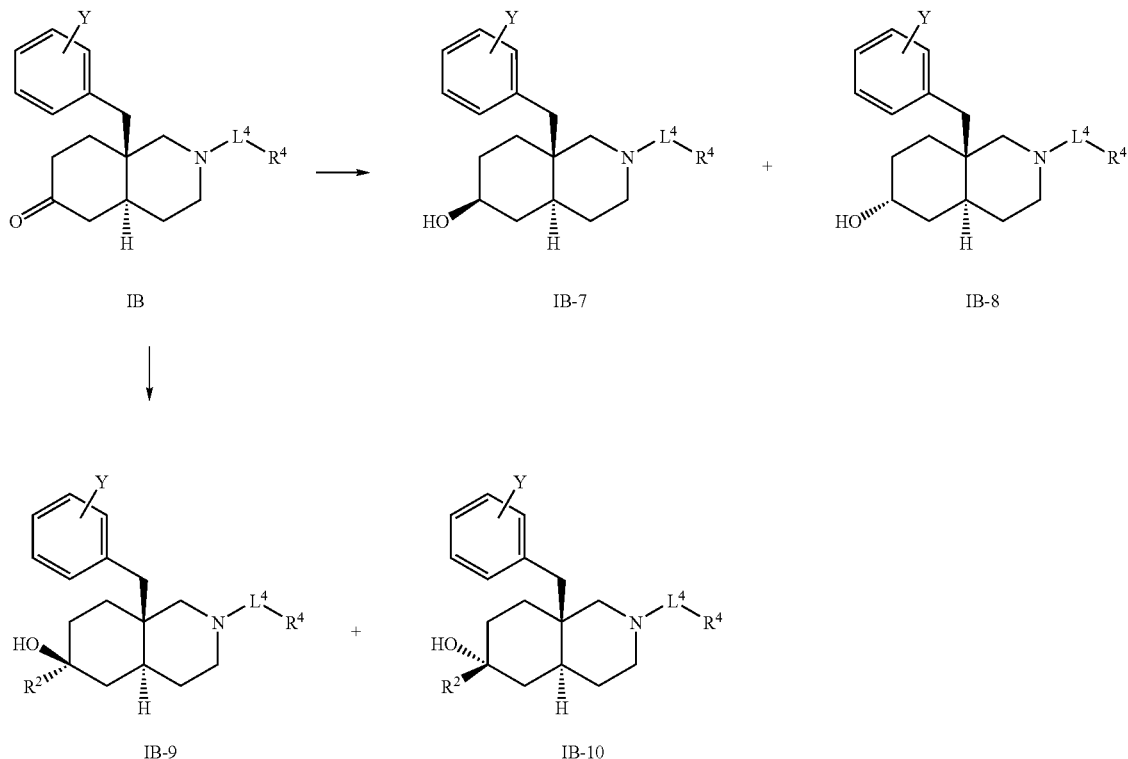

In Scheme IV, $L^4$, $R^4$, and $R^2$ are as defined in the discussion of Formula (I) above. Y is as defined in Scheme I.

Treatment of IA or IB with an organometallic reagent such as a Grignard reagent or an organolithium affords tertiary alcohols IA-9 and IA-10 (Scheme III) or alcohols IB-9 and IB-10 (Scheme IV). The reaction is carried out in an inert solvent such as tetrahydrofuran or dioxane.

If produced as mixtures, isomers IA-7,8 and IA-9,10 (Scheme III) and IB-7,8 and IB-9,10 (Scheme IV) can be separated by means well-known in the art such as chromatography or crystallization.

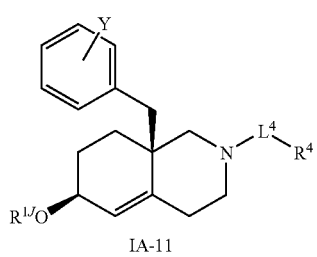

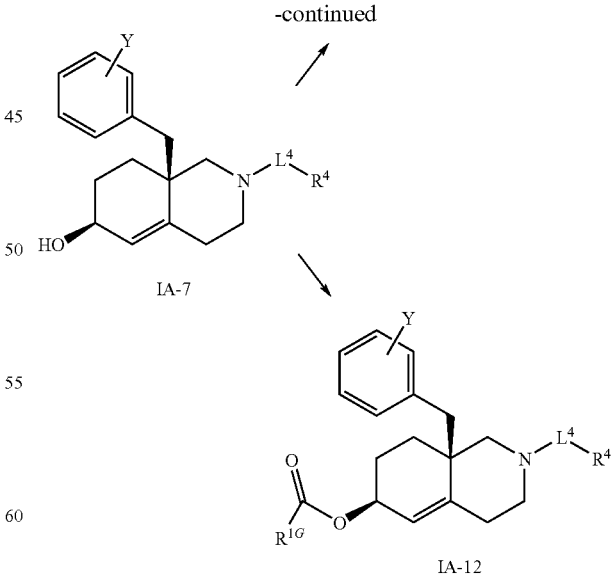

In Scheme V, $L^4$ and $R^4$ are as defined in the discussion of Formula (I) above. Y is as defined in Scheme I. $R^{1G}$ and $R^{1J}$ are equivalent to $R^{2D}$, as defined above.

Alcohols IA-7,8 are converted into substituted derivatives by treatment with a base (e.g. sodium hydride) in an aprotic solvent (e.g. tetrahydrofuran, N,N-dimethylformamide) followed by addition of a hydrogen, substituted or unsubstituted alkyl, substituted or unsubstituted heteroalkyl, substituted or unsubstituted aryl, or substituted or unsubstituted heterocyclylalkylhalide, as illustrated by the formation of IA-11 from IA-7 in Scheme V. Similarly, acyl derivatives such as IA-12 can be formed by treatment of 1A-7 with the requisite acyl halide, anhydride, chloroformate, isocyanate or carbamoyl halide in an aprotic solvent (e.g., tetrahydrofuran, N,N-dimethylformamide and the like) in the presence of a base (e.g., triethylamine and the like). Ring saturated derivatives such as IB-13,14 are similarly prepared from IB-7 (Scheme VI).

by treatment of IB with the amino component and a reducing agent (e.g. hydrogen, sodium borohydride or sodium cyanoborohydride) in a solvent such as tetrahydrofuran, ethanol, 1,2-dichloroethane and the like. Depending on the specific reducing agent and reaction conditions, various ratios of the diastereomeric amines IB-13,14 and IA-15,16 are obtained (Scheme VII). If produced as mixtures, isomers IB-13,14 and IB-15,16 may be separated by means well-known in the art (e.g. chromatography, crystallization or formation of an acid-salt followed by selective crystallization).

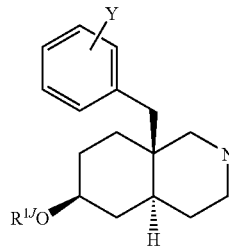

In Scheme VI, $L^4$, $R^4$, Y, $R^{1G}$ and $R^{1J}$ are as defined in Scheme V above.

Compounds IB-13,14 and IB-15,16 (Scheme VII) in which $R^{1G}$ and $R^{1J}$ are hydrogen, substituted or unsubstituted alkyl, substituted or unsubstituted cycloalkyl, substituted or unsubstituted heterocyclolalkyl, substituted or unsubstituted arylalkyl, or substituted or unsubstituted heteroarylalkyl are prepared by reductive amination of ketone IB with ammonia, a secondary amine, or tertiary amine. The reaction is carried out

27

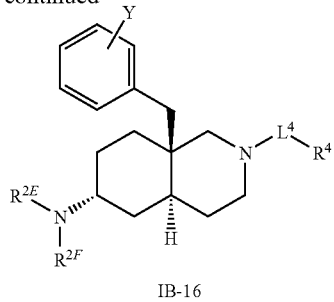

IB-16

In Scheme VII, $R^{2E}$ and $R^{2F}$ are as defined in the discussion of Formula (I) above. Y is as defined in Scheme I above.

Compounds IB-13,14 in which $R^{2E}$ is —C(O)$R^{2K}$ are prepared by amination of IB with ammonia as described above, followed by acylation with a primary, secondary or tertiary alkyl, cycloalkyl, heterocycloalkyl, arylalkyl, or heteroarylalkyl carbonyl halide in a suitable protic or aprotic solvent in the presence of a base (e.g. sodium hydroxide, triethylamine and the like). In Scheme VII, $R^{2K}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Alternatively, IB-13,14 may be prepared by coupling of amine 5 with the requisite carboxylic acid in the presence of a suitable coupling agent such as N,N-dicyclohexylcarbodiimide and the like. Compounds IB-15,16 in which $R^{2E}$ is C(O)$R^{2K}$ are similarly prepared by acylation of IB-13,14.

Compounds IB-13,14 in which $R^{2E}$ is —C(O)N$R^{2M}R^{2N}$ are prepared by amination of IB with ammonia as described above, followed by treatment with a primary, secondary or tertiary alkyl, cycloalkyl, heterocycloalkyl, arylalkyl, or heteroarylalkyl isocyanate in an inert solvent such as toluene, dichloromethane, 1,2-dichloroethane or dioxane. $R^{2M}$ and $R^{2N}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{2M}$ and $R^{2N}$ may be combined with the nitrogen to which they are joined to from a substituted or unsubstituted ring.

When $R^{2M}$ is a group other than hydrogen, compounds IB-13,14 are prepared by treatment of IB-13,14 (where $R^{2M}$ is hydrogen) with the carbamoyl halide $R^{2M}R^{2N}$NCOX (X=Cl, Br, F) in an inert solvent (e.g. toluene, dichloromethane, 1,2-dichloroethane or dioxane) in the presence of a base such as triethylamine. Compounds IB-15,16 in which $R^{2F}$ is —C(O)N$R^{1A}R^{1E}$ are similarly prepared from IB-13,14.

Compounds IB-13,14 in which $R^{2E}$ is —SO$_2R^{2E1}$ are prepared by amination of IB with ammonia as described above, followed by treatment with a primary, secondary or tertiary alkyl, cycloalkyl, heterocycloalkyl, arylalkyl, or heteroarylalkyl sulfonyl halide in an inert solvent such as toluene, dichloromethane, 1,2-dichloroethane or dioxane in the presence of a base such as triethylamine. Compounds IB-15,16 in which

28

$R^{2F}$ is —SO$_2R^{2E1}$ are similarly prepared from IB-13,14. $R^{2E1}$ is as defined in Formula (I) above.

Compounds IB-13,14 in which $R^{2E}$ is —SO$_2R^{2E2}R^{2E3}$ are prepared by amination of IB with ammonia as described above, followed by treatment with the sulfamoyl halide $R^4R^{7A}$NSO$_2$X (where X is Cl, Br, F) in an inert solvent (e.g. toluene, dichloromethane, 1,2-dichloroethane or dioxane) in the presence of a base such as triethylamine. $R^{2E2}$ and $R^{2E3}$ are as defined in Formula (I) above.

Oximino compounds IA-17 and IB-17 (Scheme VIII) are prepared from IA and IB, respectively, by treatment with a hydroxylamine $R^{2A}$ONH$_2$ in a protic or aprotic solvent such as ethanol, N,N-dimethylformamide and the like. The oximino compounds IA-17 and IB-17 can be formed as mixtures of E and Z isomers which can be separated by conventional means such as chromatography or crystallization.

Scheme VIII

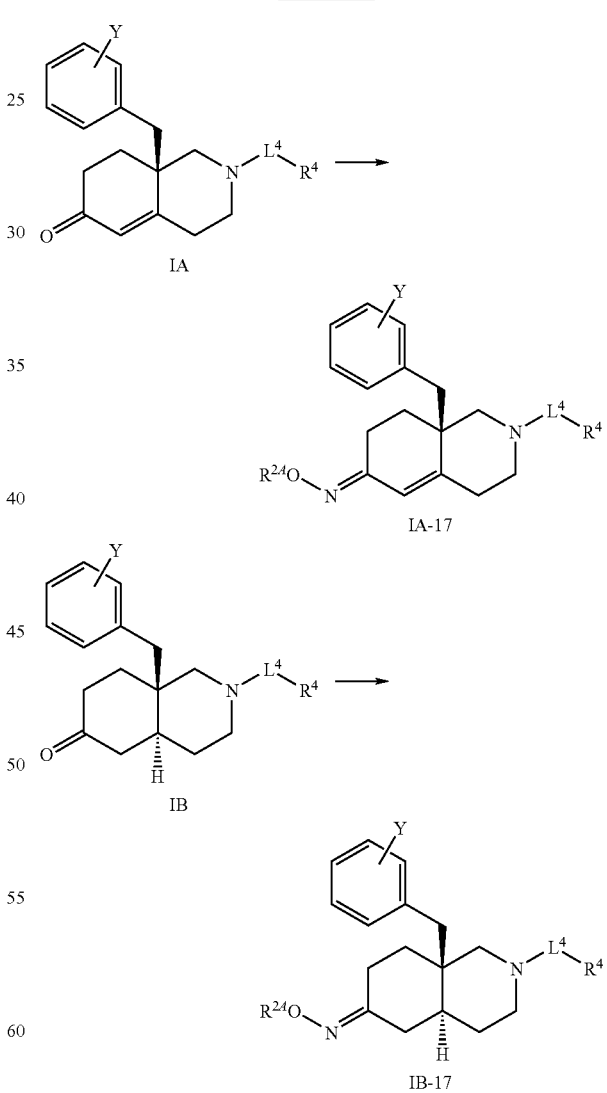

In Scheme VIII, $L^4$, $R^4$ and $R^{2A}$ are as defined in the discussion of Formula (I) above. Y is as defined in Scheme 1 above.

Compound IB-18 are prepared as shown in Scheme IX. Ketone IB can be homologated to ester 8 and acid 9 by various means well known in the art. For example, treatment of IB with trimethysilyldithiane in the presence of a strong base such as n-butyllithium and the like in an aprotic solvent such as tetrahydrofuran affords intermediate 7. Hydrolysis of 7 to ester 8 is effected by treatment with mercury (II)chloride and a strong acid such as perchloric acid in a protic solvent such as methanol. Compound IB-18 in which $R^{2D1}$ is substituted or unsubstituted alkyl, substituted or unsubstituted heterocycloalkyl, substituted or unsubstituted aryl or substituted or unsubstituted heteroaryl are prepared by treatment of 8 with the corresponding organometallic reagent such as a Grignard reagent or an organolithium reagent. Compound IB-18 in which $R^{2D1}$ is substituted or unsubstituted alkylamino, substituted or unsubstituted heterocycloalkylamino, substituted or unsubstituted arylamino or substituted or unsubstituted heteroarylamino are prepared by treatment of 8 with the corresponding primary, secondary or tertiary amine in the presence or absence of a suitable polar solvent such as ethanol, N,N-dimethylformamide and the like. Alternatively, the amine may be activated by reaction with a trialkylaluminum reagent such as trimethylaluminum prior to reaction with ester 8. Ester 8 may also be hydrolyzed to acid 9 by conventional means (e.g. treatment with sodium hydroxide in an aqueous solvent mixture), then coupled with the requisite amine by means well-known in the art (e.g. conversion to the acid chloride followed by treatment with the amine, the use of a coupling reagent such as N,N-dicyclohexylcarbodiimide, and the like).

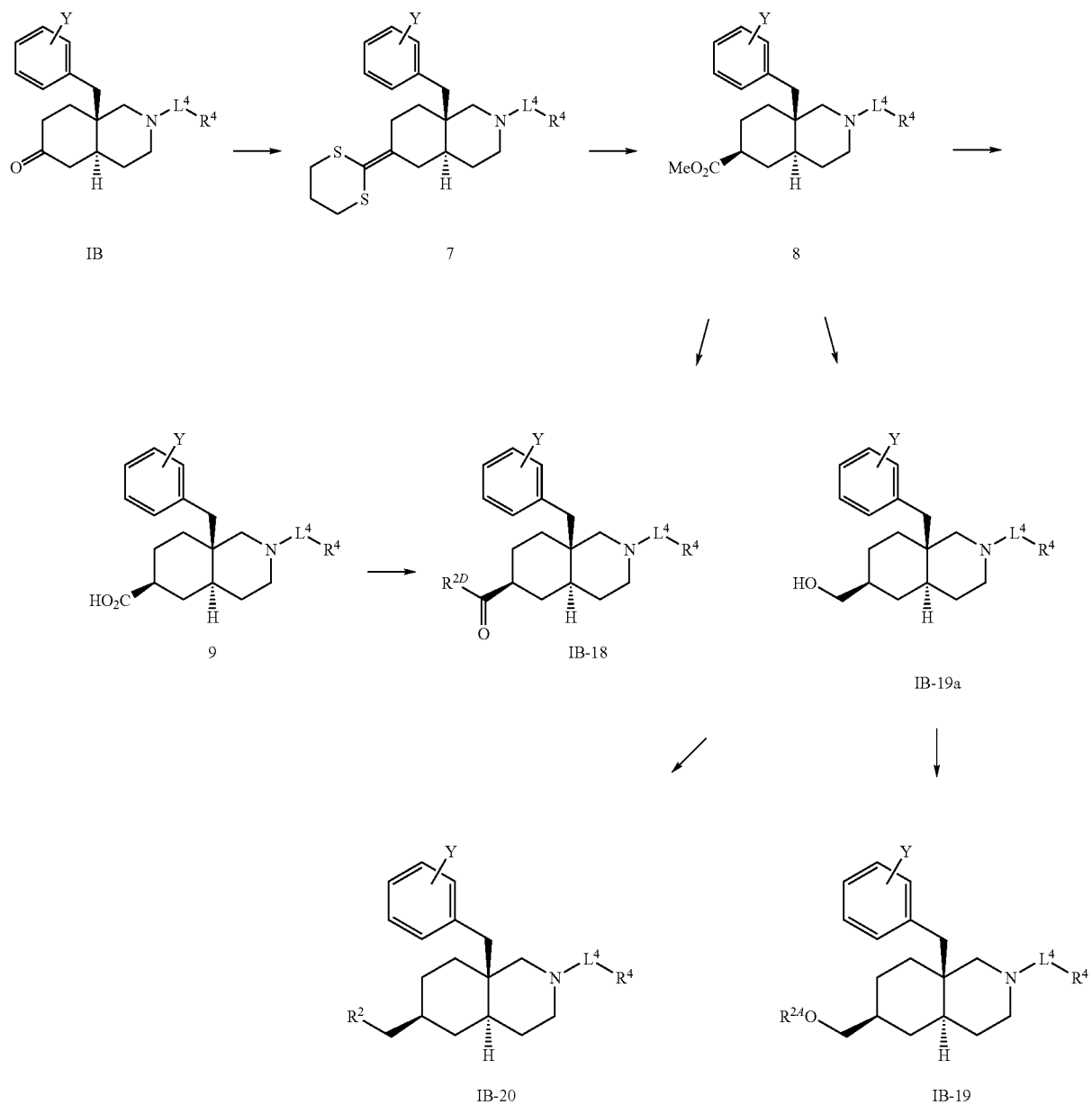

In Scheme IX, Y is as defined in Scheme I. $R^2$, $R^{2A}$, $R^{2D}$, $L^4$ and $L^5$ are as defined in the discussion of Formula (I) above.

Compounds IB-19 and IB-20 are prepared from ester 8 by reduction to the corresponding alcohol IB-19a by treatment of 8 with a reducing agent (e.g. sodium borohydride) in an alcohol solvent (e.g. ethanol); or with lithium aluminum hydride, diisobutylaluminum hydride, and the like, in an inert solvent (e.g. tetrahydrofuran or toluene). Conversion of alcohol IB-19a to IB-19 and IB-20 is effected as previously described for the conversion of IA-7 to IA-11,12 and of IB-7 to IB-11,12 in Schemes V and VI.

Compounds IB-21,22 are analogously prepared as shown in Scheme X. Ketone IB is converted to the unsaturated ester 10 by a Wittig or Horner-Emmons reaction, which are well known in the art. For example, treatment of IB with triethyl phosphonoacetate in the presence of sodium hydride in tetrahydrofuran affords the ester 10 as a mixture of E and Z isomers (indicated by the wavy line). Reduction to 11 is effected by catalytic hydrogenation using a catalyst such as platinum (II)oxide or palladium on carbon in a solvent such as ethyl acetate or ethanol. Ester 11 may be obtained as a mixture of diastereomers, the ratio of which is dependent on the reaction conditions. Conversion of 11 to IB-21 and IB-22 is carried out analogously to the conversion of 8 to 9 and IB-18, 19,20 in Scheme IX.

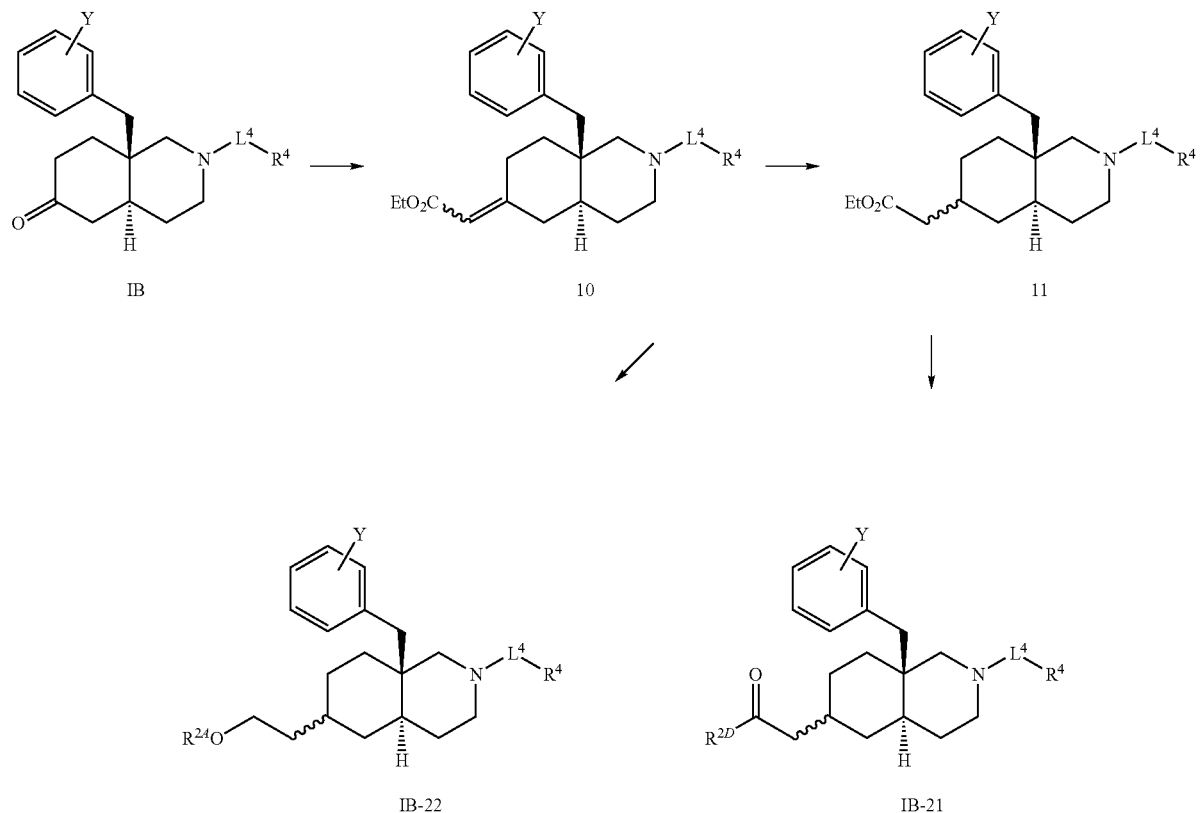

Scheme X

In Scheme X, $R^{2A}$, $R^{2D}$, $L^4$ and $R^4$ are as defined in the discussion of Formula (I) and Y is as defined in Scheme II.

The group Y in compounds IA and IB can be modified subsequent to synthesis of the compounds according to Schemes I and II, as exemplified in Scheme XI. Thus, a brominated derivative, such as IA-(1-5) where Y is 4-Br, can be converted to an amino derivative by conversion to the (bis-pinacolato)diboron derivative followed by copper-catalyzed amination. Similarly, the bromo derivative may be converted to aryl ethers by metal-catalyzed ether formation or to amide derivatives by palladium-catalyzed carbonylation/amidation procedures. Derivatives in which Y is heteroaryl can be prepared by treatment of IA-(1-5) where Y is 4-Br with a heteroarylboronic acid in the presence of a palladium catalyst.

Scheme XI
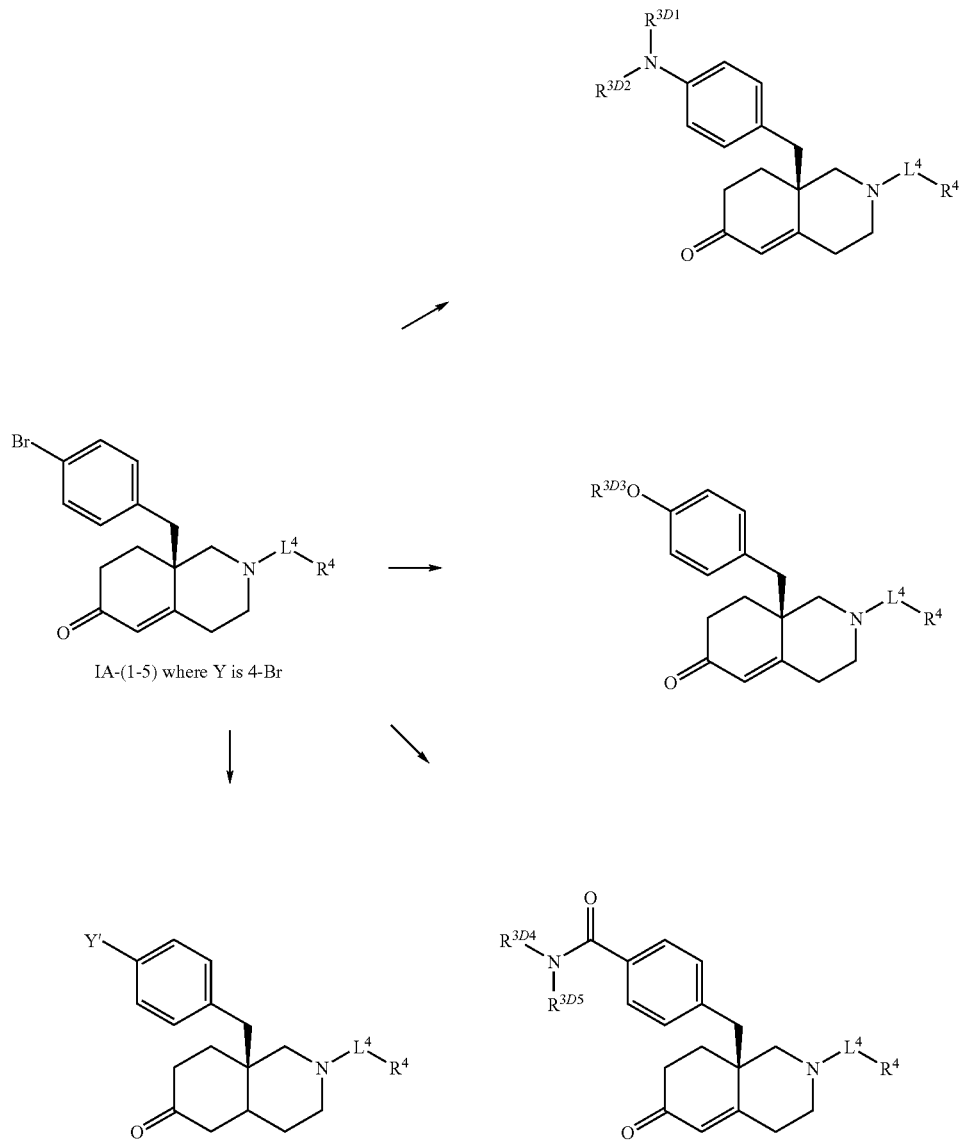
In Scheme XI, Y' is heteroaryl and $R^{3D1}$, $R^{3D2}$, $R^{3D3}$, $R^{3D4}$, $R^{3D5}$, $L^4$, and $R^4$ are as defined above in the discussion of Formula (I).
Scheme XII
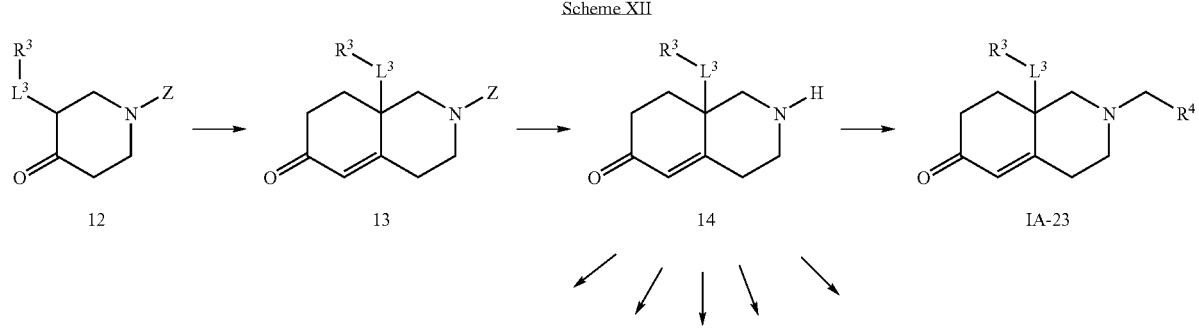

-continued

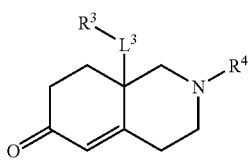
IA-24

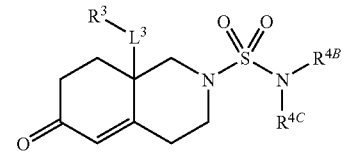
IA-28

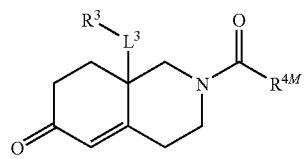
IA-25

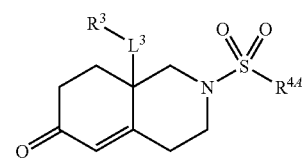
IA-27

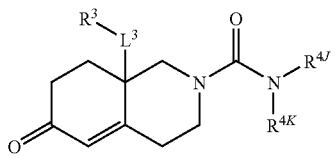
IA-26

Compounds IA-(23-28) are prepared as illustrated in Scheme XII. $L^3$, $R^3$, $R^{4B}$, and $R^{4C}$ are as defined in Formula (I) above. $R^{4K}$, $R^{4J}$, and $R^{4M}$, are as defined in Scheme I above.

Ketone 12 is converted to enone 13 by a Robinson annelation reaction involving treatment of 12 with a base (e.g. potassium or sodium alkoxides) in an alcohol solvent (e.g. methanol, ethanol, or tert-butanol) followed by addition of methylvinyl ketone (MVK). The reaction is typically carried out at 0-25° C. This reaction can also be carried out with a nitrogen-containing base such as pyrrolidine, piperidine or morpholine in an aprotic solvent (e.g. benzene, toluene or dioxane) at reflux temperature followed by cooling and addition of MVK.

Enone 13 can be prepared in racemic form by treatment of 12 with methylvinyl ketone and base. Compound 13 ($L^3$=CO, $R^3$=OMe, Z=Boc) can be prepared in optically active form as described in *Org. Lett.* 6, 1171 (2004). Removal of the N-protecting group Z from compound 13 is accomplished under standard conditions, such as treatment with a chloroformate and subsequent hydrolysis when Z is benzyl. Suitable chloroformates include methyl chloroformate, ethyl chloroformate and α-chloroethyl chloroformate. When Z is a group such as Boc, deprotection is accomplished by treatment with a strong acid such as HCl in a protic solvent (e.g., ethanol) or with trifluoroacetic acid, and the like.

Compound IA-23 may be prepared by alkylation of 14 with a primary or secondary alkyl, cycloalkyl, heterocycloalkyl, arylalkyl, or heteroarylalkyl halide. Alternatively, IA-23 may be prepared by reductive alkylation of 14 with the requisite aldehyde in the presence of a reducing agent such as sodium borohydride or sodium cyanoborohydride in an inert solvent (e.g. 1,2-dichloroethane).

Compound IA-24 where $R^4$ is aryl or heteroaryl may be prepared by treatment of 14 with an aryl, heteroaryl halide, or boronic acid in the presence of a copper or palladium catalyst (e.g., copper (II) acetate, palladium (II) chloride) and a base such as triethylamine.

Compound IA-25 may be prepared by acylation of 14 with a primary, secondary or tertiary alkyl, cycloalkyl, heterocycloalkyl, arylalkyl, or heteroarylalkyl carbonyl halide in a suitable protic or aprotic solvent in the presence of a base such as sodium hydroxide, triethylamine and the like. Alternatively, IA-25 may be prepared by coupling of amine 14 with the requisite carboxylic acid in the presence of a suitable coupling agent such as N,N-dicyclohexylcarbodiimide.

Compound IA-26 where $R^{4K}$ its hydrogen may be prepared by treatment of 14 with a primary, secondary or tertiary alkyl, cycloalkyl, heterocycloalkyl, arylalkyl, or heteroarylalkyl isocyanate in an inert solvent (e.g. toluene, dichloromethane, 1,2-dichloroethane or dioxane). When $R^{4K}$ is a group other than hydrogen, compound IA-26 may be prepared by treatment of 14 with the carbamoyl halide $R^{4J}R^{4K}NC(O)X$ (where X is Cl, Br, P) in an inert solvent (e.g. toluene, dichloromethane, 1,2-dichloroethane or dioxane) in the presence of a base such as triethylamine.

Compound IA-27 is prepared by treatment of 14 with a primary, secondary or tertiary alkyl, cycloalkyl, heterocycloalkyl, arylalkyl, or heteroarylalkyl sulfonyl halide in an inert solvent (e.g. toluene, dichloromethane, 1,2-dichloroethane or dioxane) in the presence of a base such as triethylamine.

Compound IA-28 is prepared by treatment of 14 with the sulfamoyl halide $R^{4B}R^{4C}NSO_2X$ (where X is Cl, Br, or F) in an inert solvent (e.g. toluene, dichloromethane, 1,2-dichloroethane or dioxane) in the presence of a base such as triethylamine.

These compounds IA-(23-28) could be further derivatized as depicted in scheme XIII.

Scheme XIII

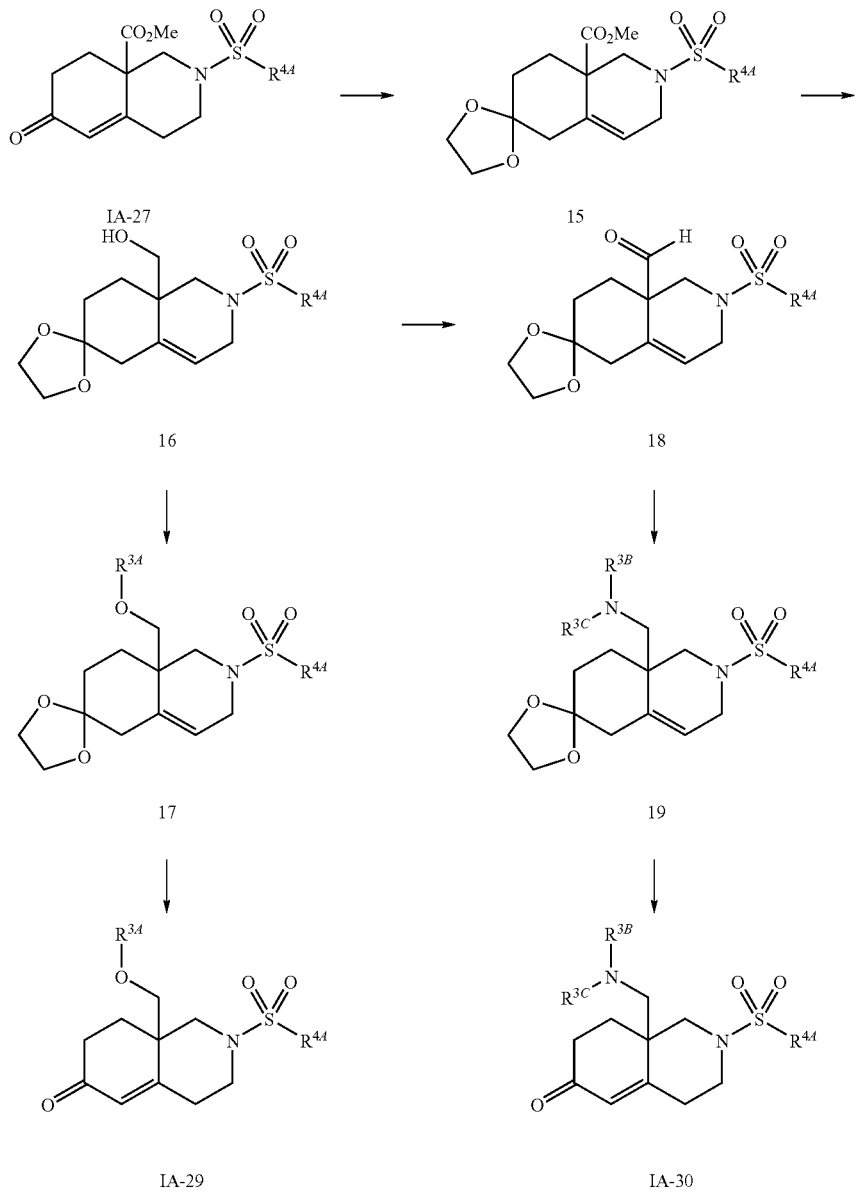

In Scheme XIII, $R^{3A}$, $R^{3B}$, $R^{3C}$, $R^{4A}$ is as defined in Formula (I) above.

Compound 15 is prepared by treatment of IA-27 with ethylene glycol in an aprotic solvent (e.g. dimethoxyethanol, benzene, chloroform) in the presence of an acid (such as hydrochloric acid or p-toluenesulfonic acid).

Compounds of the type 16 are prepared from ester 15 by reduction to the corresponding alcohol by treatment with a reducing agent (e.g. sodium borohydride) in an alcohol solvent (e.g. ethanol); or with lithium aluminum hydride, diisobutylaluminum hydride, and the like, in an inert solvent (e.g. tetrahydrofuran or toluene).

Alcohols 16 are converted into substituted derivatives 17 by treatment with a base (e.g. sodium hydride) in an aprotic solvent (e.g. tetrahydrofuran, N,N-dimethylformamide) followed by addition of a hydrogen, substituted or unsubstituted alkylhalide, substituted or unsubstituted heteroalkylhalide, substituted or unsubstituted arylhalide, or substituted or unsubstituted heterocycylalkylhalide.

Compounds of the type IA-29 are prepared from 17 by treatment with an acid (e.g. p-toluenesulfonic acid, hydrochloric acid or acetic acid) in a polar solvent (e.g. acetone, water); or with perchloric acid in an inert solvent (e.g. dichloromethane).

Compounds of the type 18 are prepared from alcohols 16 by oxidation to the corresponding aldehyde by treatment with an oxidizing agent (e.g. chromium(VI) reagents such as pyridinium chlorochromate and pyridinium dichromate) in an aprotic solvent (e.g. dichloromethane), or using the Swern oxidation method (oxalyl chloride and dimethyl sulfoxide followed by addition of an organic base such as triethylamine).

Compound 19 (Scheme XIII) in which $R^{3B,C}$ are hydrogen, substituted or unsubstituted alkyl, substituted or unsubstituted cycloalkyl, substituted or unsubstituted heterocyclolalkyl, substituted or unsubstituted arylalkyl, or substituted or unsubstituted heteroarylalkyl are prepared by reductive amination of aldehyde 18 with ammonia, a secondary amine, or tertiary amine. The reaction is carried out by treatment of 18 with the amino component and a reducing agent (e.g. hydrogen, sodium borohydride or sodium cyanoborohydride) in a solvent such as tetrahydrofuran, ethanol, 1,2-dichloroethane and the like.

Compounds of the type IA-30 are prepared from 19 by treatment with an acid (e.g. p-toluenesulfonic acid, hydrochloric acid and acetic acid) in a polar solvent (e.g. acetone, water); or with perchloric acid in an inert solvent (e.g. dichloromethane).

III. Assays and Methods for Modulating Glucocorticoid Receptor Activity

The compounds of the present invention can be tested for their antiglucocorticoid properties. Methods of assaying compounds capable of modulating glucocorticoids receptor activity are presented herein. Typically, compounds of the current invention that are capable of modulating glucocorticoid receptor activity by selectively binding to the GR or by preventing GR ligands from binding to the GR. In some embodiments, the compounds exhibit little or no cytotoxic effect. Therefore, exemplary assays disclosed herein may test the ability of compounds to (1) tightly bind to the GR; (2) selectively bind to the GR; (3) prevent GR ligands from binding to the GR; (4) modulate the activity of the GR in a cellular system; and/or (5) exhibit non-cytotoxic effects.

Binding Assays

In some embodiments, GR modulators are identified by screening for molecules that compete with a ligand of GR, such as dexamethasone. Those of skill in the art will recognize that there are a number of ways to perform competitive binding assays. In some embodiments, GR is pre-incubated with a labeled GR ligand and then contacted with a test compound. This type of competitive binding assay may also be referred to herein as a binding displacement assay. Alteration (e.g., a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3$H, $^{125}$I, $^{35}$S, $^{14}$C, or $^{32}$P. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

For competitive binding assays, the amount of inhibition may be determined using the techniques disclosed herein. The amount of inhibition of ligand binding by a test compound depends on the assay conditions and on the concentrations of ligand, labeled analyte, and test compound that are used. In an exemplary embodiment, a compound is said to be capable of inhibiting the binding of a GR ligand to a GR in a competitive binding assay if the inhibition constant ($K_i$) is less than 5 µM using the assay conditions presented in Example 31. In another exemplary embodiment, a compound is said to be capable of inhibiting the binding of a GR ligand to a GR in a competitive binding assay if the $K_i$ is less than 1 µM using the assay conditions presented in Example 31. In another exemplary embodiment, a compound is said to be capable of inhibiting the binding of a GR ligand to a GR in a competitive binding assay if the $K_i$ is less than 100 nM using the assay conditions presented in Example 31. In another exemplary embodiment, a compound is said to be capable of inhibiting the binding of a GR ligand to a GR in a competitive binding assay if the $K_i$ is less than 100 nM using the assay conditions presented in Example 31. In another exemplary embodiment, a compound is said to be capable of inhibiting the binding of a GR ligand to a GR in a competitive binding assay if the $K_i$ is less than 100 pM using the assay conditions presented in Example 31. In another exemplary embodiment, a compound is said to be capable of inhibiting the binding of a GR ligand to a GR in a competitive binding assay if the $K_i$ is less than 10 pM using the assay conditions presented in Example 31.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR. Typically, ligand-binding fragments will comprise transmembrane regions and/or most or all of the extracellular domains of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which sexhibit glucocorticoid mediated upregulation of PEPCK and glucose-6-phosphate (G-6-Pase)). GRE-mediated gene expression has also been demonstrated in transfected cell lines using well-known GRE-regulated sequences (e.g. the mouse mammary tumour virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); or expression of genes regulated by NFkB or AP-1 transcription factors in transfected cell-lines. An example of a cell-based assay measuring gene transcription is presented in Example 33.

Typically, compounds that are tested in whole-cell assays are also tested in a cytotoxicity assay. Cytotoxicity assays are used to determine the extent to which a perceived modulating effect is due to non-GR binding cellular effects. In an exemplary embodiment, the cytotoxicity assay includes contacting a constitutively active cell with the test compound. Any decrease in cellular activity indicates a cytotoxic effect. An exemplary cytotoxicity assay is presented in Example 34.

Specificity

The compounds of the present invention may be subject to a specificity assay (also referred to herein as a selectivity assay). Typically, specificity assays include testing a compound that binds GR in vitro or in a cell-based assay for the degree of binding to non-GR proteins. Selectivity assays may be performed in vitro or in cell based systems, as described above. GR binding may be tested against any appropriate non-GR protein, including antibodies, receptors, enzymes, and the like. In an exemplary embodiment, the non-GR binding protein is a cell-surface receptor or nuclear receptor. In another exemplary embodiment, the non-GR protein is a steroid receptor, such as estrogen receptor, progesterone receptor, androgen receptor, or mineralocorticoid receptor. An exemplary specificity assay is presented in Example 34.

Methods of Modulating GR Activity

In another aspect, the present invention provides methods of modulating glucocorticoid receptor activity using the techniques described above. In an exemplary embodiment, the method includes contacting a GR with a compound of the present invention, such as the compound of Formula (I), and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to any composition or compound which inhibits any biological response associated with the binding of a GR to an agonist by preferentially binding to the GR rather than the mineralocorticoid receptor (MR). In a further related embodiment, the specific glucocorticoid receptor antagonist binds to the GR with an association constant ($K_d$) that is at least 10-fold less than the $K_d$ for the MR. In another embodiment, the specific glucocorticoid receptor antagonist binds to the GR with an association constant ($K_d$) that is at least 100-fold less than the $K_d$ for the MR. In another embodiment, the specific glucocorticoid receptor antagonist binds to the GR with an association constant ($K_d$) that is at least 1000-fold less than the $K_d$ for the MR.

IV. Pharmaceutical Compositions of Glucocorticoid Receptor Modulators

In another aspect, the present invention provides pharmaceutical compositions comprising a pharmaceutically acceptable excipient and a compound of the present invention, such as the compound of Formula (I) provided above.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The GR modulators of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions comprising a pharmaceutically acceptable carrier or excipient and either a compound of Formula (I), or a pharmaceutically acceptable salt of a compound of Formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a GR modulator in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.*

281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GR modulators of the invention can be delivered by transdermally, by a topical route, formulated as applicator sticks, solutions, suspensions, emulsions, gels, creams, ointments, pastes, jellies, paints, powders, and aerosols.

The GR modulators of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR modulator pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the GR modulator formulations of the invention are useful for parenteral administration, such as intravenous (IV) administration or administration into a body cavity or lumen of an organ. The formulations for administration will commonly comprise a solution of the GR modulator dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR modulator in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR modulator formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Treating Conditions Mediated by Glucocorticoid Receptors

In still another aspect, the present invention provides a method for the treatment of a disorder or condition through modulation of a glucocorticoid receptor. In this method, a subject in need of such treatment is administered an effective amount of a compound having one of the formulae provided above. The amount is effective in modulating the glucocorticoids receptor.

A variety of disease sates are capable of being treated with glucocorticoid receptor modulators. Exemplary disease states include major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain (e.g. pain associate with gastroesophageal reflux disease), postpartum psychosis, postpartum depression, neurological disorders in premature infants, migraine headaches, obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoperosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multidrug resistance, addiction, psychosis, anorexia, cahexia, post-traumatic stress syndrome post-surgical bone fracture, medical catabolism, and muscle frailty. The methods of treatment includes administering to a patient in need of such treatment, a therapeutically effective amount of a compound according to Formula (I), or a pharmaceutically acceptable salt thereof.

Thus, in an exemplary embodiment, the present invention provides a method of treating a disorder or condition through modulating a GR, the method comprising administering to a subject in need of such treatment, an effective amount of a compound of the present invention, such as a compound of Formula (I).

The amount of GR modulator adequate to treat a disease through modulating the GR is defined as a "therapeutically effective dose". The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Single or multiple administrations of GR modulator formulations can be administered depending on the dosage and frequency as required and tolerated by the patient. The formulations should provide a sufficient quantity of active agent to effectively treat the disease state. Thus, in one embodiment, the pharmaceutical formulations for oral administration of GR modulator is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR modulator formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

After a pharmaceutical comprising a GR modulator of the invention has been formulated in an acceptable carrier, it can be placed in an appropriate container and labeled for treatment of an indicated condition. For administration of GR modulators, such labeling would include, e.g., instructions concerning the amount, frequency and method of administration. In one embodiment, the invention provides for a kit for the treatment of delirium in a human which includes a GR modulator and instructional material teaching the indications, dosage and schedule of administration of the GR modulator.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states and/or the pharmaceutical compositions described herein. All publications, patents, and patent applications cited herein are hereby incorporated by reference in their entirety for all purposes.

EXAMPLES

Example 1

1,3-Dibenzyl-4-oxo-piperidine-3-carboxylic acid methyl ester (2: Y=H, Z=benzyl)

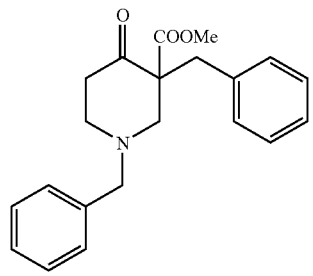

1-Benzyl-4-oxo-piperidine-3-carboxylic acid methyl ester hydrochloride salt (1, Z=benzyl) (15 g, 52.9 mmol) was suspended in DMF (150 mL) and cooled to 0° C. Sodium hydride (4.23 g, 105.8 mmol) was added portionwise over 1 h and the contents were allowed to warm to ambient temperature and stir for a further 1 h Benzyl bromide (6.3 mL, 53.0 mmol) was added over 15 min and the contents were stirred for a further 68 h at ambient temperature. 10 mL of water were added and the contents were diluted with 400 mL of ethyl acetate, washed with water (200 mL), saturated sodium bicarbonate (200 mL) and brine (200 mL). The organic layer was dried over magnesium sulfate, filtered and concentrated to give 20.5 g yellow oil that was purified by flash column chromatography (3:2 cyclohexane/$CH_2Cl_2$ to 100% $CH_2Cl_2$) to give 17.52 g (98%) of the title compound as a colorless oil. LC-MS: RT=2.80 min. $(M+H)^+$ 338, $(M-OMe)^+$ 306.

Example 2

1,3-Dibenzylpiperidin-4-one (3: Y=H, Z=benzyl)

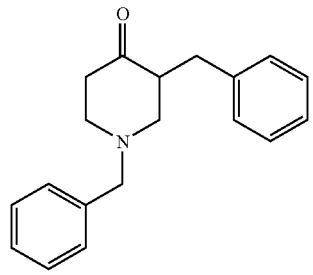

1,3-Dibenzyl-4-oxo-piperidine-3-carboxylic acid methyl ester, (2, Y=H, Z=benzyl) (17.52 g, 51.92 mmol) was suspended in 150 mL of 6N HCl:MeOH (5:1) and the mixture was heated to reflux temperature with stirring for 48 h. After cooling the mixture was basified to pH 10 with 6N NaOH and extracted with 3×200 mL dichloromethane. The combined organics were dried (MgSO$_4$) and concentrated to give 11.60 g of the title compound as a colorless oil, 80%. LC-MS: RT=0.38 min. (M+H)$^+$ 280.

Example 3

2,8a-Dibenzyl-1,3,4,7,8,8a-hexahydro-2H-isoquinolin-6-one (4: Y=H, Z=benzyl)

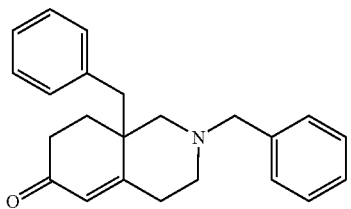

1,3-Dibenzylpiperidin-4-one (3, Y=H, Z=benzyl (3.98 g, 13.96 mmol) was added to a solution of sodium methoxide (0.83 g, 15.36 mmol) in 80 mL of methanol and stirred at ambient temperature for 45 min. The contents were cooled to 0° C. and methylvinyl ketone (1.74 mL, 20.94 mmol) was added over 30 min. The contents were allowed to warm to ambient temperature and stir for 18 h. Concentrated HCl (1.55 mL) was added, the contents were stirred for a further 5 min and the solvents were evaporated to give a brown oil which was triturated in diethyl ether to give the title compound, 1.90 g. LC-MS: RT=2.26 min. (M+H)$^+$ 332.

Example 4

8a-Benzyl-1,3,4,7,8,8a-hexahydro-2H-isoquinolin-6-one (5: Y=H)

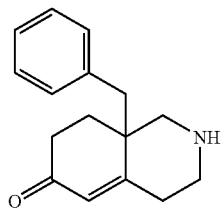

Compound 4 (Y=H, P=benzyl) (3.0 g (9.05 mmol) and α-chloroethyl chloroformate (1.22 mL, 11.3 mmol) in dichloroethane (50 mL) were heated to reflux under nitrogen for 18 h. After cooling, the mixture was concentrated in vacuo. Methanol (50 mL) was added and the contents heated to reflux for 6 h. The solvents were removed by evaporation and the residue was purified by flash column chromatography (100% CH$_2$Cl$_2$ to CH$_2$Cl$_2$/MeOH 9:1) to give the title compound as a pale brown solid, 1.51 g. LC-MS: RT=1.67 min. (M+H)$^+$ 242

The following compounds were prepared according to the procedures described in Examples 1 to 4:

8a-(3-Methoxybenzyl)-1,3,4,7,8,8a-hexahydro-2H-isoquinolin-6-one (5; Y=3-OMe)

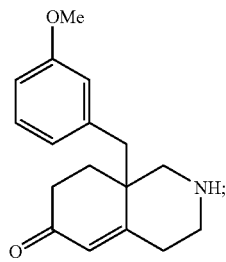

8a-(4-Methoxybenzyl)-1,3,4,7,8,8a-hexahydro-2H-isoquinolin-6-one (5; Y=4-OMe)

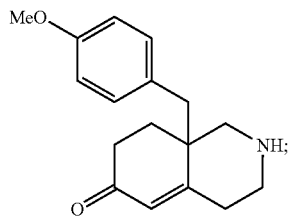

8a-(4-Bromobenzyl)-1,3,4,7,8,8a-hexahydro-2H-isoquinolin-6-one (5; Y=4-Br)

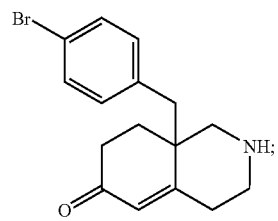

and 8a-(4-Nitrobenzyl)-1,3,4,7,8,8a-hexahydro-2H-isoquinolin-6-one (5; Y=4-NO$_2$)

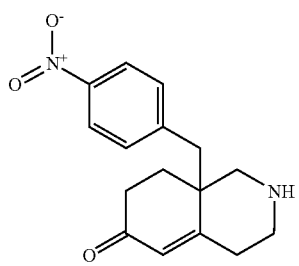

Example 5

8a-Benzyl-2-(4-methoxybenzyl)-1,3,4,7,8,8a-hexahydro-2H-isoquinolin-6-one (IA-1: Y=H, R$^4$=(4-OMe)Ph)

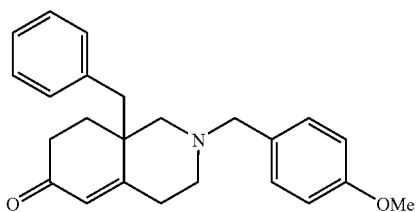

Compound 5 (Y=H) (100 mg, 0.41 mmol) was dissolved in 1 mL of THF. 60% Sodium hydride in mineral oil (16 mg, 0.41 mmol) was added and the mixture stirred for 10 min. 4-Methoxybenzyl bromide 0.41 mmol, 64 mg, was added and stirring was continued at ambient temperature for a further 18 h. Ethyl acetate (25 mL) was added and the mixture washed with water, brine and dried (MgSO$_4$). Concentration and purification by flash column chromatography (0 to 10% EtOAc in CH$_2$Cl$_2$) followed by trituration with diethyl ether afforded 58 mg of title compound as a white solid.

Also prepared by this method was 8a-Benzyl-2-(4-nitrobenzyl)-1,3,4,7,8,8a-hexahydro-2H-isoquinolin-6-one (IA-1: Y=H, R$^4$=(4-NO$_2$)Ph)

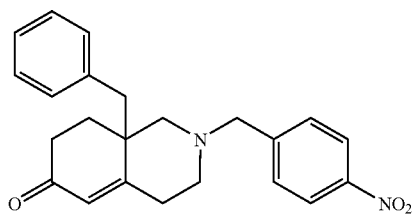

Example 6

8a-Benzyl-2-(furan-2-ylmethyl)-1,3,4,7,8,8a-hexahydro-2H-isoquinolin-6-one (IA-1: Y=H, R$^4$=2-furanyl)

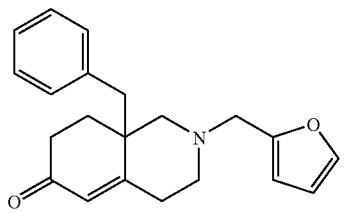

Compound 5 (Y=H) (87 mg, 0.36 mmol) and furan-2-carboxaldehyde (35 mg, 0.36 mmol) were stirred in dry CH$_2$Cl$_2$ for 10 min at ambient temperature. Sodium triacetoxyborohydride (106 mg, 0.50 mmol) was added and the resulting mixture was stirred for 90 min. Addition of saturated. NaHCO$_3$ followed by extraction with CH$_2$Cl$_2$, evaporation and purification by flash column chromatography gave 74 mg of the title compound. LC-MS: RT=2.15 min. (M+H)$^+$ 322.

Example 7

8a-Benzyl-2-(4-methoxyphenyl)-1,3,4,7,8,8a-hexahydro-2H-isoquinolin-6-one (IA-2: Y=H, R$^4$=(4-OMe)Ph)

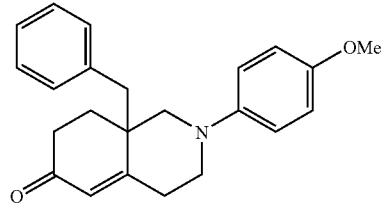

Compound 5 (Y=H) as the hydrochloride salt (100 mg, 0.36 mmol), 4-methoxyphenyl boronic acid (164 mg, 1.08 mmol) triethylamine (0.20 ml, 1.44 mmol) and copper (II) acetate (130 mg, 0.72 mmol) were stirred in dry CH$_2$Cl$_2$ for 24 h. The resulting crude product after evaporation of solvent was purified by flash column chromatography (0 to 5% EtOAc in CH$_2$Cl$_2$) to give 50 mg of the title compound. LC-MS: RT=4.06 min. (M+H)$^+$ 348.

Also prepared by this method were:

N-[3-(8a-Benzyl-6-oxo-3,4,7,8,8a-hexahydro-1H-isoquinolin-2-yl)phenyl]acetamide, (IA-2: Y=H, R4=(4-NHCOMe)Ph. LC-MS: RT=3.34 mins. (M+H)+ 375

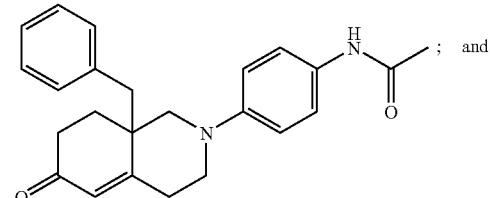

4-(8a-Benzyl-6-oxo-3,4,7,8,8a-hexahydro-1H-isoquinolin-2-yl)benzoic acid methyl ester, (IA-2: Y=H, R$^4$=(4-CO$_2$Me)Ph. LC-MS: RT=3.87 min. (M+H)$^+$ 376.

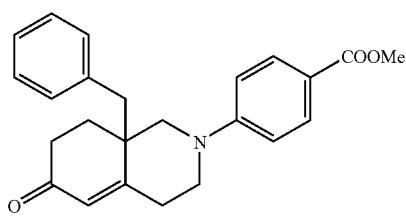

Example 8

-Benzoyl-8a-benzyl-1,3,4,7,8,8a-hexahydro-2H-isoquinolin-6-one (IA-3: Y=H, R$^{4M}$=Ph)

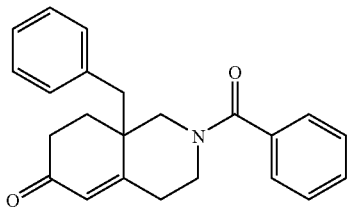

Compound 5 (Y=H) (81 mg, 0.34 mmol) was dissolved in CH$_2$Cl$_2$ (3 mL) and benzoyl chloride (43 µL, 0.37 mmol) was added followed by diisopropylethylamine (70 µL, 0.40 mmol). The contents were stirred at ambient temperature for 18 h, diluted with CH$_2$Cl$_2$, washed with water, brine, dried and concentrated to give a red oil that was purified by flash column chromatography (0 to 10% EtOAc in CH$_2$Cl$_2$) to give the title compound as a waxy pale yellow solid. LC-MS: RT=3.25 min. (M+H)+ 346.

Example 9

8a-Benzyl-6-oxo-3,4,6,7,8,8a-hexahydro-1H-isoquinoline-2-carboxylic acid phenylamide (IA-4: Y=H, R$^{4J}$=Ph, R$^{4K}$=H)

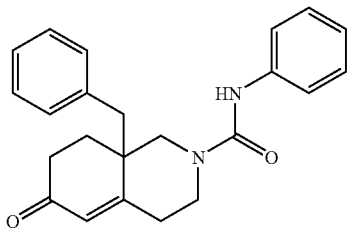

Compound 5 (Y=H) (96 mg, 0.398 mmol) was dissolved in CH$_2$Cl$_2$ under nitrogen and phenyl isocyanate (52 µL, 0.477 mmol) was added and the contents were stirred at ambient temperature for 18 h. The reaction mixture was diluted with CH$_2$Cl$_2$ and washed with water, dried, concentrated and purified by flash column chromatography (0 to 15% EtOAc in CH$_2$Cl$_2$) to give the title compound as a yellow glassy solid, 71 mg. LC-MS: RT=3.31 min. (M+H)+ 361.

Example 10

2-Benzenesulfonyl-8a-benzyl-1,3,4,7,8,8a-hexahydro-2H-isoquinolin-6-one (IA-5: Y=H, R$^{4A}$=Ph)

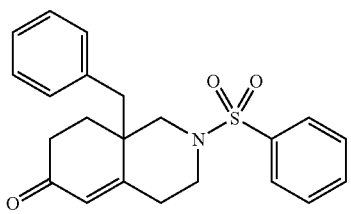

Benzenesulfonyl chloride (90.0 µmol) was added to a stirred solution of compound 5 (Y=H) (25.0 mg, 90.0 µmol), triethylamine (25.0 µL, 180 µmol) in 1,2-dichloroethane (3 mL). The resulting mixture was then stirred at room temperature for 18 h. PS-Trisamine resin (33.0 mg, loading=4.11 mmol/g) was added and the mixture was agitated at room temperature for a further 24 h. The mixture was filtered and the filtrate was purified by flash chromatography (CH$_2$Cl$_2$ 100% to 5% EtOAc in CH$_2$Cl$_2$) to afford the title compound 1 as a yellow oil, which solidified on standing. LC-MS: RT=3.68 min (M+H)+ 382.

The compounds of Table 1 were similarly prepared.

TABLE 1

| Number | Compound | Mass found (M + H)+ |
|---|---|---|
| 2 | | 460 |
| 3 | | 439 |
| 4 | | 475 |
| 5 | | 475 |

TABLE 1-continued
| Number | Compound | Mass found (M + H)+ |
|---|---|---|
| 6 | 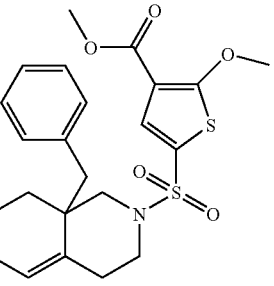 | 476 |
| 7 | 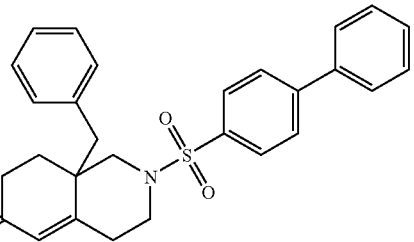 | 458 |
| 8 | 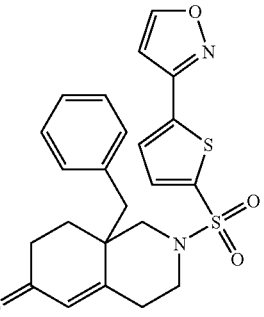 | 455 |
| 9 | 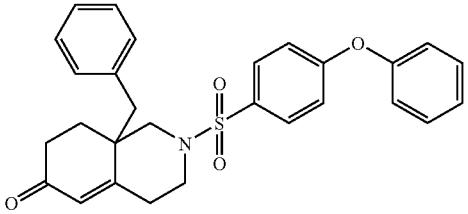 | 474 |
| 10 | 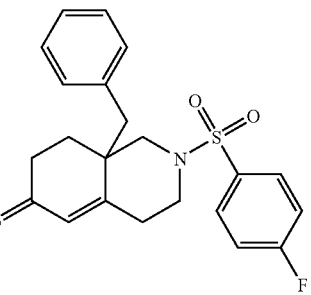 | 400 |
| 11 | 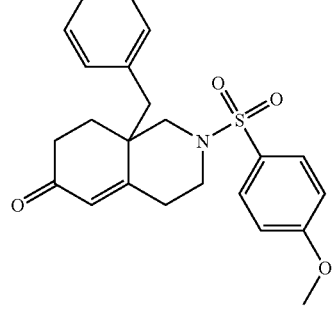 | 412 |
| 12 | 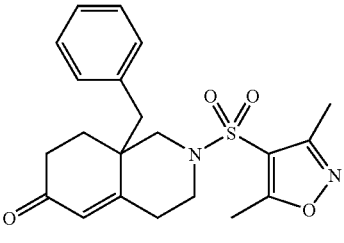 | 401 |
| 13 | 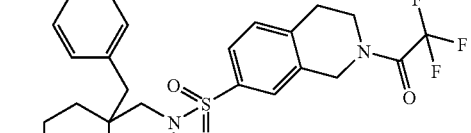 | 533 |
| 14 | 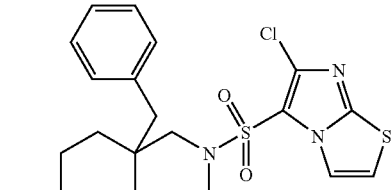 | 463 |
| 15 | 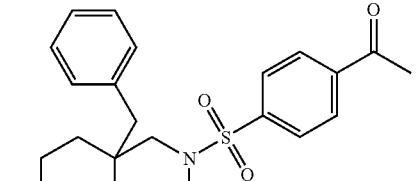 | 424 |
| 16 | 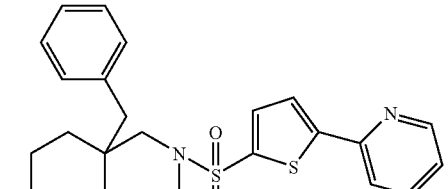 | 465 |

TABLE 1-continued

| Number | Compound | Mass found (M + H)⁺ |
|---|---|---|
| 17 | (benzyl-octahydroisoquinolinone-sulfonyl-quinoline) | 433 |
| 18 | (benzyl-octahydroisoquinolinone-sulfonyl-benzofurazan) | 424 |
| 19 | (benzyl-octahydroisoquinolinone-sulfonyl-2-naphthyl) | 432 |
| 20 | (benzyl-octahydroisoquinolinone-sulfonyl-4-chlorophenyl) | 416 |
| 21 | (benzyl-octahydroisoquinolinone-sulfonyl-styryl) | 408 |
| 22 | (benzyl-octahydroisoquinolinone-sulfonyl-benzyl) | 396 |
| 23 | (benzyl-octahydroisoquinolinone-sulfonyl-1-naphthyl) | 432 |
| 24 | (benzyl-octahydroisoquinolinone-sulfonyl-3-nitrophenyl) | 427 |
| 25 | (benzyl-octahydroisoquinolinone-sulfonyl-2-thienyl) | 388 |
| 26 | (benzyl-octahydroisoquinolinone-sulfonyl-4-tert-butylphenyl) | 438 |
| 27 | (benzyl-octahydroisoquinolinone-sulfonyl-4-nitrophenyl) | 427 |
| 28 | (benzyl-octahydroisoquinolinone-sulfonyl-2-nitro-4-trifluoromethylphenyl) | 495 |

TABLE 1-continued

| Number | Compound | Mass found (M + H)+ |
|---|---|---|
| 29 | | 442 |
| 30 | | 450 |
| 31 | | 446 |
| 32 | | 475 |
| 33 | | 423 |
| 34 | | 491 |
| 35 | | 417 |
| 36 | | 442 |
| 37 | | 407 |
| 38 | | 412 |
| 39 | | 460 |
| 40 | | 414 |

TABLE 1-continued
| Number | Compound | Mass found (M + H)+ |
|---|---|---|
| 41 | 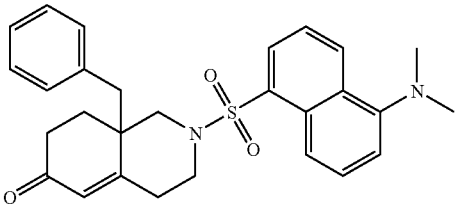 | 475 |
| 42 | 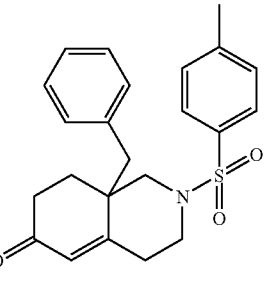 | 396 |
| 43 | 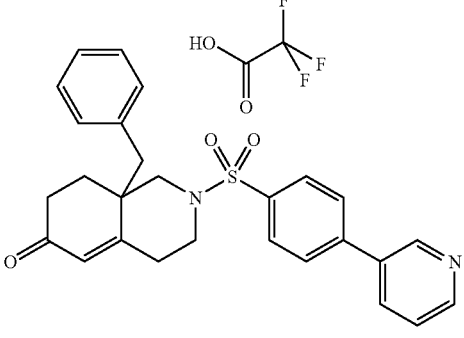 | 573 |
| 44 | 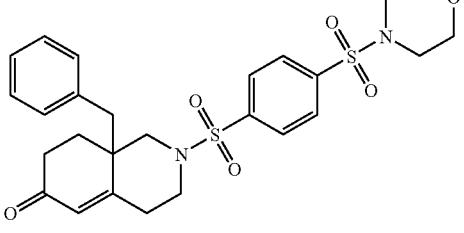 | 531 |
| 45 | 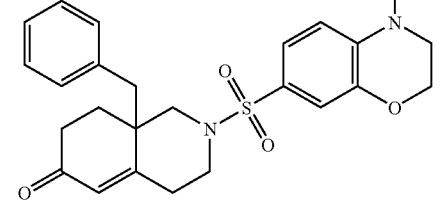 | 453 |
| 46 | 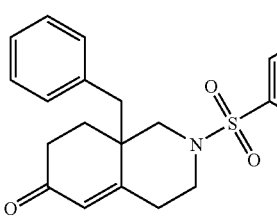 | 449 |
| 47 | 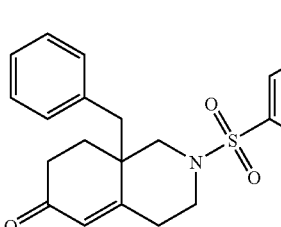 | 468 |
| 48 | 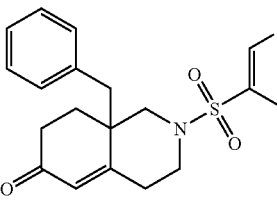 | 475 |
| 49 | 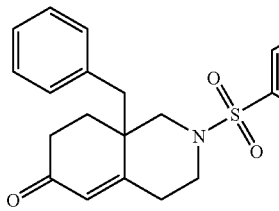 | 448 |
| 50 | 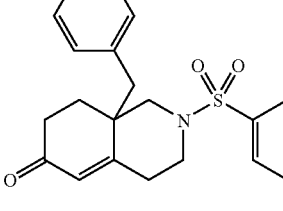 | 476 |

TABLE 1-continued

| Number | Compound | Mass found (M + H)+ |
|---|---|---|
| 51 | | 488 |
| 52 | | 615 |
| 53 | | 543 |
| 54 | | 468 |
| 55 | | 483 |
| 56 | | 426 |
| 57 | | 425 |
| 58 | | 467 |

TABLE 1-continued

| Number | Compound | Mass found (M + H)+ |
|---|---|---|
| 59 | 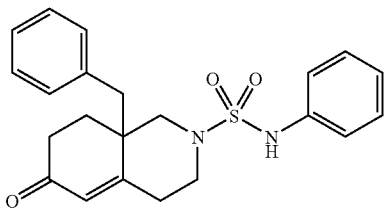 | 516 |
| 60 | | 468 |
| 61 | | 483 |

Example 11

8a-Benzyl-6-oxo-3,4,6,7,8,8a-hexahydro-1H-isoquinoline-2-sulfonic acid phenylamide (IA-6: Y=H, R^{4B}=Ph, R^{4C}=H)

Phenyl sulfamic acid sodium salt (1.0 g), prepared by the method of Audrieth L. F et al, *J. Org. Chem.* 1944, 9, 89-101, and PCl$_5$, 1.16 g were combined in the absence of solvent. After the exotherm subsided the contents were heated for a further 16 h at 70° C. Benzotrifluoride (5 mL) was added and the contents heated for a further 2 h, cooled, filtered and concentrated to give 182 mg of phenylsulfamoyl chloride. Compound 5 (Y=H) as its hydrochloride salt (20 mg, 0.085 mmol) was dissolved in 1 mL of dry CH$_2$Cl$_2$, and phenylsulfamoyl chloride (34 mg) in 0.5 mL of CH$_2$Cl$_2$ was added in portions followed by triethylamine (50 µL, 36 mg) in 0.5 mL of CH$_2$Cl$_2$. After stirring at ambient temperature for 16 h the reaction was quenched with saturated NaHCO$_3$, separated, washed with water and brine, dried and purified by flash column chromatography (2% EtOAc in CH$_2$Cl$_2$) to give 20 mg of the title compound. LC-MS RT=3.56 min. (M–H)$^-$ 395.

Example 12

2,8aβ-Dibenzyl-1,3,4,4aα,5,7,8,8aoctahydro-2H-isoquinolin-6-one (IB-1: Y=H, R$^4$=Ph)

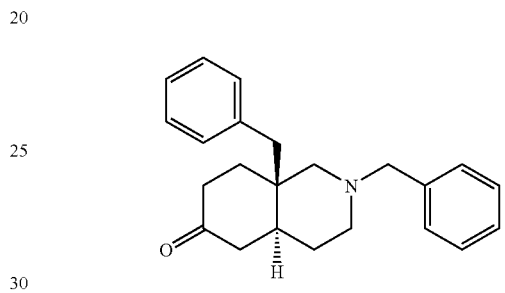

Lithium metal (150 mg) was added to a flask charged with 75 mL of liquid ammonia. 2,8a-Dibenzyl-1,3,4,7,8,8a-hexahydro-2H-isoquinolin-6-one (4, R=H) (2.0 g) was added and the contents were stirred at −78° C. for 20 min. A further 150 mg of lithium metal was added and stirring continued for a further 15 min. Solid ammonium chloride was added until the blue color was discharged. The contents were warmed to ambient temperature and extracted with dichloromethane. The organic phase was washed with saturated ammonium chloride, dried and concentrated to give a residue that was purified by flash column chromatography (10% EtOAc in CH$_2$Cl$_2$) to give 0.60 g of the title compound. LC-MS: RT=2.15 min. (M+H)$^+$ 334.

Example 13

8aβ-Benzyl-1,3,4,4aα,5,7,8,8a-octahydro-2H-isoquinolin-6-one (IB-1:Y=H, R$^4$=H)

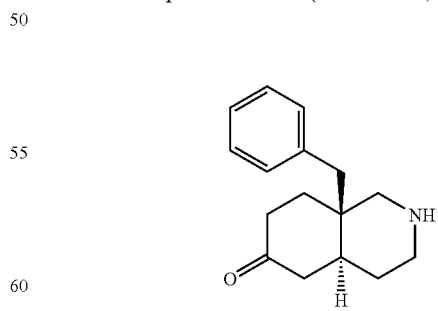

Compound IB-1 (Y=H, R$^4$=Ph) (1.14 g, 3.42 mmol) and palladium hydroxide (0.35 g, 0.342 mmol) were suspended in 40 mL of acetic acid and hydrogenated at atmospheric pressure for 21 h. The reaction mixture was filtered, concentrated and dissolved in CH$_2$Cl$_2$ and treated with 1M HCl in diethyl ether to give the title compound as its hydrochloride salt, a beige solid, 0.96 g. LC-MS RT=1.67 min. (M+H)⁺ 244.

Example 14

2-Benzenesulfonyl-8aβ-benzyl-1,3,4,4aα,5,7,8,8a-octahydro-2H-isoquinolin-6-one (IB-5: Y=H, R$^{4,4}$=Ph)

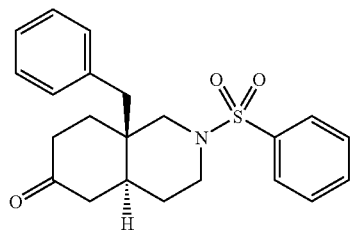

8aβ-Benzyl-1,3,4,4aα,5,7,8,8a-octahydroisoquinolin-6-one (IB-1: Y=H, R⁴=H) (84 mg, 0.348 mmol) and benzenesulfonyl chloride (49 μL, 0.383 mmol) were stirred in CH₂Cl₂ and diisopropylethylamine (73 μL) was added. The contents were stirred for 18 h, diluted with CH₂Cl₂, washed with water, brine, dried, concentrated and purified by flash column chromatography (10% EtOAc in CH₂Cl₂) to give the title compound, as a waxy pale yellow solid (83 mg). LC-MS: RT=3.24 min. (M+H)⁺ 384.

The compounds below were similarly prepared:

N-[4-(8aβ-Benzyl-6-oxo-3,4,4aα,5,6,7,8,8aα-octahydro-1H-isoquinoline-2-sulfonyl)phenyl]methanesulfonamide, compound (IB-5: Y=H, R$^{4,4}$=(4-NHSO₂Me)Ph)

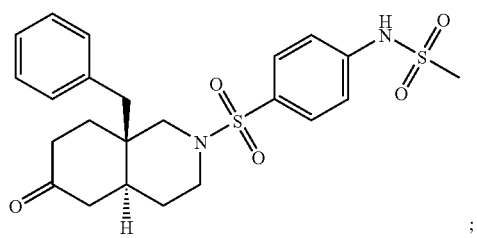

8aβ-Benzyl-2-(4-tert-butylbenzenesulfonyl)-1,3,4,4aα,5,7,8,8a-octahydro-2H-isoquinolin-6-one (IB-5: Y=H, R$^{4,4}$=(4-t-butyl)Ph)

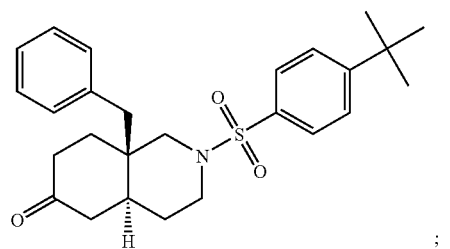

; and 2-(4-Acetylbenzenesulfonyl)-8aβ-benzyl-1,3,4,4aα,5,7,8,8a-octahydro-2H-isoquinolin-6-one (IB-5: Y=H, R$^{4,4}$=(4-COMe)Ph)

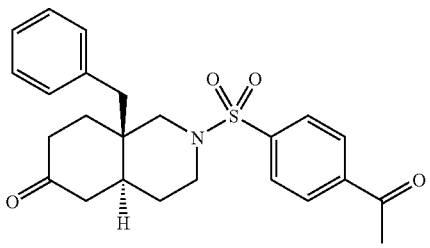

Example 15

8aβ-Benzyl-2-(4-tert-butylbenzenesulfonyl)-1,2,3,4,6,7,8,8a-octahydroiso quinolin-6β-ol (IA-7: Y=H, L⁴=SO₂, R⁴=(4-tert-butyl)Ph)

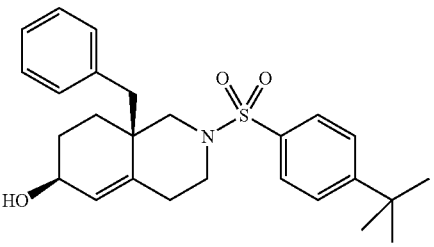

Compound IA-5 (Y=H, R⁴=(4-tert-butyl)Ph) (69 mg, 0.158 mmol) was dissolved in ethanol (4 mL) and sodium borohydride (24 mg, 0.632 mmol) was added in one portion. The contents were stirred at ambient temperature for 20 h, diluted with water, extracted with CH₂Cl₂, washed with water and brine, concentrated and purified by flash column chromatography (0 to 5% EtOAc in CH₂Cl₂) to give the title compound (18 mg). LC-MS: RT=4.21 min. (M+H)⁺ 440.

Example 16

8aβ-Benzyl-2-(4-tert-butylbenzenesulfonyl)-1,2,3,4,4aα,5,6,7,8,8a-decahydroisoquinolin-6β-ol (IB-7: Y=H, L⁴=SO₂, R⁴=(4-tert-butyl)Ph)

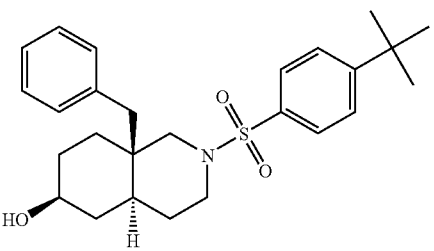

Compound IB-5 (Y=H, R⁴=(4-t-butyl)Ph)) (40 mg, 0.104 mmol) was dissolved in ethanol (2 mL). Sodium borohydride (16 mg, 0.417 mmol) was added and the contents were stirred at ambient temperature for 20 h. The contents were diluted with water and extracted with $CH_2Cl_2$. The organics were washed with water, brine, dried, concentrated and purified by flash column chromatography to give the title compound as a colourless oil (24 mg). LC-MS: RT=3.48 min. No (M+H) detected. NMR 400 MHz, $CDCl_3$ δ7.75, 7.60, 7.52, 7.45, 7.33, 7.22, 3.92, 3.70, 3.60, 3.10, 2.68, 2.16, 1-40-1.95, 1.50, 1.381.18, 0.68.

Prepared in a similar manner from compound IB-5 (Y=H, R⁴·⁴=Ph) was: 8aβ-Benzyl-2-(benzenesulfonyl)-1,2,3,4,4aα, 5,6,7,8,8a-decahydroisoquinolin-6β-ol (IB-7: Y=H, L⁴=SO₂, R⁴=Ph)

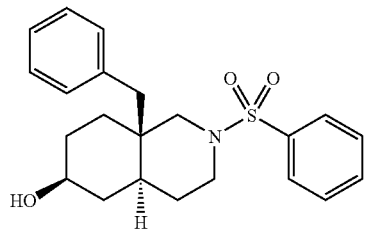

Example 17

8a-Benzyl-2-(4-tert-butylbenenesulfonyl)-6α-methyl-1,2,3,4,4aα,5,6,7,8,8a-decahydroisoquinolin-6β-ol (IB-9: Y=H, L⁴=SO₂, R²=Me, R⁴=(4-tert-butyl)Ph)

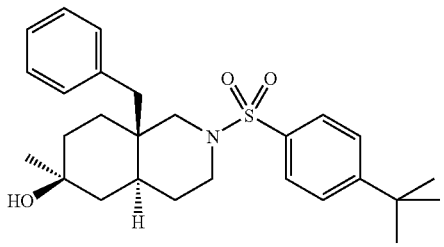

Compound IB-5 (Y=H, R⁴=(4-t-butyl)Ph)) (20 mg, 45.6 μmol) was dissolved in 1 mL of THF under nitrogen and cooled to 0° C. Methylmagnesium chloride (23 μL of a 3M THF solution, 68 μmol) was added dropwise and the contents were stirred at 0° C. for 1 h, then warmed to ambient temperature for a further 0.5 h. Saturated ammonium chloride solution was added and the contents were extracted with $CH_2Cl_2$, dried, concentrated and purified by flash column chromatography (5% EtOAc in $CH_2Cl_2$) to give the title compound as a white powder (12 mg). LC-MS: RT=4.28 min. (M+H)⁺ 456.

Example 18

8aβ-Benzyl-2-(4-tert-butylbenzenesulfonyl)-6β-methoxy-1,2,3,4,6,7,8,8a-octahydroiso quinoline (IA-11: Y=H, L⁴=SO₂, R¹·ᴊ=Me, R⁴=(4-t-butyl)Ph))

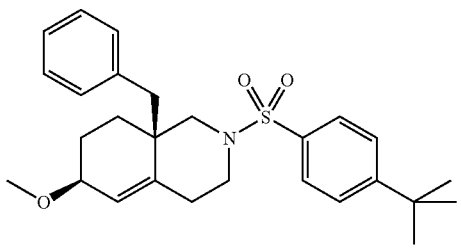

Compound IA-7 (Y=H, L⁴=SO₂, R⁴=(4-tert-butyl)Ph)) (14 mg, 0.032 mmol) was dissolved in 1 mL of THF under a nitrogen atmosphere and sodium hydride (60% dispersion in mineral oil, 7 mg, 0.175 mmol) was added, followed by methyl iodide (10 μL, 0.155 mmol). The suspension was heated to 75° C. for 20 h, then cooled and quenched with water and extracted with diethyl ether. The organic phase was washed with water, brine, dried ($MgSO_4$) and concentrated to give a yellow glass that was purified by silica chromatography (0 to 10% EtOAc in $CH_2Cl_2$) to give the title compound as a white powder. LC-MS: RT=4.82 mins. (M+H)⁺ 454.

Similarly prepared from IB-7 (Y=H, L⁴=SO₂, R⁴=(4-t-butyl)Ph)) was 8aβ-Benzyl-2-(4-tert-butylbenzenesulfonyl)-6β-methoxy-1,2,3,4,4aα,5,6,7,8,8a-decahydroisoquinoline (IB-11: Y=H, L⁴=SO₂, R⁴=(4-t-butyl)Ph), R¹·ᴊ=Me), LC-MS: RT=4.79 min. (M+H)⁺ 456.

Similarly prepared was 8aβ-Benzyl-2-(4-tert-butylbenzenesulfonyl)-6β-(2-methoxyethoxy)-1,2,3,4,4aα,5,6,7,8,8a-decahydroisoquinoline (IB-11: Y=H, L⁴=SO₂, R⁴=(4-t-butyl)Ph), R¹·ᴊ=(CH₂)₂OMe). LC-MS: RT=4.68 mins. (M+H)⁺ 500.

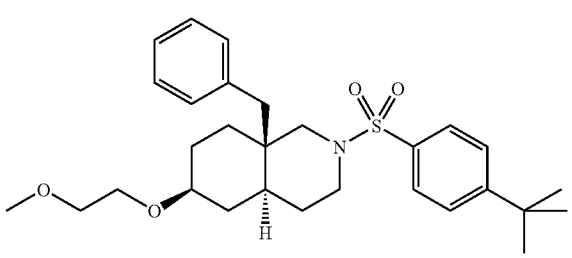

Example 19

8aβ-Benzyl-2-(4-tert-butylbenzenesulfonyl)-1,2,3,4,
4aα,5,6,7,8,8a-decahydroisoquinolin-6β-ylamine
(IB-13: Y=H, L$^4$=SO$_2$, R$^4$=(4-t-butyl)Ph), R$^{2E}$=H)
and 8aβ-Benzyl-2-(4-tert-butylbenzenesulfonyl)-1,2,
3,4,4aα,5,6,7,8,8a-decahydroisoquinolin-6α-ylamine
(IB-14: Y=H, L$^4$=SO$_2$, R$^4$=(4-t-butyl)Ph), R$^{2E}$=H)

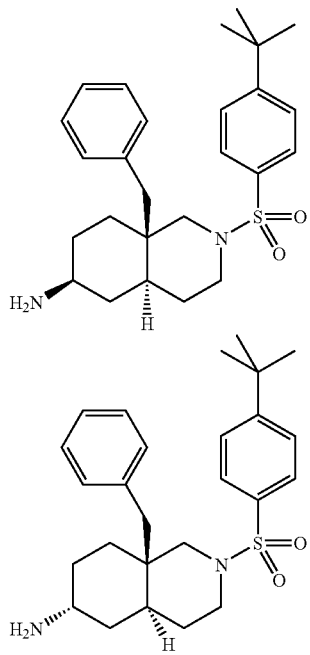

Compound IB-5 (Y=H, R$^4$=(4-t-butyl)Ph)) (40 mg, 0.091 mmol) was suspended in methanol 7 mL) with stirring. Ammonium acetate (84 mg, 1.09 mmol) was added followed by sodium cyanoborohydride (11.5 mg, 0.18 mmol) and the contents were stirred for 20 h. The solution was acidified to pH 2 with 1N HCl, then made basic with solid potassium carbonate, diluted with water and extracted with CHCl$_3$. The organic phase was washed with water, brine, dried (MgSO$_4$) and concentrated to give a colorless glass. Purification on silica (5-10% MeOH, CH$_2$Cl$_2$) gave amine IB-14 (6 mg) as a white solid. LC-MS: RT=2.80 min. (M+H)$^+$ 441, and amine IB-14 (16 mg) as a white solid. LC-MS: RT=2.81 min. (M+H)$^+$ 441.

Example 20

N-[8aβ-Benzyl-2-(4-tert-butylbenzenesulfonyl)-1,2,
3,4,4aα,5,6,7,8,8a-decahydroisoquinolin-6α-yl]-
acetamide (IB-14: Y=H, L$^4$=SO$_2$, R$^4$=(4-t-butyl)Ph), R$^{2E}$=acetyl)

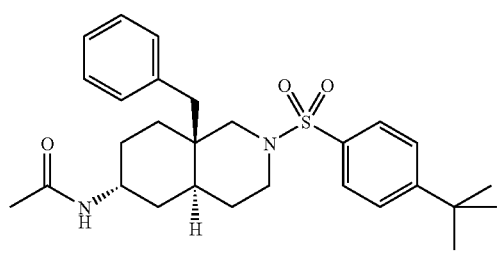

Compound IB-14 (Y=H, L$^4$=SO$_2$, R$^4$=(4-t-butyl)Ph), R$^{2E}$=H) (7 mg, 0.016 mmol) was dissolved in pyridine (1 mL). Acetic anhydride (15 μL, 0.154 mmol) was added and the solutions stirred at ambient temperature for 20 h. The residue was evaporated and purified by silica gel chromatography (0-20% EtOAc, CH$_2$Cl$_2$) to give the title compound (3.9 mg) as a white solid. LC-MS: RT=4.07 mins. (M+H)$^+$ 483.

Example 21

N-[8aβ-Benzyl-2-(4-tert-butylbenzenesulfonyl)-1,2,
3,4,4aα,5,6,7,8,8a-decahydroisoquinolin-6β-yl]-
acetamide (IB-13: Y=H, L$^4$=SO$_2$, R$^4$=(4-t-butyl)Ph), R$^{2E}$=acetyl)

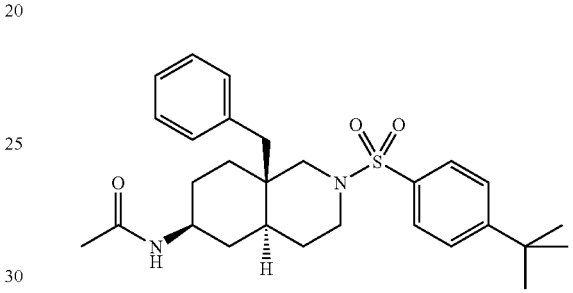

Similarly prepared from 8a Compound IB-13 (Y=H, L$^4$=SO$_2$, R$^4$=(4-t-butyl)Ph), R$^{2E}$=H). LC-MS: RT=4.05 min (M+H)$^+$ 483.

Example 22

2-Benzenesulfonyl-8a-benzyl-1,3,4,7,8,8a-hexahydro-2H-isoquinolin-6-one oxime (IA-17: Y=H, L$^4$=SO$_2$, R$^4$=Ph, R$^{2A}$=H)

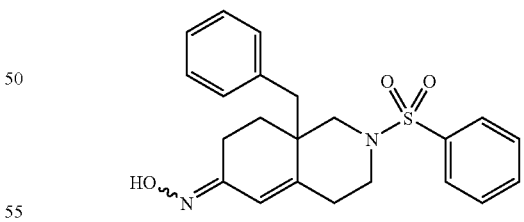

Compound IA-5 (Y=H, R$^4$=Ph) (35 mg, 0.09 mmol) was suspended in ethanol (1 ml). To it was added hydroxylamine sulfate (0.12 mmol in 250 μL of water) and the resulting mixture was stirred for 2 h at ambient temperature. The solvents were removed under vacuum and the residue was triturated with water. The precipitate was filtered and dried to give the title compound as a 3:1 mixture of oxime E/Z isomers. LC-MS: RT=3.58 & 3.62 min. (M+H)$^+$ 397; (M+CH$_3$CN+H)$^+$ 438.

The following compounds were similarly prepared:

2-Benzenesulfonyl-8a-benzyl-1,3,4,7,8,8a-hexahydro-2H-isoquinolin-6-one O-methyl oxime, compound IA-17 (Y=H, L$^4$=SO$_2$, R$^4$=Ph, R$^{2A}$=Me)

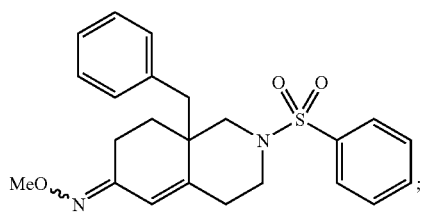

and

8a-Benzyl-2-(4-tert-butylbenzenesulfonyl)-1,3,4,7,8,8a-hexahydro-2H-isoquinoline-6-one O-methyl oxime, compound IA-17 (Y=H, L$^4$=SO$_2$, R$^4$=(4-t-butyl)Ph, R$^{2A}$=Me)

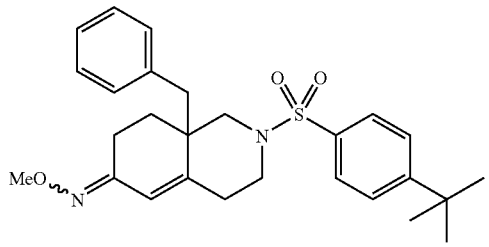

Example 23

8aβ-Benzyl-2-(4-tert-butylbenzenesulfonyl)-1,3,4,4aα,5,7,8,8a-octahydro-2H-isoquinolin-6-one oxime IB-17 (Y=H, L$^4$=SO$_2$, R$^4$=(4-t-butyl)Ph, R$^{2A}$=H)

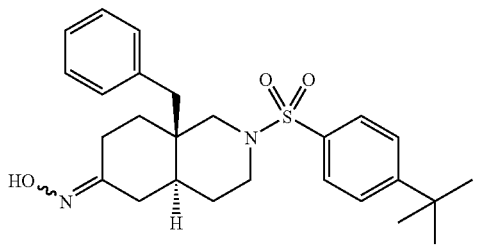

Compound IB (Y=H, L$^4$=SO$_2$, R$^4$=(4-t-butyl)Ph) (41.6 mg, 0.095 mmol suspended in 1 mL of ethanol. Hydroxylamine sulfate (17 mg, 0.104 mmol) and sodium acetate (8.5 mg, 0.104 mmol) in 250 μL water was added and the contents were stirred at ambient temperature for 18 h. The solvents were removed and the residue was partitioned between water and CH$_2$Cl$_2$ and stirred vigorously for 1 h. The organic layer was separated, dried and concentrated to give the title compound as a mixture of oxime E/Z isomers as a white solid (41 mg). LC-MS: RT=4.14 min. (M+H)$^+$ 455, (M+MeCN+H)$^+$ 496.

Example 24

8aβ-Benzyl-2-(4-tert-butylbenzenesulfonyl)-1,2,3,4,4aα,5,6,7,8,8a-decahydro-isoquinoline-6β-carboxylic acid methyl ester (8: Y=H, L$^4$=SO$_2$, R$^4$=(4-t-butyl)Ph)

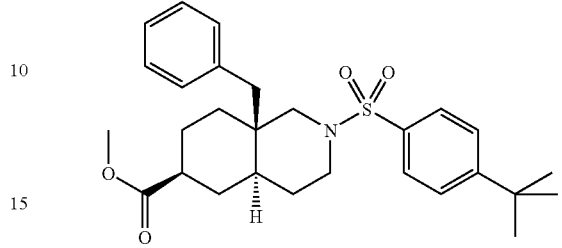

2-Trimethylsilyl-1,3-dithiane (92 μL, 0.483 mmol) was dissolved in THF (1 mL) and cooled to 0° C. under nitrogen. N-Butyllithium (0.19 mL of 2.5 M in hexanes, 0.48 mmol) was added and the solution was stirred at 0° C. for a further ten min. The solution was cooled to −78° C. and compound IB (Y=H, L$^4$=SO$_2$, R$^4$=(4-t-butyl)Ph) (100 mg, 0.23 mmol) in THF (1.5 mL) was added dropwise. The solution was stirred at −78° C. for a further 20 min. Brine (1 ml) was added and the contents were allowed to warm to ambient temperature and then diluted with water and extracted with CH$_2$Cl$_2$. The extract was dried and concentrated to give a crude product which was purified by silica gel chromatography to give 8aβ-benzyl-2-(4-tert-butylbenzenesulfonyl)-6-[1,3]dithian-2-ylidene-1,2,3,4,4aα,5,6,7,8,8a-decahydroisoquinoline (7: Y=H, X=SO$_2$, R$^4$=(4-t-butyl)Ph) as a white solid (115 mg). This intermediate was dissolved in methanol (8 ml) and perchloric acid (65 μl, 1.08 mmol), and mercury (II) chloride (229 mg, 0.85 mmol) were added. The mixture was heated to reflux for 2 h, then stirred at ambient temperature for 90 h. The contents were diluted with CH$_2$Cl$_2$ and filtered through HyFlo filter aid. The CH$_2$Cl$_2$ layer was washed with saturated Na$_2$SO$_3$ solution, dried and concentrated to give a residue that was purified by silica gel chromatography to give the title compound, as a colorless glass (79 mg). LC-MS: RT=4.78 min. (M+H)$^+$ 484.

Example 25

E & Z-[8aβ-Benzyl-2-(4-tert-butylbenzenesulfonyl)-1,3,4,4aα,5,7,8,8a-octahydro-2H octahydroisoquinolin-6-ylidene]-acetic acid ethyl ester (10: Y=H, L$^4$=SO$_2$, R$^4$=(4-t-butyl)Ph)

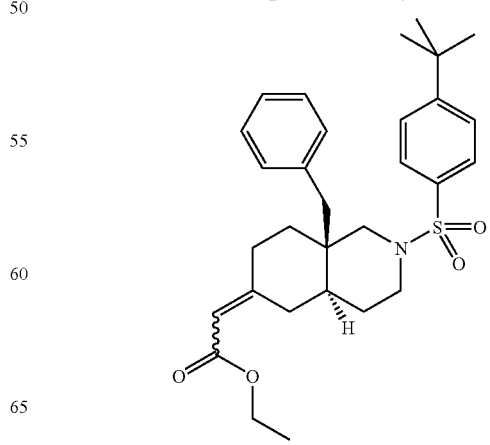

Sodium hydride (60% dispersion in mineral oil, 6.6 mg, 0.164 mmol) was suspended in dry THF (1 mL) under nitrogen and cooled to 0° C. Triethylphosphonoacetate (27 μL, 0.137 mmol) was added dropwise and the mixture was stirred at 0° C. for 15 min. Compound IB (Y=H, L⁴=SO₂, R⁴=(4-t-butyl)Ph) (50 mg, 0.114 mmol) in THF (0.7 mL) was added and the reaction mixture was stirred at ambient temperature for 20 h. The reaction contents were partitioned between brine and diethyl ether, and the organic layer was separated, dried (MgSO₄) and evaporated to give a mixture of E and Z geometric isomers as a white solid (60 mg). These were purified by flash column chromatography (CH₂Cl₂): LC-MS: RT=5.04 min. (M+H)⁺ 510 (Z-isomer); RT=5.00 min. (M+H)⁺ 510 (E-isomer).

Example 26

[8aβ-Benzyl-2-(4-tert-butylbenzenesulfonyl)-1,2,3,4,4aα,5,6,7,8,8a-decahydro-isoquinolin-6-yl]acetic acid ethyl ester (11: Y=H, L⁴=SO₂, R⁴=(4-t-butyl)Ph)

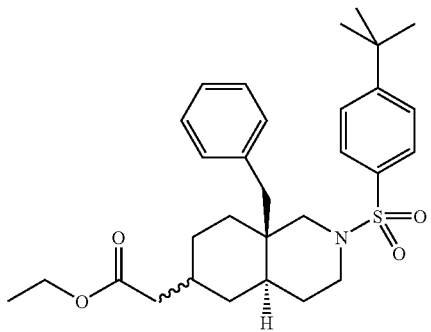

Compound 10 (Y=H, L⁴=SO₂, R⁴=(4-t-butyl)Ph) (34 mg, 0.067 mmol) was dissolved in ethyl acetate (1.5 mL) and platinum (IV) oxide (4.5 mg) was added. The mixture was stirred under a hydrogen atmosphere (1 atmosphere pressure) for 22 h and then filtered through a pad of HyFlo filter aid and concentrated to give a residue that was purified by flash chromatography (cyclohexane/diethyl ether 3:1) to give the title compound as a mixture of epimers (6 mg of a white solid). LC-MS: RT=4.99 min. (M+H)⁺ 512.

Example 27

[8aβ-Benzyl-2-(4-tert-butyl-benzenesulfonyl)-1,2,3,4,4aα,5,6,7,8,8a-decahydroisoquinolin-6-yl]methanol (IB-19a: Y=H, L⁴=SO₂, R⁴=(4-t-butyl)Ph)

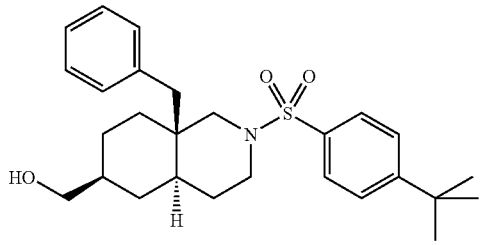

8aβ-Benzyl-2-(4-tert-butylbenzenesulfonyl)-1,2,3,4,4aα,5,6,7,8,8a-decahydro-isoquinoline-6β-carboxylic acid methyl ester (8) (14 mg, 0.029 mmol) was dissolved in THF (0.5 mL) under nitrogen. LiAlH₄ (11 mg, 0.29 mmol) was added and the contents were stirred at ambient temperature for 45 min. 2 drops of water and 2 drops of 1N NaOH were added and the mixture was stirred for 10 min. MgSO₄ was added and the contents were filtered and the filtrate was concentrated to give a colorless glass. Purification by flash column chromatography gave the title compound as a white powder (12 mg). LC-MS: RT=4.36 min. (M+H)⁺ 456.

Similarly prepared from [8aβ-Benzyl-2-(4-tert-butylbenzenesulfonyl)-1,2,3,4,4aα,5,6,7,8,8a-decahydro-isoquinolin-6-yl]acetic acid ethyl ester (11) were 2-[8aβ-Benzyl-2-(4-tert-butylbenzenesulfonyl)-1,2,3,4,4aα,5,6,7,8,8a-decahydro-isoquinolin-6α-yl]-ethanol (IB-22, Y=H, L⁴=SO₂, R⁴=(4-t-butyl)Ph, R²ᴰ³=H) and 2-[8aβ-Benzyl-2-(4-tert-butylbenzenesulfonyl)-1,2,3,4,4aα,5,6,7,8,8a-decahydro-isoquinolin-6β-yl]-ethanol (IB-22, Y=H, X=SO₂, R⁴=(4-t-butyl)Ph, R²ᴰ³=H).

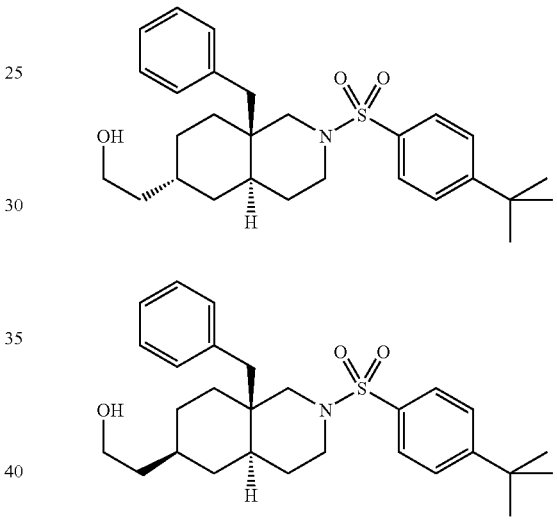

Example 28

2-(4-tert-Butylbenzenesulfonyl)-8a-[4-(4,4,5,5-tetramethyl-[1,3,2]dioxaborolan-2-yl)benzyl]-1,3,4,7,8,8a-hexahydro-2H-isoquinolin-6-one (IA-5: Y=4-(B(OC(CH₃)₂C(CH₃)₂O), R⁴=(4-t-butyl)Ph)

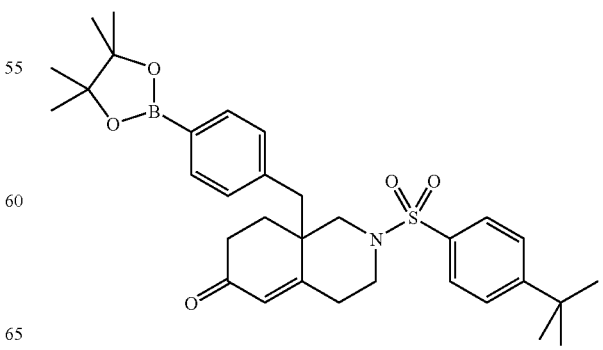

8a-(4-Bromobenzyl)-2-(4-t-butylbenzenesulfonyl)-1,3,4,7,8,8a-hexahydro-2H-isoquinolin-6-one (IA-5: Y=4-Br, R⁴=4-(tert-butyl)Ph) (0.50 g, 0.97 mmol), (bispinacolato)diboron (0.27 g, 1.07 mmol), PdCl$_2$(dppf) (35.4 mg, 5 mol %), NaOAc (0.238 g, 2.90 mmol) and DMF (2 mL) were heated in a microwave reactor at 140° C. for 10 min. The DMF was removed under vacuum and ethyl acetate (50 mL) was added to the residue which was washed with water, brine and dried (MgSO$_4$) and concentrated under vacuum. Purification by flash chromatography (0-20% EtOAc in CH$_2$Cl$_2$) gave the title compound as a colorless oil LC-MS: RT=4.77 min. (M+H)⁺ 564

Example 29

2-(4-tert-Butylbenzenesulfonyl)-8a-(4-piperidin-1-ylbenzyl)-1,3,4,7,8,8a-hexahydro-2H-isoquinolin-6-one (IA-5: Y=4-piperidin-1-yl, R⁴=4-(t-butyl)Ph)

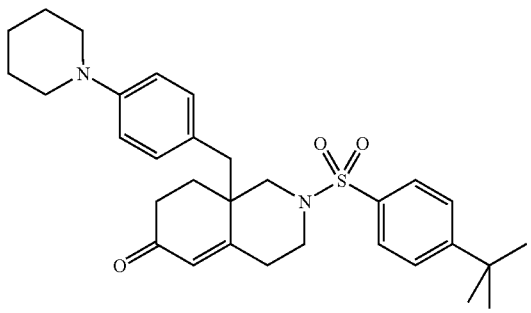

2-(4-t-Butylbenzenesulfonyl)-8a-[4-(4,4,5,5-tetramethyl-[1,3,2]dioxaborolan-2-yl)benzyl]-1,3,4,7,8,8a-hexahydro-2H-isoquinolin-6-one (IA-5: Y=4-(B(OC(CH$_3$)$_2$C(CH$_3$)$_2$O)) (50 mg, 0.089 mmol), piperidine (11 mg, 13.2 µL, 0.14 mmol), Cu(OAc)$_2$ (8 mg, 0.044 mmol), pyridine (7.2 µL, 0.089 mmol) and CH$_2$Cl$_2$ (1 mL) were stirred at ambient temperature for 48 h. The reaction contents were loaded directly onto a small silica cartridge and eluted with 10% EtOAc in CH$_2$Cl$_2$ to give a colorless oil (14 mg) that was further purified by reverse-phase preparative HPLC to give the title compound as a colorless glass (4 mg) LC-MS: RT=3.14 min. (M+H)⁺ 521.

The following compounds were similarly prepared from 2-(4-t-Butylbenzenesulfonyl)-8a-[4-(4,4,5,5-tetramethyl-[1,3,2]dioxaborolan-2-yl)benzyl]-1,3,4,7,8,8a-hexahydro-2H-isoquinolin-6-one (IA-5: Y=4-(B(OC(CH$_3$)$_2$C(CH$_3$)$_2$O)):

2-(4-t-Butylbenzenesulfonyl)-8a-(4-morpholin-4-ylbenzyl)-1,3,4,7,8,8a-hexahydro-2H-isoquinolin-6-one (IA-5: Y=4-morpholin-4-yl, R⁴=4-(t-butyl)Ph)

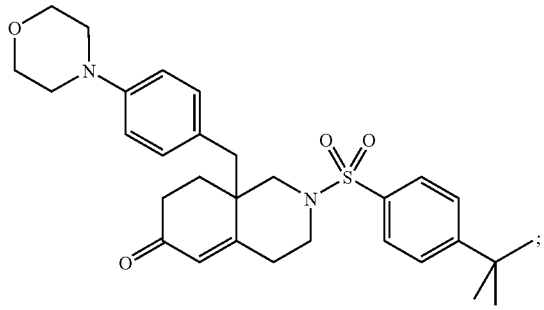

2-(4-t-Butylbenzenesulfonyl)-8a-[4-(4-methylpiperazin-1-yl)benzyl]-1,3,4,7,8,8a-hexahydro-2H-isoquinolin-6-one (IA-5: Y=4-(4-methylpiperazin-1-yl), R⁴=4-(t-butyl)Ph)

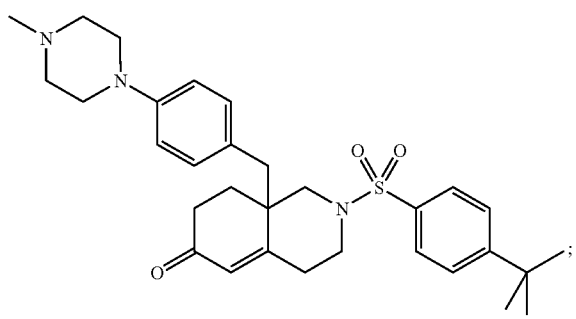

and 2-(4-t-Butylbenzenesulfonyl)-8a-[4-(4-hydroxypiperidin-1-yl)benzyl]-1,3,4,7,8,8a-hexahydro-2H-isoquinolin-6-one (IA-5: Y=4-(4-hydroxypiperidin-1-yl, R⁴=4-(t-butyl)Ph)

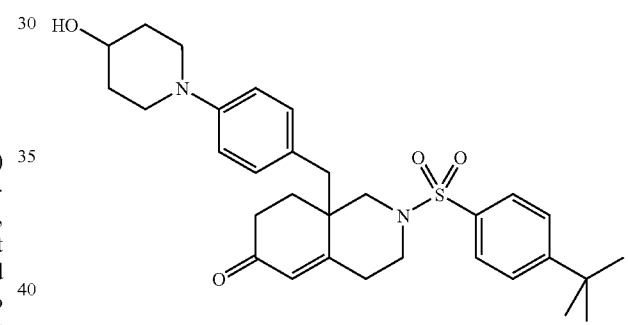

Example 30

2-(4-t-Butylbenzenesulfonyl)-8a-(4-pyridin-4-ylbenzyl)-1,3,4,7,8,8a-hexahydro-2H-isoquinolin-6-one (IA-5: Y=4-(4-pyridin-4-yl, R⁴=4-(t-butyl)Ph)

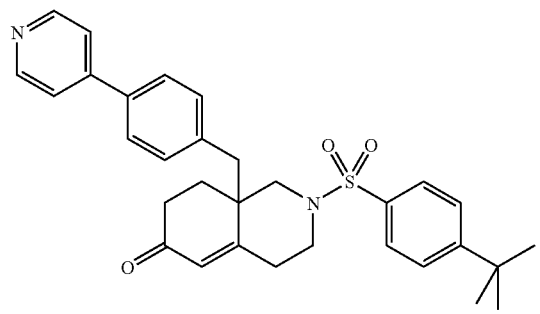

8a-(4-Bromobenzyl)-2-(4-tert-butylbenzenesulfonyl)-1,3,4,7,8,8a-hexahydro-2H-isoquinolin-6-one (IA-5: Y=4-Br, R⁴=4-(t-butyl)Ph) (50 mg, 0.097 mmol), pyridine-4-boronic acid (17.8 mg, 0.145 mmol), $Cs_2CO_3$ (0.2 mL of a 2M aq. solution), $PdCl_2$(dppf) (7.3 mg, 10 mol %) and DMF (0.5 mL) were combined and heated to 140° C. in a microwave reactor for 10 min. After cooling, $CH_2Cl_2$ (25 mL) was added and the organics were washed with 1M NaOH, water and brine, dried ($MgSO_4$) and concentrated. The resulting residue was purified by flash chromatography (0-50% EtOAc in $CH_2Cl_2$) to give the title compound as an orange oil (26 mg). LC-MS: RT=3.03 min. $(M+H)^+$ 515.

The following compounds were similarly prepared:

2-(4-tert-Butylbenzenesulfonyl)-8a-(4-pyrimidin-5-ylbenzyl)-1,3,4,7,8,8a-hexahydro-2H-isoquinolin-6-one (IA-5: Y=4-pyrimidin-5-yl, $R^4$=4-(tert-butyl)Ph)

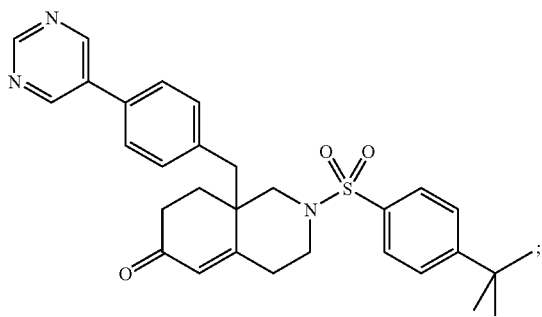

and 2-(4-tert-Butylbenzenesulfonyl)-8a-[4-(1H-pyrazol-4-yl)benzyl]-1,3,4,7,8,8a-hexahydro-2H-isoquinolin-6-one (IA-5: Y=4-(1H-pyrazol-4-yl), $R^4$=4-(tert-butyl)Ph)

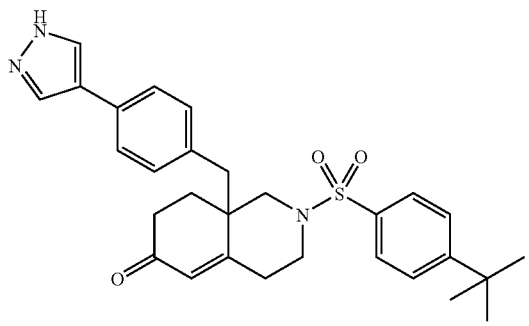

Example 31

6-Oxo-4,6,7,8-tetrahydro-3H-isoquinoline-2,8a-dicarboxylic acid 2-tertbutyl ester 8a-methyl ester (13: $L^3$=CO, $R^3$=$OCH_3$, Z=Boc)

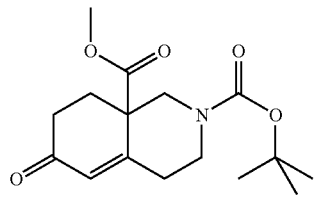

4-Oxo-piperidine-1,3-dicarboxylic acid 1-tert-butyl ester 3-methyl ester 12 ($L^3$=CO, $R^3$=$OCH_3$, Z=Boc) (8.9 g, 34.6 mmol) was dissolved in dichloromethane (25 mL) and iron$^{III}$ chloride (0.28 g, 1.73 mmol) and methylvinyl ketone (5.76 mL, 69.2 mmol) were added and stirred at ambient temperature for 18 hours. The volatile materials were removed in vacuo. The residue was redissolved in dichloromethane (60 mL) and pyrrolidine (2.13 mL, 25.6 mmol) and acetic acid (1.46 mL, 25.6 mmol) were added and stirred at ambient temperature for 19 hours. The solvents were removed in vacuo and the residue purified by flash chromatography ($CH_2Cl_2$ 100% to 10% EtOAc in $CH_2Cl_2$) to afford 6.72 g of the title compound 13 ($L^3$=CO, $R^3$=$OCH_3$, Z=Boc) as a yellow oil. LC-MS: RT=3.04 min $(M+H)^+$ 310.

Example 32

6-Oxo-2,3,4,6,7,8-hexahydro-1H-isoquinoline-8a-carboxylic acid methyl ester (14: $L^3$=CO, $R^3$=$OCH_3$)

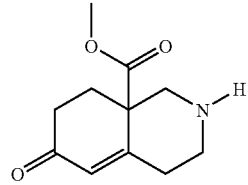

Trifluoroacetic acid (5.22 mL, 45.8 mmol) in dichloromethane (20 mL) was added to 13 ($L^3$=CO, $R^3$=$OCH_3$, Z=Boc) (7.10 g, 22.9 mmol) and stirred at ambient temperature for 2 h. The solvents were evaporated to give 4.8 g of 14 ($L^3$=CO, $R^3$=$OCH_3$) as a yellow oil. Due to poor stability, this compound was used immediately in subsequent reactions without purification.

Example 33

2-(4-tert-Butylbenzenesulfonyl)-6-oxo-2,3,4,6,7,8-hexahydro-1H-isoquinoline-8a-carboxylic acid methyl ester (IA-27: $L^3$=CO, $R^3$=$OCH_3$, $R^{4,4}$=4-(t-butyl)Ph)

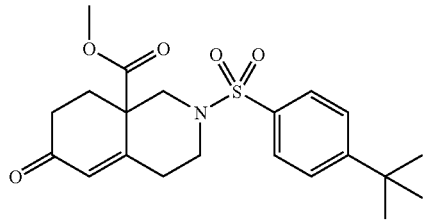

4-tert-Butylbenzenesulfonyl chloride (4.27 g, 18.4 mmol) was added to a stirred solution of compound 14 ($L^3$=CO, $R^3$=OMe) (12.1 g, 16.7 mmol), triethylamine (14.5 mL, 83.5 mmol) in 1,2-dichloromethane (150 mL). The resulting mixture was then stirred at room temperature for 21 h. The reaction mixture was washed with water, dried ($MgSO_4$), concentrated and purified by flash chromatography ($CH_2Cl_2$ 100% to 10% EtOAc in $CH_2Cl_2$) to afford 6.7 g the title compound IA-27 ($L^3$=CO, $R^3$=$OCH_3$, $R^{4,4}$=4-(t-butyl)phenyl) as a yellow oil, which solidified on standing. LC-MS: RT=3.84 min $(M+H)^+$ 406.

Example 34

2-(4-tert-Butylbenzenesulfonyl)-6,6-ethylenedioxy-2,3,5,6,7,8-hexahydro-1H-isoquinoline-8a-carboxylic acid methyl ester (15: $L^3$=CO, $R^3$=OCH$_3$, $R^{4.4}$=4-(t-butyl)Ph)

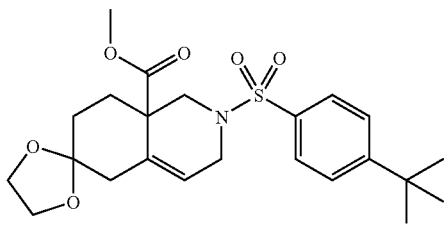

2-(4-tert-Butyl-benzenesulfonyl)-6-oxo-2,3,4,6,7,8-hexahydro-1H-isoquinoline-8a-carboxylic acid methyl ester (IA-27: $L^3$=CO, $R^3$=OMe, $R^{4.4}$=4-(t-butyl)phenyl) (4.6 g, 11.36 mmol) was dissolved in dimethoxyethanol (40 mL) and ethylene glycol (40 mL) and chlorotrimethylsilane (10.1 mL, 79.52 mmol) were added and the mixture was stirred at ambient temperature for 17 h. The reaction was cooled to 0° C. and quenched with saturated sodium bicarbonate solution then the organics extracted with 3×100 mL dichloromethane. The solvents were removed in vacuo to afford 4.70 g of the title compound 15 ($L^3$=CO, $R^3$=OMe, $R^{4.4}$=4-(t-butyl)Ph) as a white solid. LC-MS: RT=4.01 min (M+H)$^+$ 450.

Example 35

[2-(4-tert-Butyl-benzenesulfonyl)-6,6-ethylenedioxy-2,3,5,6,7,8-hexahydro-1H-isoquinolin-8a-yl]-methanol (16: $R^{4.4}$=4-(t-butyl)Ph)

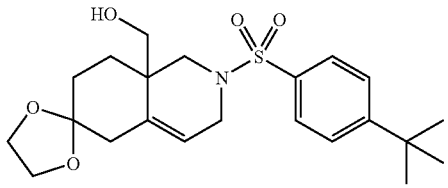

Compound 15 ($L^3$=CO, $R^3$=OMe, $R^{4.4}$=4-(t-butyl)Ph (4.70 g, 10.47 mmol) was dissolved in dichloromethane (100 mL) under nitrogen and the temperature was reduced to −78° C. DIBAL-H (1M solution, 41.9 mL, 41.9 mmol) was added slowly and the reaction mixture was stirred for 2 h. Methanol (10 mL) was added and the solution was allowed to warm to room temperature. Water was added and the organic layer was collected, dried (MgSO$_4$) and concentrated in vacuo. The residue was purified by flash chromatography to afford 0.16 g of 16 (CH$_2$Cl$_2$ 100% to 10% EtOAc in CH$_2$Cl$_2$). LC-MS: RT=3.65 min. (M+H)$^+$ 422.

Example 36

2-(4-tert-Butyl-benzenesulfonyl)-8a-ethoxymethyl-6,6-ethylenedioxy-1,2,3,5,6,7,8,8a-octahydro-isoquinoline (17: $R^{3.4}$=CH$_2$CH$_3$, $R^{4.4}$=4-(t-butyl)Ph, R=Et)

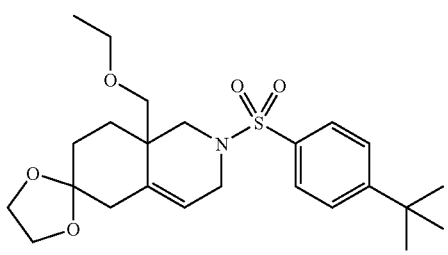

Compound 16 ($R^{4.4}$=4-(t-butyl)Ph) (102 mg, 0.24 mmol) was dissolved in tetrahydrofuran (10 mL) under nitrogen and then sodium hydride (29 mg, 0.73 mmol) was added. After 10 min, ethyl bromide (53 μL, 0.73 mmol) was added and heated at 75° C. for 18 h. After cooling, water was added and the organics extracted with dichloromethane and concentrated in vacuo. The residue was purified by flash chromatography to afford 103 mg of the title compound (CH$_2$Cl$_2$ 100% to 10% EtOAc in CH$_2$Cl$_2$). LC-MS: RT=4.41 min. (M+H)$^+$ 472.

The following compounds were similarly prepared from [2-(4-tert-Butyl-benzenesulfonyl)-6,6-ethylenedioxy-2,3,5,6,7,8-hexahydro-1H-isoquinolin-8a-yl]-methanol (16):

2-(4-tert-Butyl-benzenesulfonyl)-6,6-ethylenedioxy-8a-(2-methoxy-ethoxymethyl)-1,2,3,5,6,7,8,8a-octahydro-isoquinoline (17: $R^{3.4}$=CH$_2$CH$_2$OCH$_3$, $R^{4.4}$=4-(t-butyl)Ph)

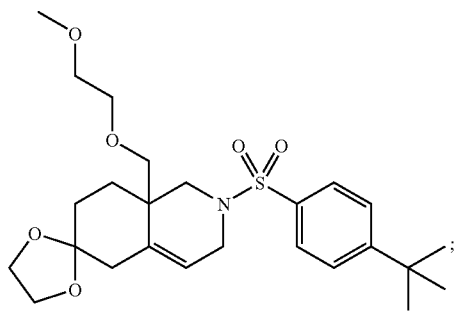

and 2-(4-tert-Butyl-benzenesulfonyl)-6,6-ethylenedioxy-8a-(pyridin-2-yloxymethyl)-1,2,3,5,6,7,8,8a-octahydro-isoquinoline (17: $R^{3.4}$=(2-pyridyl), $R^{4.4}$=4-(t-butyl)Ph)

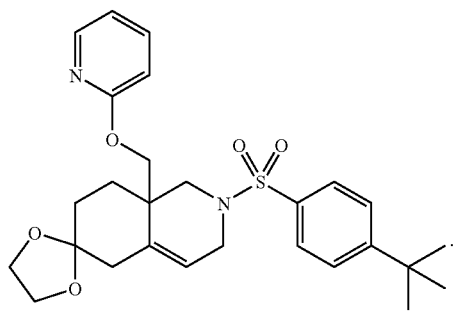

Example 37

2-(4-tert-Butyl-benzenesulfonyl)-8a-ethoxymethyl-1,3,4,7,8,8a-hexahydro-2H-isoquinolin-6-one (IA-29: $R^{3A}$=CH$_2$CH$_3$, $R^{4A}$=4-(t-butyl)Ph)

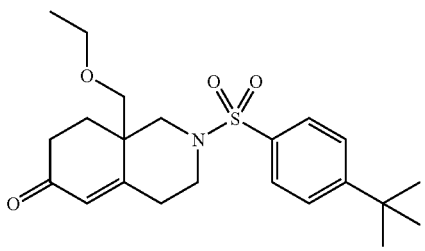

Compound 17 ($R^{3A}$=CH$_2$CH$_3$, $R^{4A}$=4-(t-butyl)Ph) (103 mg, 0.23 mmol dissolved in dichloromethane (4 mL) and cooled to 0° C. where perchloric acid (68 μL, 1.15 mmol) was added. After 40 min at this temperature, the reaction was warmed to ambient temperature and stirring continued for an additional 90 min. Saturated sodium bicarbonate solution (10 mL) was added and the mixture was extracted with 3× CH$_2$Cl$_2$ (10 mL), and concentrated in vacuo. The residue was purified by flash chromatography to afford 97 mg of the title compound (CH$_2$Cl$_2$ 100% to 10% EtOAc in CH$_2$Cl$_2$). LC-MS: RT=4.05 min. (M+H)$^+$ 406.

The following compounds were similarly prepared:

2-(4-tert-Butylbenzenesulfonyl)-8a-(2-methoxyethoxymethyl)-1,3,4,7,8,8a-hexahydro-2H-isoquinolin-6-one (IA-29: $R^{3A}$=OCH$_2$CH$_2$OCH$_3$, $R^{4A}$=4-(t-butyl)Ph)

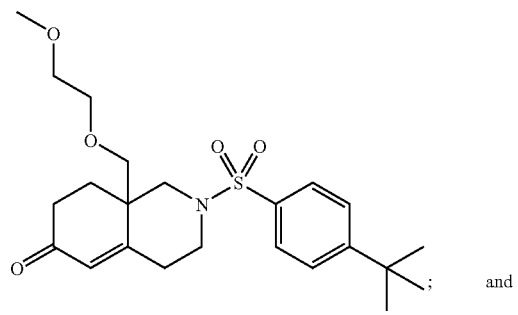

and 2-(4-tert-Butyl-benzenesulfonyl)-8a-(pyridin-2-yloxymethyl)-1,3,4,7,8,8a-hexahydro-2H-isoquinolin-6-one (IA-29: $R^{3A}$=(2-pyridyl), $R^{4A}$=4-(t-butyl)Ph)

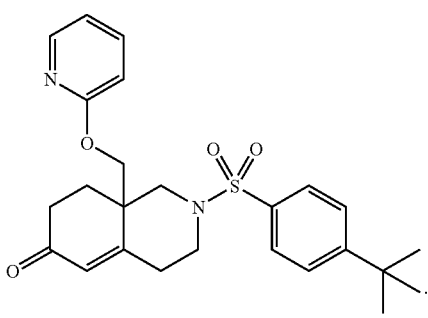

Example 38

2-(4-tert-Butyl-benzenesulfonyl)-6,6-ethylenedioxy-2,3,5,6,7,8 hexahydro-1H-isoquinoline-8a-carbaldehyde (18: $R^{4A}$=4-(t-butyl)Ph)

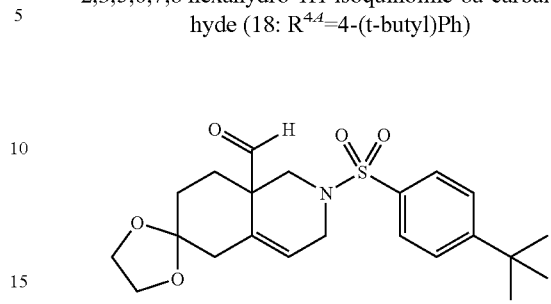

Oxalyl chloride (30 μL, 0.34 mmol) was added to a solution of DMSO (54 μL, 0.77 mmol) in dichloromethane (5 mL) at −78° C. Compound 16 (66 mg, 0.16 mmol) was dissolved in dichloromethane (2 mL) and added slowly to the reaction mixture. After 45 min, triethylamine (77 μL, 0.77 mmol) was added and the reaction mixture was warmed to ambient temperature. After 30 min, dichloromethane (10 mL) and water (10 mL) were added and the organic layer was collected, dried (MgSO$_4$) and concentrated in vacua. The residue was purified by flash chromatography to afford 0.16 g of the title compound (CH$_2$Cl$_2$ 100% to 5% EtOAc in CH$_2$Cl$_2$). LC-MS: RT=3.97 min. (M+Na)$^+$ 442.

Example 39

(S)-2-(4-tert-Butyl-benzenesulfonyl)-6,6-ethylenedioxy-8a-morpholin-4-ylmethyl-1,2,3,5,6,7,8,8a-octahydro-isoquinoline (20: $L^3$=CH$_2$, $R^3$=morpholino, $R^{4A}$=4-(t-butyl)Ph)

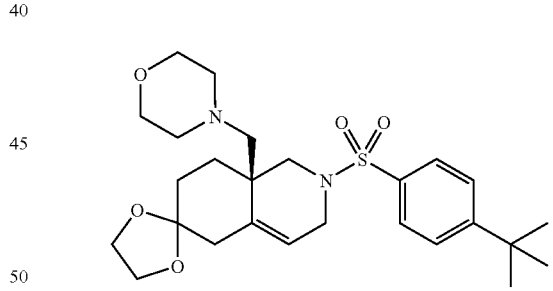

(R)-Enone 13 ($L^3$=CO, $R^3$=OMe, Z=Boc) was prepared according to the literature procedure (*Org. Lett.* 6, 1171 (2004) and was converted to (R)-IA-27 and then to (R)-18 ($R^{4A}$=4-(t-butyl)Ph) according to Schemes XII and XIII. Compound (R)-18 ($R^{4A}$=4-(t-butyl)Ph) (69 mg, 0.16 mmol) was dissolved in dichloromethane (5 mL) and morpholine (30 μL, 0.32 mmol) and sodium triacetoxyborohydride (68 mg, 0.32 mmol) were added and the resulting mixture was stirred for 19 h. Saturated sodium bicarbonate solution (10 mL) was added and the organics extracted with 3×10 mL dichloromethane, dried (MgSO$_4$) and concentrated in vacuo. The residue was purified by flash chromatography to afford 0.16 g of the title compound (CH$_2$Cl$_2$ 100% to 5% EtOAc in CH$_2$Cl$_2$). LC-MS: RT=2.64 min. (M+H)$^+$ 491.

Example 40

(S)-2-(4-tert-Butyl-benzenesulfonyl)-8a-morpholin-4ylmethyl 1,3,4,7,8-8a-hexahydro-2H-isoquinolin-6-one (IA-30: $L^3=CH_2$, $R^3=$morpholino, $R^{4.4}=$4-(t-butyl)Ph)

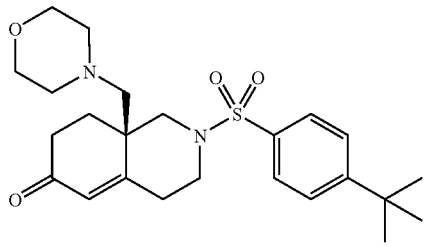

Compound (S)-19 ($R^{3B/C}=CH_2CH_2OCH_2CH_2$, $R^{4.4}=$4-(t-butyl)Ph, (245 mg, 0.5 mmol) dissolved in dichloromethane (2 mL) and cooled to 0° C. where perchloric acid (50 µL) was added. After 40 min at this temperature, the reaction was warmed to ambient temperature and stirring continued for an additional 90 min. Saturated sodium bicarbonate solution (10 mL) was added and the mixture was extracted with 3× $CH_2Cl_2$ (10 mL), and concentrated in vacuo. The residue was purified by flash chromatography ($CH_2Cl_2$ 100% to 10% EtOAc in $CH_2Cl_2$) to afford 120 mg of the title compound. LC-MS: RT=2.8 min. (M+H)+ 447.

Example 41

Glucocorticoid Receptor Binding Assay

The following is a description of an assay for determining the inhibition of dexamethasone binding of the Human Recombinant Glucocorticoid Receptor:

Binding protocol: Compounds are tested in a binding displacement assay using human recombinant glucocorticoid receptor with 3H-dexamethasone as the ligand. The source of the receptor is recombinant baculovirus-infected insect cells. This GR is a full-length steroid hormone receptor likely to be associated with heat-shock and other endogenous proteins.

The assay is carried out in v-bottomed 96-well polypropylene plates in a final volume of 200 µl containing 0.5 nM GR solution, 2.5 nM 3H-dexamethasone (Amersham TRK 645) in presence of test compounds, test compound vehicle (for total binding) or excess dexamethasone (20 µM, to determine non-specific binding) in an appropriate volume of assay buffer.

For the Primary Screen, test compounds are tested at 1 µM in duplicate. These compounds are diluted from 10 mM stock in 100% DMSO. After dilution to 100 µM, 5 µl are added to 245 µl assay buffer to obtained 2 µM compound and 2% DMSO.

For the IC50 determinations, test compounds are tested at 6 concentrations in duplicate (concentration range depends on % inhibition binding that was obtained in the Primary Screen,). Test compounds are diluted from 10 mM stock in 100% DMSO. The tested solutions are prepared at 2× final assay concentration in 2% DMSO/assay buffer.

All reagents and the assay plate are kept on ice during the addition of reagents. The reagents are added to wells of a v-bottomed polypropylene plate in the following order: 50 µl of 10 nM 3H-dexamethasone solution, 100 µl of TB/NSB/ compound solution and 50 µl of 2 nM GR solution. Once all additions are made the incubation mixture is mixed and incubated for 2.5 hrs at 4° C.

After 2.5 hrs incubation, unbound counts are removed with dextran coated charcoal (DCC) as follows: 25 µl of DCC solution (10% DCC in assay buffer) is added to all wells and mixed (total volume 225 µl). Plate is centrifuged at 400 rpm, for 10 minutes, at 4° C. 75 µl of the supernatants (i.e. ⅓ of total volume) is carefully pipetted into an optiplate. 200 µl of scintillation cocktail are added (Microscint-40, Packard Bioscience. B.V.), an adhesive plate seal placed on plate and plate vigorously shaken for approx. 10 minutes. Plate is counted on Topcount.

Data analysis: For the Primary Screen, the results calculated as % inhibition of maximum [$^3$H]-dexamethasone binding (TB). For the IC50 determinations, the results calculated as % inhibition [$^3$H]-dexamethasone bound and fitted to sigmoidal curves (fixed to 100 and 0) to obtain IC50 values (concentration of compound that displaces 50% of the bound counts).

Reagents: Assay buffer: 10 mM potassium phosphate buffer pH 7.6 containing 5 mM DTT, 10 mM sodium molybdate, 100 µM EDTA and 0.1% BSA.

Example 42

Selectivity Binding Assays

Selectivity binding assays were performed on human estrogen (ERα), progesterone (PR), androgen (AR) and mineralocorticoid (MR) receptors. The selectivity assays are carried out in the same assay buffer and volumes as the GR binding assay and DCC is used to separate free from bound label.

Mineralocorticoid binding assay: MR was obtained from Sf9 cells infected with recombinant baculovirus containing MR, and the MR isolated according to the method of Binart et al (Binart, N.; Lombes, M.; Rafestin-Oblin, M. E.; Baulieu, E. E. Characterisation of human mineralocorticoid receptor expressed in the baculovirus system. *PNAS US,* 1991, 88, 10681-10685). Compounds were tested against an appropriate dilution of the MR (determined for each batch of receptor) with 2.4 nM of [$^3$H] aldosterone (Perkin Elmer NET419) and incubated for 60 mins at room temperature.

Estrogen binding assay: Compounds were tested for displacement of 0.56 nM [$^3$H]-estradiol (Perkin Elmer NET517) binding to 0.5 nM ERα (obtained from PanVera 26467A) following an incubation period of 90 mins at room temperature.

Progesterone binding assay: Compounds were tested for displacement of 3 nM [$^3$H]-progesterone (Perkin Elmer NET381) binding to 1 nM PR (obtained from PanVera 24900). This assay was incubated for 120 mins at 4° C.

Androgen binding assay: Compounds were tested, in triplicate, for displacement of 6 nM [$^3$H]-dihydrotestosterone (Perkin Elmer NET453) binding to 3 nM PR (obtained from PanVera 24938). This assay was incubated overnight at 4° C.

Example 43

GR Functional Assay Using SW1353/MMTV-5 Cells

SW1353/MMTV-5 is an adherent human chondrosarcoma cell line that contains endogenous glucocorticoid receptors. It has been transfected with a plasmid (pMAMneo-Luc) encoding firefly luciferase located behind a glucocorticoid-responsive element (GRE) derived from a viral promoter (long terminal repeat of mouse mammary tumor virus). A stable cell line SW1353/MMTV-5 was selected with geneticin, which is required to maintain this plasmid. This cell line is thus sensitive to glucocorticoids (dexamethasone) leading to expression of luciferase ($EC_{50}^{dex}$ 10 nM). This dexamethasone-induced response is gradually lost over time, and a new culture from an earlier passage needs to be started (from a cryo-stored aliquot) every three months.

In order to test for a GR-antagonist, SW1353/MMTV-5 cells are incubated with several dilutions of the compounds in the presence of $5 \times EC_{50}^{dex}$ (50 nM), and the inhibition of induced luciferase expression measured using a luminescence in a Topcounter (LucLite kit from Perkin Elmer). For each assay, a dose-response curve for dexamethasone is set up in order to determine the $EC_{50}^{dex}$ required for calculating the $K_i$ from the $IC_{50}$'s of each tested compound.

SW1353/MMTV-5 cells are distributed in 96-well plates and incubated in medium (without geneticin) for 24 hrs (in the absence of $CO_2$). Dilutions of the compounds in medium +50 nM dexamethasone are added and the plates further incubated for another 24 hrs after which the luciferase expression is measured.

Example 44

Cytotoxicity Assay Using SW1353/Luc-4 Cells

In order to exclude the possibility that compounds inhibit the dexamethasone-induced luciferase response (GR-antagonist) due to their cytotoxicity or due to their direct inhibition of luciferase, a SW1353 cell line was developed that constitutively expresses firefly luciferase, by transfection with plasmid pcDNA3.1-Luc and selection with geneticin. The cell line SW1353/Luc-4 was isolated that constitutively expresses luciferase.

SW1353/Luc-4 cells are distributed in 96-well plates and incubated (no $CO_2$) for 24 hrs, after which compound dilutions (without dexamethasone) are added. After a further 24 hrs incubation, luciferase expression is measured using the "LucLite" assay.

Example 45

MR and PR Functional Assays Using T47D/MMTV-5 Cells

T47D/MMTV-5 is an adherent human breast carcinoma cell line containing endogenous mineralocorticoid-(MR) and progesterone (PR) receptors. As for the SW1353 cell line, T47D cells have been transfected with the same pMAMneo-Luc plasmid, and stable lines selected with geneticin. A cell line T47D/MMTV-5 was isolated which responds to aldosterone ($EC_{50}^{ald}$ 100 nM), and progesterone ($EC_{50}^{prog}$ 10 nM), leading to expression of luciferase.

As for the GR assay to test for MR- or PR-antagonists, the T47D/MMTV-5 cells are incubated with several dilutions of the compounds in the presence of the $5 \times EC_{50}$ of the agonist aldosterol ($EC_{50}^{ald}$ 100 nM) or progesterone ($EC_{50}^{prog}$ 10 nM) respectively. For each assay a dose response curve is set up for both aldosterone and progesterone.

T47D/MMTV-5 cells are distributed in 96-well plates (100 µl) in RPMI1640 medium +10% Charcoal stripped FCS. The cells are incubated for 24 hrs in the $CO_2$-oven. Then 100 µl of the compound dilutions in medium +agonist (500 nm aldost; 50 nM progest) are added, and the plates further incubated for another 24 hrs after which the luciferase expression is measured.

What is claimed is:
1. A compound having the formula:

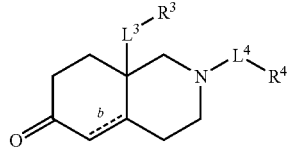

wherein:
$L^4$ is selected from a bond, substituted or unsubstituted alkylene, and substituted or unsubstituted heteroalkylene;
$L^3$ is unsubstituted methylene;
the dashed line b is optionally a bond;
$R^3$ has the formula:

wherein
q is an integer selected from 1 to 5;
$R^{3D}$ is a member independently selected from hydrogen, halogen, —OH, —COOH, —$CF_3$, —$NH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$NR^{3D1}R^{3D2}$, —$OR^{3D3}$, —$C(O)NR^{3D4}R^{3D5}$, and —$C(O)R^{3D6}$,
wherein
$R^{3D1}$, $R^{3D2}$, $R^{3D3}$, $R^{3D4}$, $R^{3D5}$, and $R^{3D6}$ are members independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein
$R^{3D1}$ and $R^{3D2}$ are optionally joined to form a substituted or unsubstituted ring with the nitrogen to which they are attached, and
$R^{3D4}$ and $R^{3D5}$ are optionally joined to form a substituted or unsubstituted ring with the nitrogen to which they are attached;
$R^4$ has the formula:

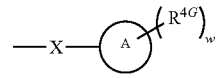

wherein
$R^{4G}$ is a member independently selected from hydrogen, halogen, —OH, —COOH, —$CF_3$, —$NH_2$, —SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

A is a substituted or unsubstituted ring selected from substituted or unsubstituted $(C_3-C_7)$cycloalkyl, substituted or unsubstituted 3-7 membered heterocycloalkyl, substituted or unsubstituted aryl, and substituted or unsubstituted heteroaryl;

X is a member selected from a bond, —S(O)$_v$—, and —S(O)$_v$NR$^{4I}$—, wherein R$^{4I}$ is a member selected from hydrogen, substituted or unsubstituted alkyl, and substituted or unsubstituted heteroalkyl, and v is 0, 1, or 2; and w is an integer from 1 to 5.

2. The compound of claim 1, wherein the dashed line b is a bond.

3. The compound of claim 1, wherein q is an integer selected from 1 to 3; and

R$^{3D}$ is a member independently selected from hydrogen, substituted alkyl, substituted or unsubstituted heteroalkyl, substituted cycloalkyl, substituted or unsubstituted heterocycloalkyl, substituted aryl, and substituted or unsubstituted heteroaryl.

4. The compound of claim 1, wherein

R$^{3D}$ is a member independently selected from hydrogen, R$^{3D7}$-substituted $(C_1-C_{10})$alkyl, R$^{3D7}$-substituted or unsubstituted 2-10 membered heteroalkyl, R$^{3D7}$-substituted or unsubstituted $(C_3-C_8)$cycloalkyl, R$^{3D7}$-substituted or unsubstituted 3-8 membered heterocycloalkyl, R$^{3D8}$-substituted or unsubstituted aryl, R$^{3D8}$-substituted or unsubstituted heteroaryl, —NR$^{3D1}$R$^{3D2}$, —OR$^{3D3}$, —C(O)NR$^{3D4}$R$^{3D5}$, and —C(O)R$^{3D6}$, wherein R$^{3D1}$, R$^{3D2}$, R$^{3D3}$, R$^{3D4}$, R$^{3D5}$, and R$^{3D6}$ are members independently selected from hydrogen, R$^{3D7}$-substituted or unsubstituted alkyl, R$^{3D7}$-substituted or unsubstituted heteroalkyl, R$^{3D7}$-substituted or unsubstituted cycloalkyl, R$^{3D7}$-substituted or unsubstituted heterocycloalkyl, R$^{3D8}$-substituted or unsubstituted aryl, and R$^{3D8}$-substituted or unsubstituted heteroaryl, wherein R$^{3D1}$ and R$^{3D2}$ are optionally joined with the nitrogen to which they are attached to form a R$^{3D7}$-substituted or unsubstituted heterocycloalkyl, or R$^{3D8}$-substituted or unsubstituted heteroaryl, and wherein R$^{3D4}$ and R$^{3D5}$ are optionally joined with the nitrogen to which they are attached to form a R$^{3D7}$-substituted or unsubstituted heterocycloalkyl, or R$^{3D8}$-substituted or unsubstituted heteroaryl, wherein R$^{3D7}$ is a member selected from halogen, oxo, —OH, —COOH, —CF$_3$, —NH$_2$, —SH, R$^{3D9}$-substituted or unsubstituted $(C_1-C_{10})$alkyl, R$^{3D9}$-substituted or unsubstituted 2-10 membered heteroalkyl, R$^{3D9}$-substituted or unsubstituted $(C_3-C_8)$cycloalkyl, R$^{3D9}$-substituted or unsubstituted 3-8 membered heterocycloalkyl, R$^{3D10}$-substituted or unsubstituted aryl, and R$^{3D10}$-substituted or unsubstituted heteroaryl, and R$^{3D8}$ is a member selected from halogen, —OH, —COOH, —CF$_3$, —NH$_2$, —SH, R$^{3D9}$-substituted or unsubstituted $(C_1-C_{10})$alkyl, R$^{3D9}$-substituted or unsubstituted 2-10 membered heteroalkyl, R$^{3D9}$-substituted or unsubstituted $(C_3-C_8)$cycloalkyl, R$^{3D9}$-substituted or unsubstituted 3-8 membered heterocycloalkyl, R$^{3D10}$-substituted or unsubstituted aryl, and R$^{3D10}$-substituted or unsubstituted heteroaryl, R$^{3D9}$ is a member selected from halogen, oxo, —OH, —COOH, —CF$_3$, —NH$_2$, —SH, unsubstituted $(C_1-C_{10})$alkyl, unsubstituted 2-10 membered heteroalkyl, unsubstituted $(C_3-C_8)$cycloalkyl, unsubstituted 3-8 membered heterocycloalkyl, unsubstituted aryl, and unsubstituted heteroaryl, and R$^{3D10}$ is a member selected from halogen, —OH, —COOH, —CF$_3$, —NH$_2$, —SH, unsubstituted $(C_1-C_{10})$alkyl, unsubstituted 2-10 membered heteroalkyl, unsubstituted $(C_3-C_8)$cycloalkyl, unsubstituted 3-8 membered heterocycloalkyl, unsubstituted aryl, and unsubstituted heteroaryl.

5. The compound of claim 4, wherein R$^3$ has the formula:

$$\text{—}\langle\text{phenyl}\rangle\text{—R}^{3D} \quad (IV)$$

wherein

R$^{3D}$ is a member selected from hydrogen, R$^{3D7}$-substituted $(C_1-C_5)$alkyl, R$^{3D7}$-substituted or unsubstituted 2-5 membered heteroalkyl, R$^{3D7}$-substituted $(C_5-C_7)$cycloalkyl, R$^{3D7}$-substituted or unsubstituted 5-7 membered heterocycloalkyl, R$^{3D8}$-substituted aryl, R$^{3D8}$-substituted or unsubstituted heteroaryl, —NR$^{3D1}$R$^{3D2}$, —OR$^{3D3}$, —C(O)NR$^{3D4}$R$^{3D5}$, and —C(O)R$^{3D6}$.

6. The compound of claim 5, wherein

R$^{3D}$ is a member selected from —NR$^{3D1}$R$^{3D2}$, —OR$^{3D3}$, —C(O)NR$^{3D4}$R$^{3D5}$, and R$^{3D7}$-substituted or unsubstituted heteroaryl comprising a ring nitrogen, wherein R$^{3D1}$ and R$^{3D2}$ are members independently selected from hydrogen, R$^{3D7}$-substituted alkyl, R$^{3D7}$-substituted or unsubstituted heteroalkyl, R$^{3D7}$-substituted or unsubstituted heterocycloalkyl, and R$^{3D8}$-substituted or unsubstituted heteroaryl, wherein R$^{3D1}$ and R$^{3D2}$ are optionally joined with the nitrogen to which they are attached to form a R$^{3D7}$-substituted or unsubstituted heterocycloalkyl, or R$^{3D8}$-substituted or unsubstituted heteroaryl, wherein said ring optionally comprises an additional ring heteroatom; and R$^{3D3}$, R$^{3D4}$ and R$^{3D5}$ are members independently selected from hydrogen, R$^{3D7}$-substituted or unsubstituted heteroalkyl comprising a nitrogen heteroatom, R$^{3D7}$-substituted or unsubstituted heterocycloalkyl comprising a ring nitrogen, R$^{3D8}$-substituted or unsubstituted heteroaryl comprising a ring nitrogen, and alkyl substituted with a R$^{3D9}$-substituted or unsubstituted heteroalkyl comprising a nitrogen heteroatom, R$^{3D9}$-substituted or unsubstituted heterocycloalkyl comprising a ring nitrogen, or R$^{3D10}$-substituted or unsubstituted heteroaryl comprising a ring nitrogen, wherein R$^{3D4}$ and R$^{3D5}$ are optionally joined with the nitrogen to which they are attached to form a R$^{3D7}$-substituted or unsubstituted heterocycloalkyl, or R$^{3D8}$-substituted or unsubstituted heteroaryl, wherein said ring optionally comprises a heteroatom.

7. The compound of claim 6, wherein

R$^{3D1}$ and R$^{3D2}$, and R$^{3D4}$ and R$^{3D5}$ are optionally joined with the nitrogen to which they are attached to form a R$^{3D7}$-substituted or unsubstituted heterocycloalkyl comprising an additional heteroatom, or R$^{3D8}$-substituted or unsubstituted heteroaryl comprising an additional heteroatom.

8. The compound of claim 7, wherein $R^{3D1}$ and $R^{3D2}$, and $R^{3D4}$ and $R^{3D5}$ are optionally joined with the nitrogen to which they are attached to form a $R^{3D8}$-substituted or unsubstituted oxazolyl, imidazolyl, thiazolyl, isooxazolyl, pyrazolyl, isothiazolyl, purinyl, pyradizinyl, pyrimidinyl, pyrazinyl, or quinoxalinyl.

9. The compound of claim 1, wherein $R^{4G}$ is a member independently selected from hydrogen, halogen, —OH, —COOH, —$CF_3$, —$NH_2$, —SH, $R^{4G1}$-substituted or unsubstituted alkyl, $R^{4G1}$-substituted or unsubstituted heteroalkyl, $R^{4G1}$-substituted or unsubstituted cycloalkyl, $R^{4G1}$-substituted or unsubstituted heterocycloalkyl, $R^{4G2}$-substituted or unsubstituted aryl, and $R^{4G2}$-substituted or unsubstituted heteroaryl, wherein $R^{4G1}$ is a member selected from halogen, oxo, —OH, —COOH, —$CF_3$, —$NH_2$, —SH, $R^{4G3}$-substituted or unsubstituted ($C_1$-$C_{10}$)alkyl, $R^{4G3}$-substituted or unsubstituted 2-10 membered heteroalkyl, $R^{4G3}$-substituted or unsubstituted ($C_3$-$C_8$)cycloalkyl, $R^{4G3}$-substituted or unsubstituted 3-8 membered heterocycloalkyl, $R^{4G4}$-substituted or unsubstituted aryl, and $R^{4G4}$-substituted or unsubstituted heteroaryl, and $R^{4G2}$ is a member selected from halogen, —OH, —COOH, —$CF_3$, —$NH_2$, —SH, $R^{4G3}$-substituted or unsubstituted ($C_1$-$C_{10}$)alkyl, $R^{4G3}$-substituted or unsubstituted 2-10 membered heteroalkyl, $R^{4G3}$-substituted or unsubstituted ($C_3$-$C_8$)cycloalkyl, $R^{4G3}$-substituted or unsubstituted 3-8 membered heterocycloalkyl, $R^{4G4}$-substituted or unsubstituted aryl, and $R^{4G4}$-substituted or unsubstituted heteroaryl, $R^{4G3}$ is a member selected from halogen, oxo, —OH, —COOH, —$CF_3$, —$NH_2$, —SH, unsubstituted ($C_1$-$C_{10}$)alkyl, unsubstituted 2-10 membered heteroalkyl, unsubstituted ($C_3$-$C_8$)cycloalkyl, unsubstituted 3-8 membered heterocycloalkyl, unsubstituted aryl, and unsubstituted heteroaryl, and $R^{4G4}$ is a member selected from halogen, —OH, —COOH, —$CF_3$, —$NH_2$, —SH, unsubstituted ($C_1$-$C_{10}$)alkyl, unsubstituted 2-10 membered heteroalkyl, unsubstituted ($C_3$-$C_8$)cycloalkyl, unsubstituted 3-8 membered heterocycloalkyl, unsubstituted aryl, and unsubstituted heteroaryl.

10. The compound of claim 9, wherein A is a member selected from phenyl, pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, thienyl, triazinyl, thiadiazolyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, and piperazinyl.

11. The compound of claim 1, wherein $R^{4G}$ is selected from hydrogen, substituted ($C_1$-$C_5$)alkyl, substituted or unsubstituted 2-5 membered heteroalkyl, substituted ($C_5$-$C_7$)cycloalkyl, substituted or unsubstituted heterocycloalkyl, substituted aryl, and substituted or unsubstituted heteroaryl;

A is a substituted or unsubstituted ring selected from substituted or unsubstituted 3-7 membered heterocycloalkyl, substituted or unsubstituted aryl, and substituted or unsubstituted heteroaryl; and $R^{4I}$ is hydrogen.

12. The compound of claim 1, wherein $R^{4G}$ is a branched or unbranched ($C_1$-$C_{10}$)alkyl.

13. The compound of claim 1, wherein X is —S(O)$_2$—.

14. The compound of claim 1, wherein $L^4$ is selected from a bond and unsubstituted ($C_1$-$C_5$)alkylene.

15. The compound of claim 1 wherein the dashed line b is a bond;

$R^{4G}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, X is —S(O)$_2$—;

W is 1;

and $L^4$ is a bond.

16. The compound of claim 1 having the formula:

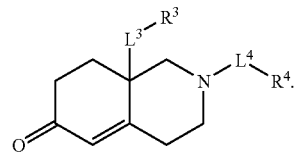

(VIII)

17. The compound of claim 1 having the formula:

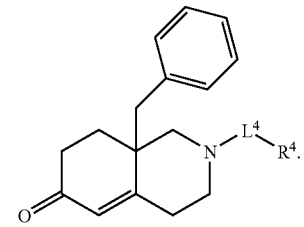

(XI)

18. The compound of claim 1 having the formula:

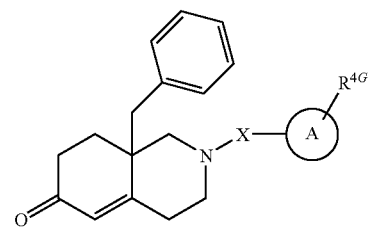

(X)

wherein $R^{4G}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

and

X is a member selected from a bond, —S(O)$_2$—, and —S(O)$_2$NR$^{4I}$—, wherein $R^{4I}$ is a member selected from hydrogen, substituted or unsubstituted alkyl, and substituted or unsubstituted heteroalkyl.

19. The compound of claim 1 having the formula:

(CXX)

wherein

R^{4A} is selected from the group consisting of cycloalkyl, heterocycloalkyl, aryl, and heteroaryl.

20. A compound selected from the group consisting of:

(XIII)

(XIV)

(XV)

(XVI)

(XVII)

-continued (XVIII)

(XIX)

(XX)

(XXI)

(XXII)

(XXIII)

(XXIV)
(XXV)
(XXVI)
(XXVII)
(XXVIII)
(XXIX)
(XXX)
(XXXI)
(XXXII)
(XXXIII)
(XXXIV)
(XXXV)

(XXXVI)
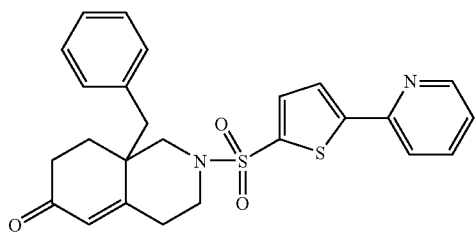
(XLII)
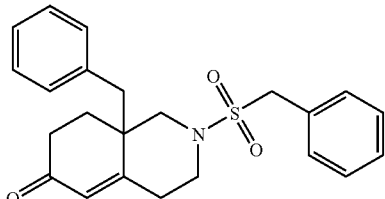
(XXXVII)
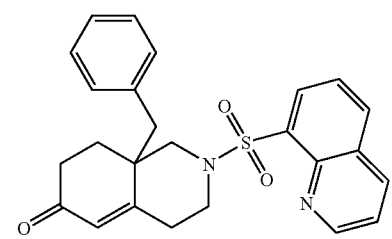
(XLIII)
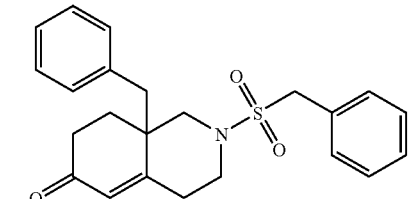
(XXXVIII)
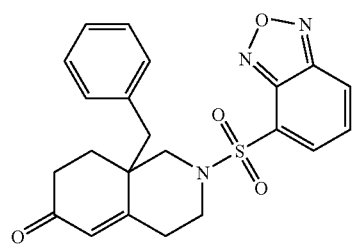
(XLIV)
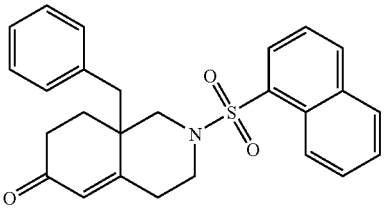
(XXXIX)
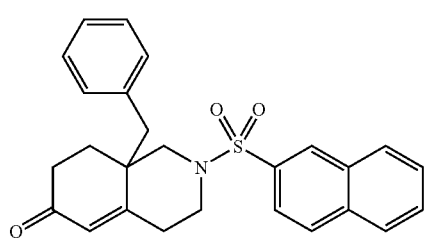
(XLV)
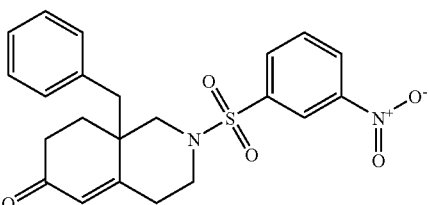
(XL)
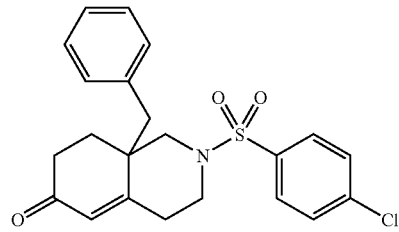
(XLVI)
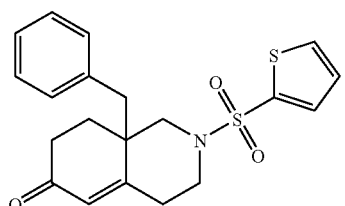
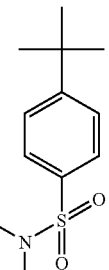
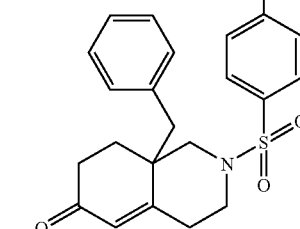
(XLI)
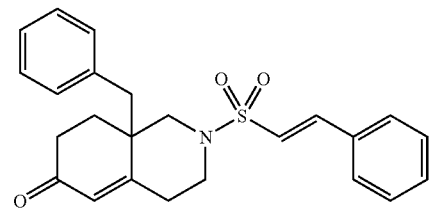
(XLVII)
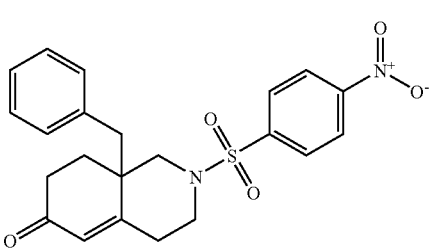

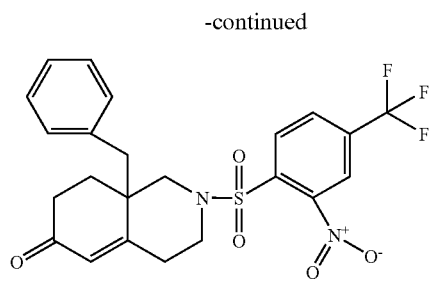
(XLVIII)
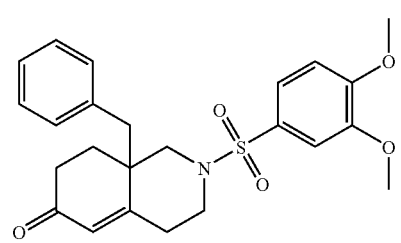
(XLIX)
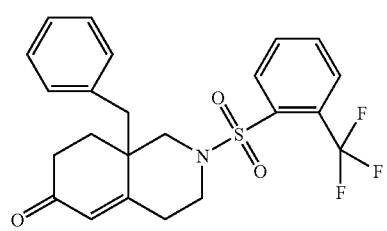
(L)
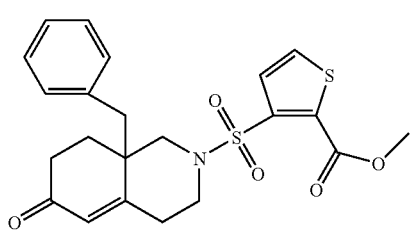
(LI)
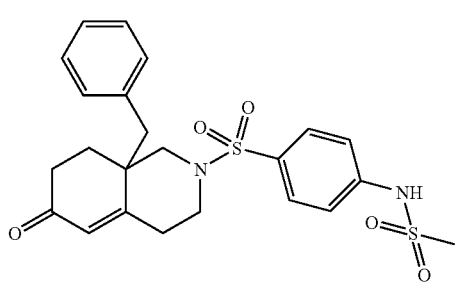
(LII)
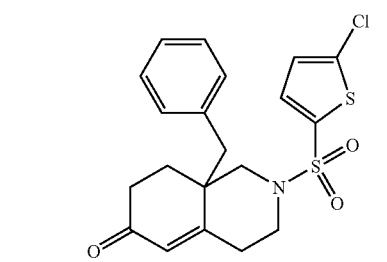
(LIII)
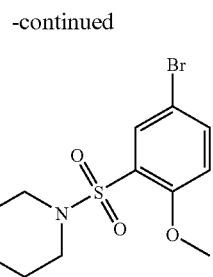
(LIV)
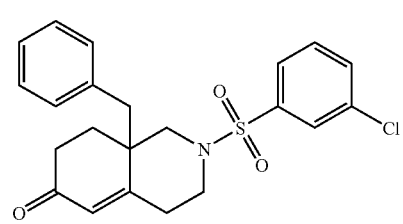
(LV)
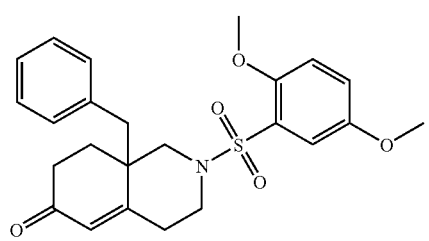
(LVI)
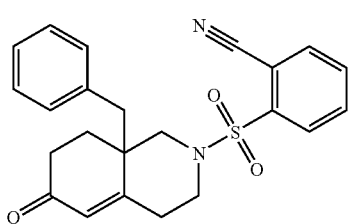
(LVII)
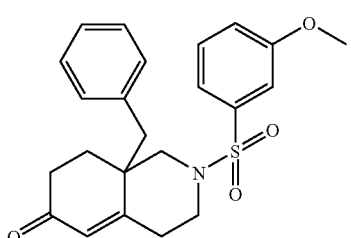
(LVIII)
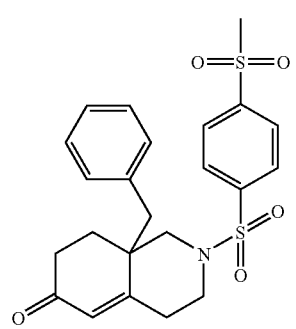
(LIX)

-continued
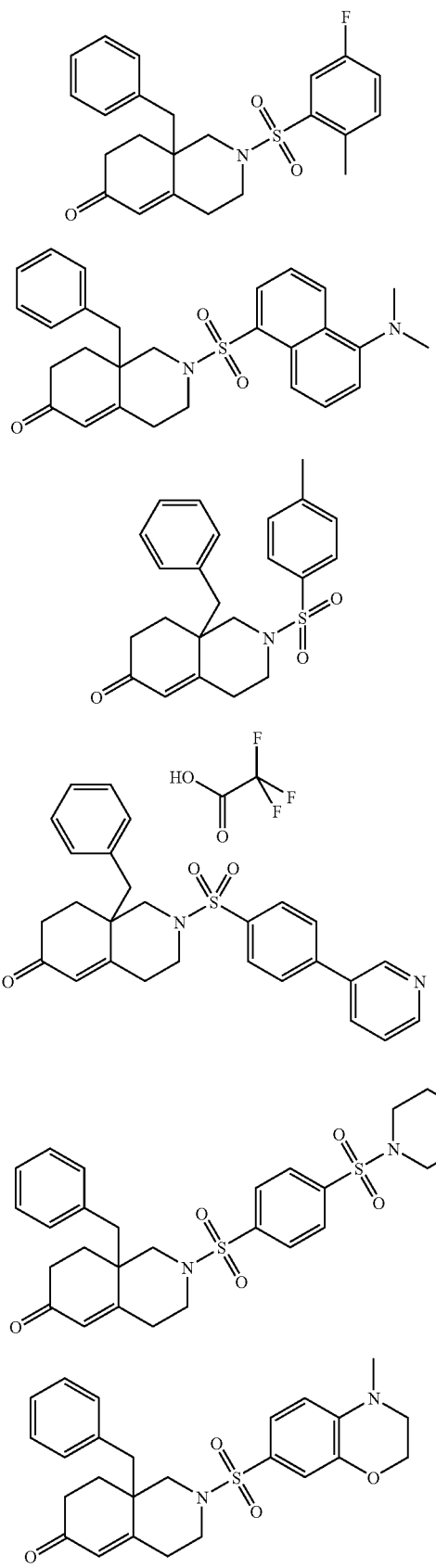
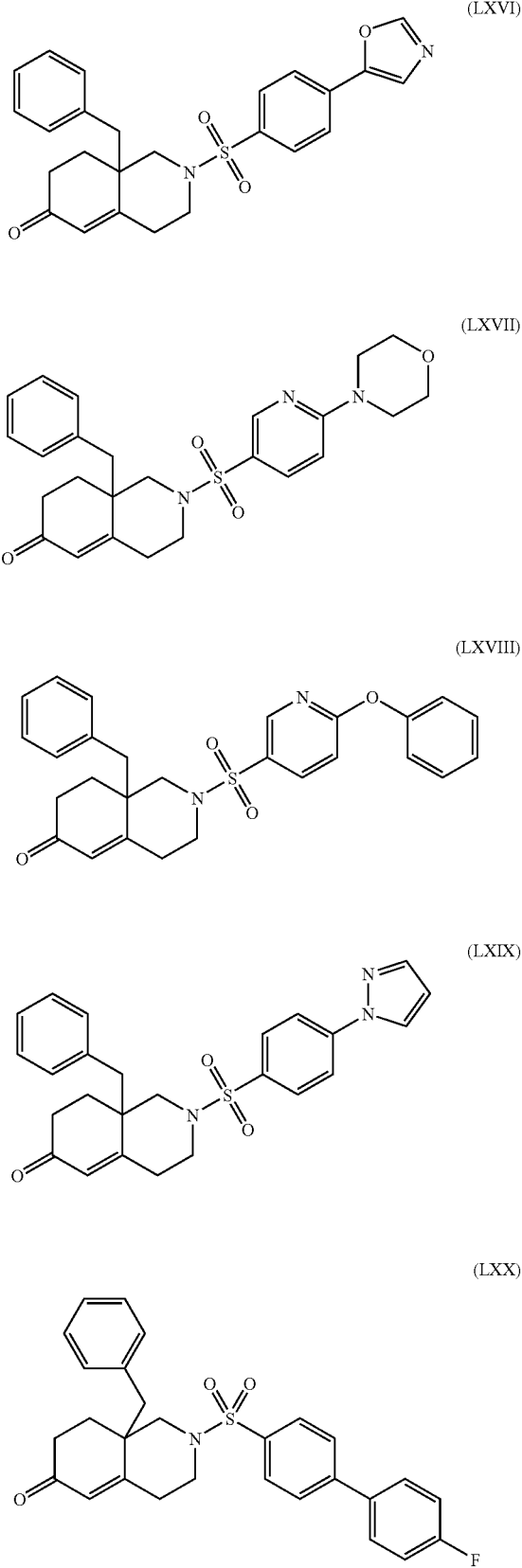

-continued
(LXXI)
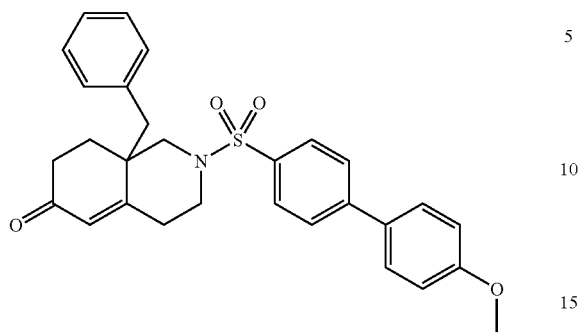
(LXXII)
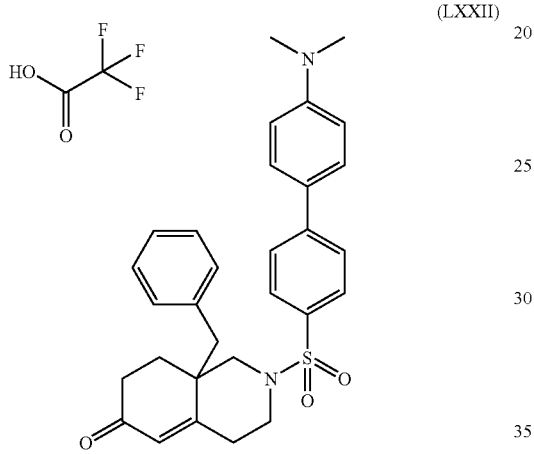
(LXXIII)
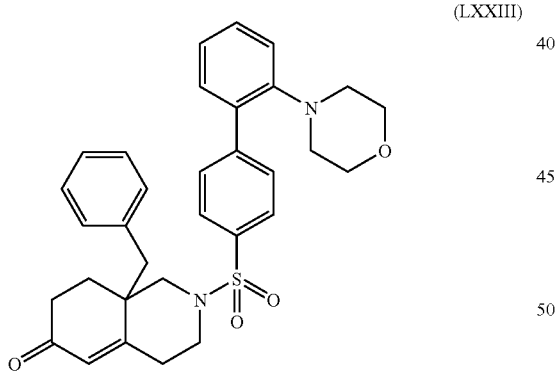
(LXXIV)
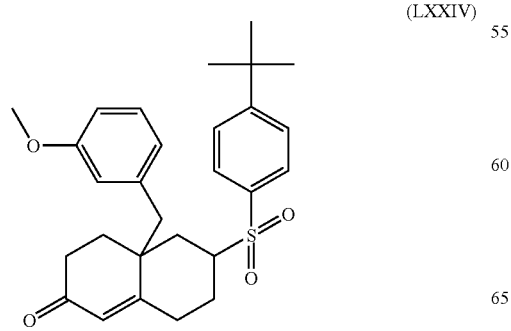
-continued
(LXXV)
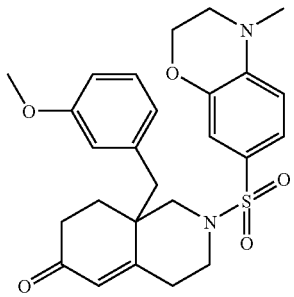
(LXXVI)
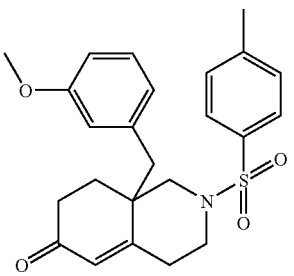
(LXXVII)
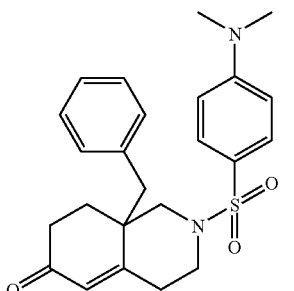
(LXXVIII)
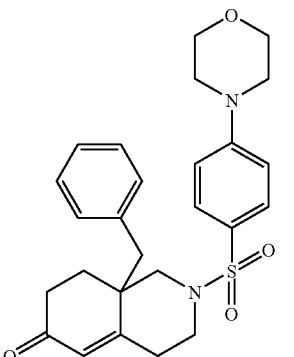
(LXXIX)
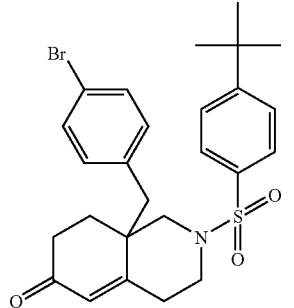

-continued
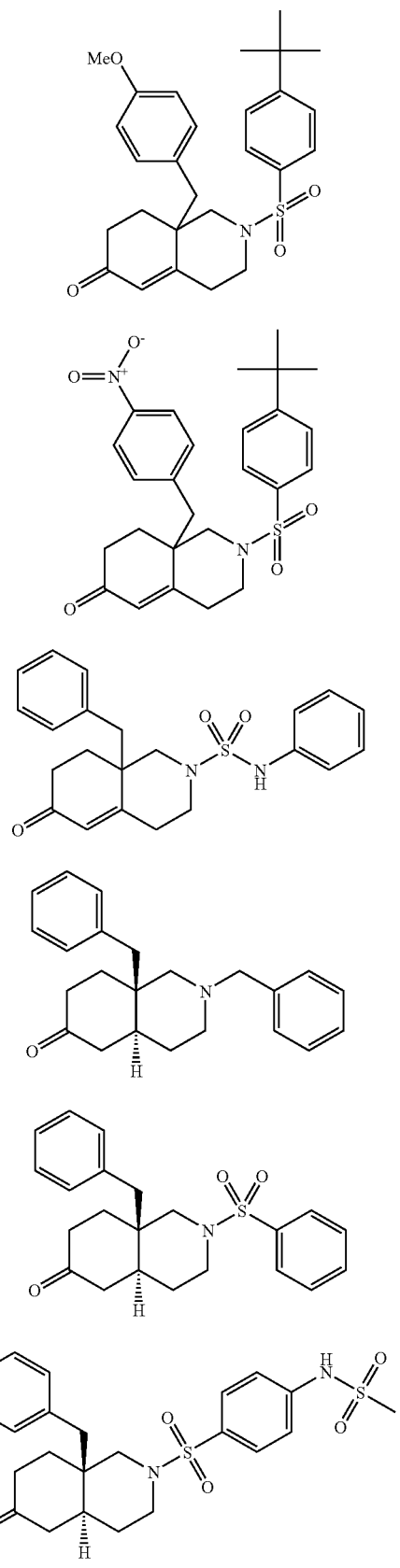
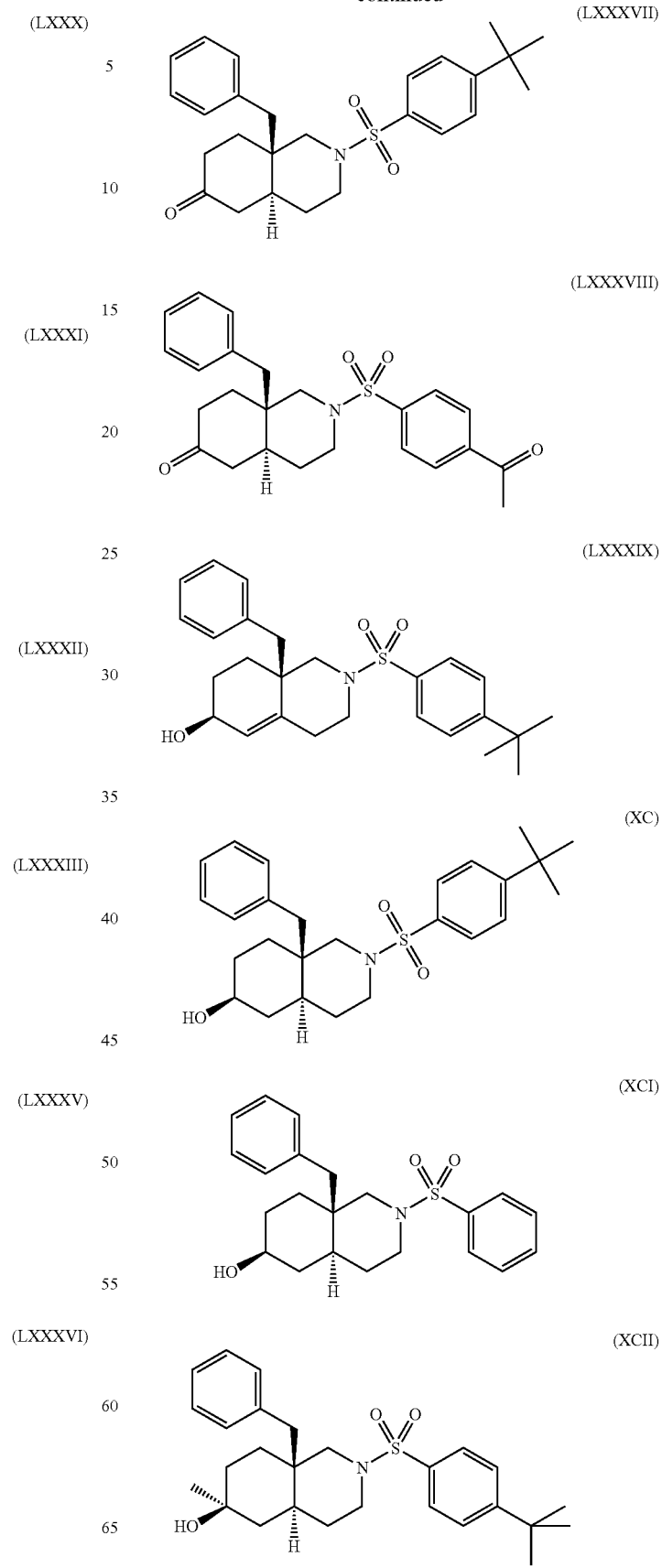

107
-continued
(XCIII)
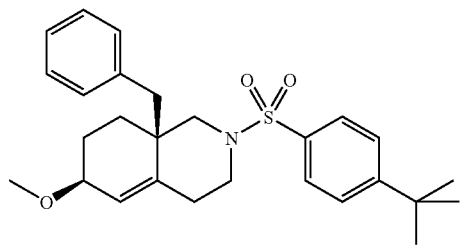
(XCIV)
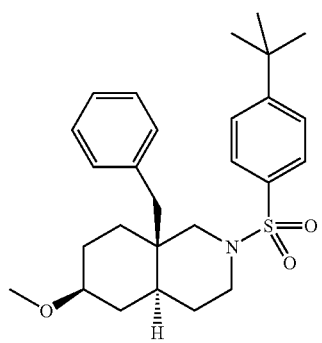
(XCV)
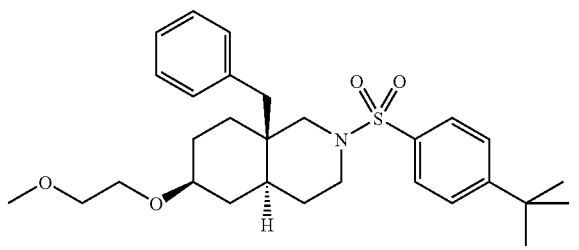
(XCVI)
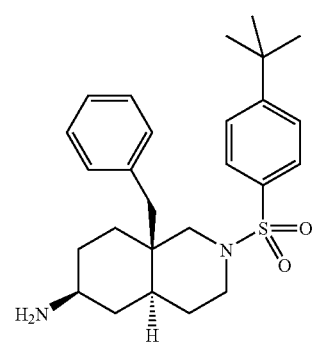
(XCVII)
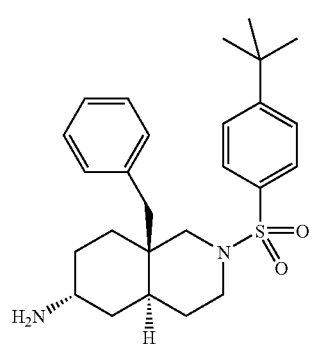
108
-continued
(XCVIII)
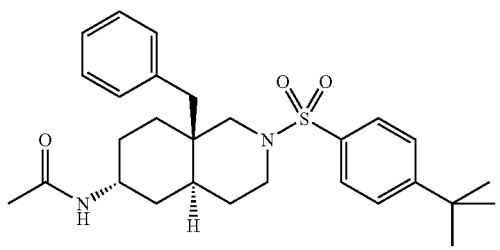
(XCIX)
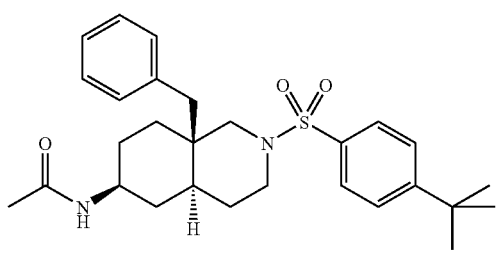
(C)
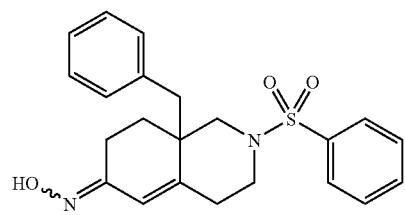
(CI)
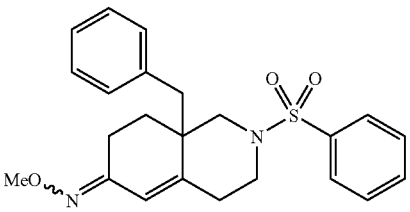
(CII)
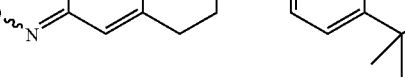
(CIII)
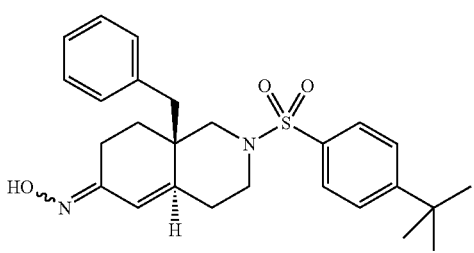

-continued
(CIV)
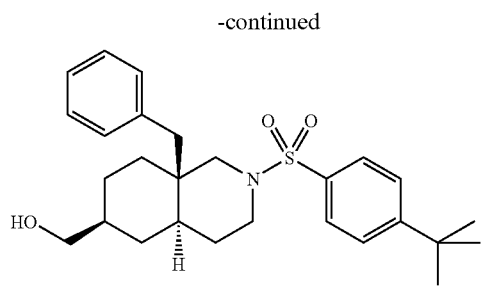
(CV)
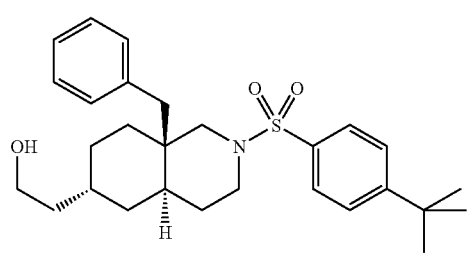
(CVI)
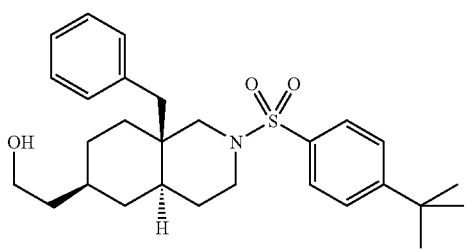
(CVIII)
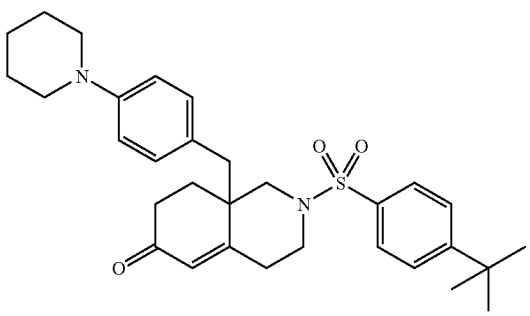
(CIX)
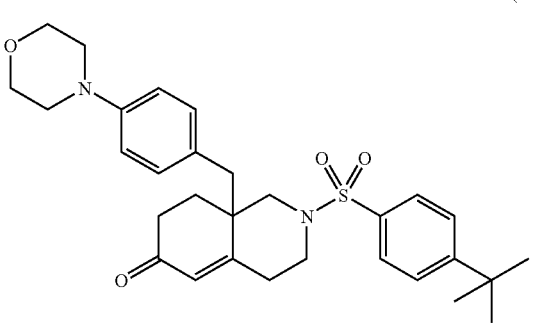
-continued
(CX)
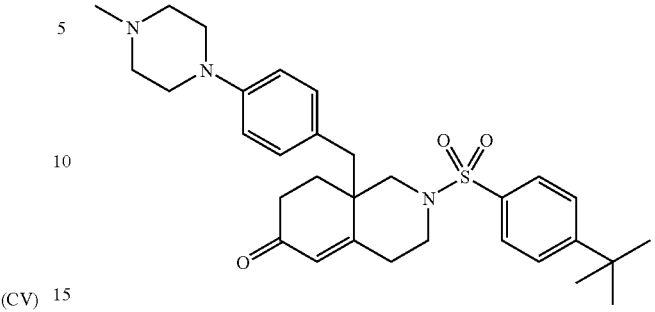
(CXI)
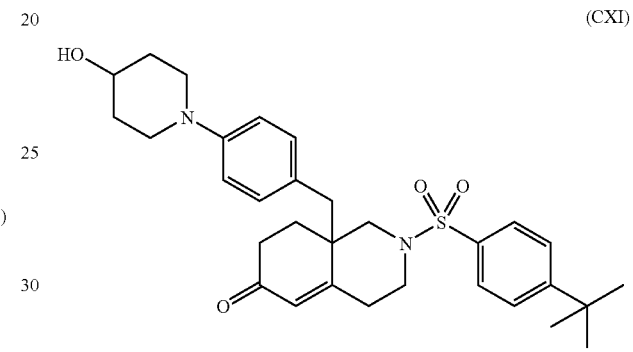
(CXII)
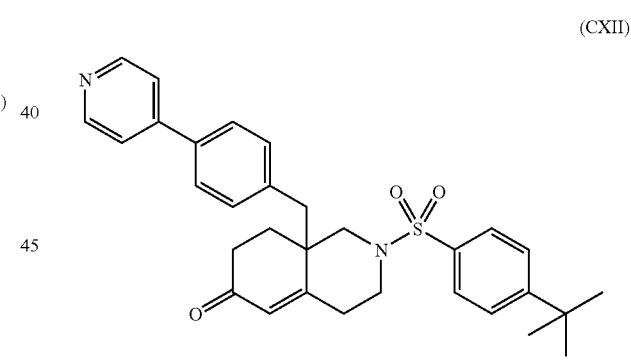
(CXIII)
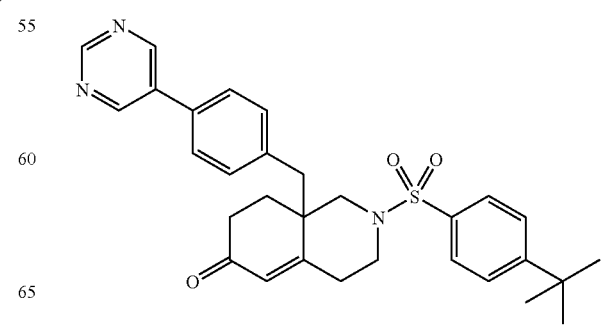

-continued
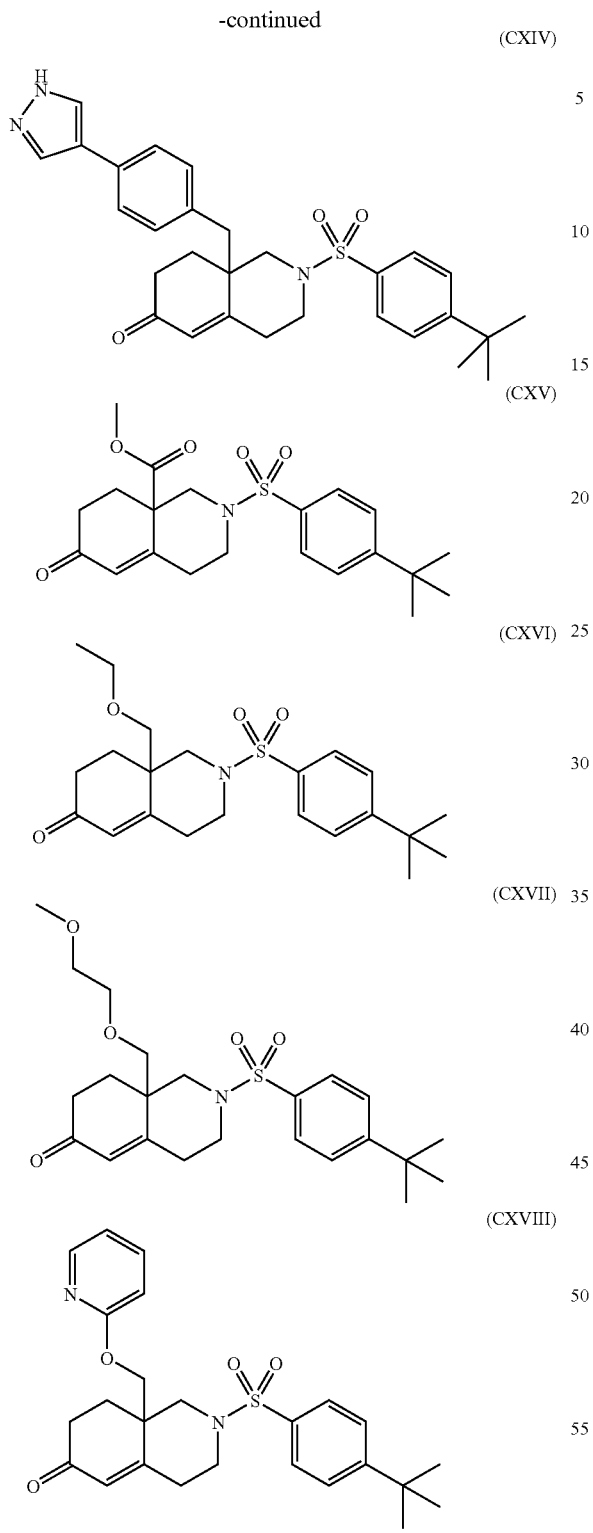
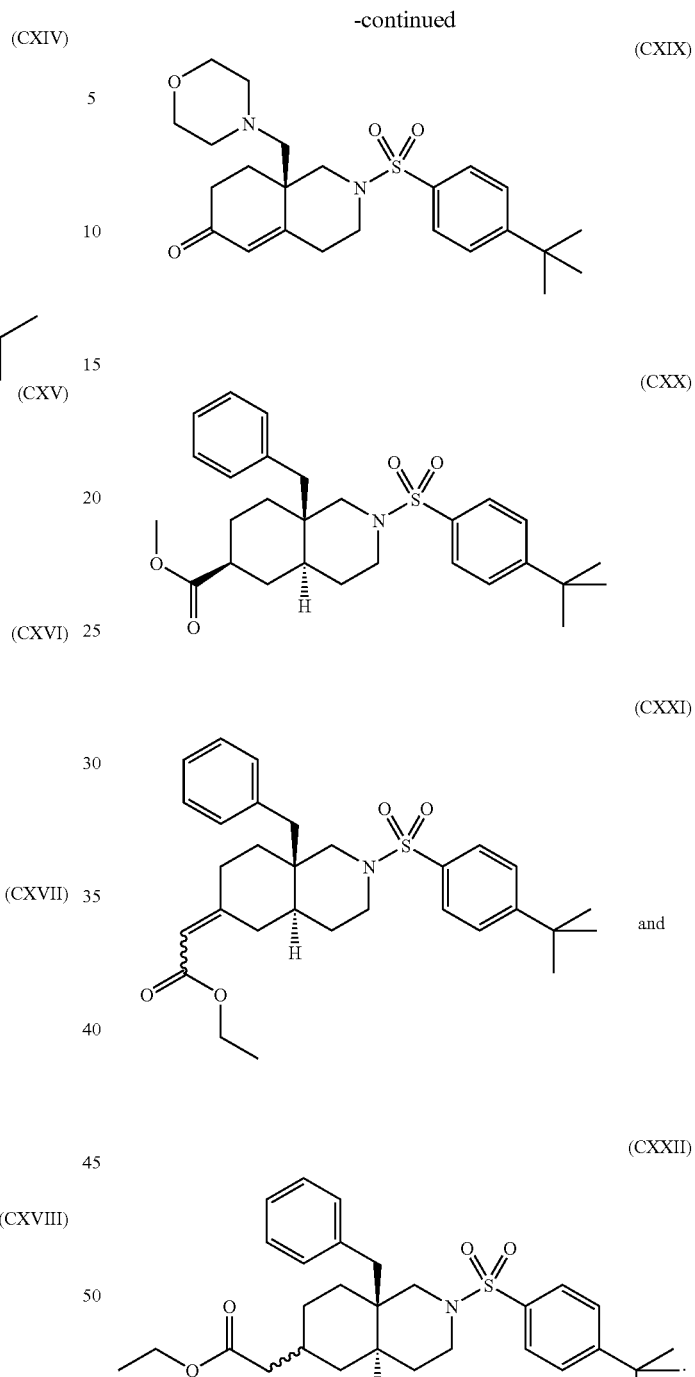
21. A pharmaceutical composition comprising a pharmaceutically acceptable excipient and the compound of claim 1.
* * * * *

UNITED STATES PATENT AND TRADEMARK OFFICE
CERTIFICATE OF CORRECTION

PATENT NO. : 7,678,813 B2  
APPLICATION NO. : 10/596998  
DATED : March 16, 2010  
INVENTOR(S) : Clark et al.

Page 1 of 1

It is certified that error appears in the above-identified patent and that said Letters Patent is hereby corrected as shown below:

In claim 20, column 103, lines 55-65, please insert an --N-- to Scheme LXXIV as follows:

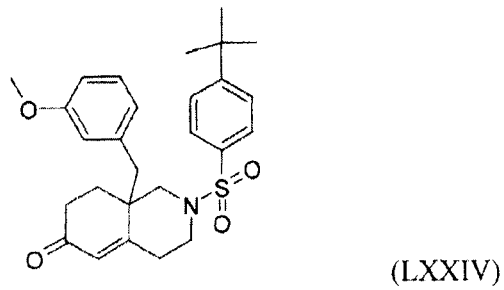

(LXXIV)

Signed and Sealed this

Eleventh Day of May, 2010

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,678,813 B2 | Page 1 of 1 |
| APPLICATION NO. | : 10/596998 | |
| DATED | : March 16, 2010 | |
| INVENTOR(S) | : Robin D. Clark et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 0 days.

should read (*) Notice: Subject to any disclaimer, the term of this patent is extended or adjusted under 35 U.S.C. 154(b) by 420 days.

Signed and Sealed this

Tenth Day of August, 2010

David J. Kappos
*Director of the United States Patent and Trademark Office*